(12) United States Patent
Aklog et al.

(10) Patent No.: US 12,156,693 B2
(45) Date of Patent: Dec. 3, 2024

(54) SYSTEMS AND METHODS FOR MINIMALLY-INVASIVE DIVISION OF FIBROUS STRUCTURES

(71) Applicant: PAVmed Inc., New York, NY (US)

(72) Inventors: Lishan Aklog, Purchase, NY (US); Brian J. deGuzman, Scottsdale, AZ (US); Nathan H. White, Longmont, CO (US); Joshua K. Goetz, Broomfield, CO (US); Samuel V. Verplanck, Boulder, CO (US); Richard D. Yazbeck, Norwell, MA (US); Taylor Bensel, East Walpole, MA (US); Shaun O'Neil, Cardiff, CA (US)

(73) Assignee: PAVmed Inc., New York, NY (US)

( * ) Notice: Subject to any disclaimer, the term of this patent is extended or adjusted under 35 U.S.C. 154(b) by 460 days.

(21) Appl. No.: 16/884,648

(22) Filed: May 27, 2020

(65) Prior Publication Data

US 2021/0369337 A1 Dec. 2, 2021

(51) Int. Cl.
*A61B 18/14* (2006.01)
*A61B 18/00* (2006.01)
(Continued)

(52) U.S. Cl.
CPC ...... *A61B 18/1492* (2013.01); *A61B 18/1206* (2013.01); *A61B 90/37* (2016.02);
(Continued)

(58) Field of Classification Search
CPC .. A61B 2018/00285; A61B 2018/0022; A61B 2018/00077; A61B 2018/00601;
(Continued)

(56) References Cited

U.S. PATENT DOCUMENTS 4,976,711 A 12/1990 Parins et al.
4,998,933 A 3/1991 Eggers et al.
(Continued)

FOREIGN PATENT DOCUMENTS

EP 0565796 B1 10/1993
JP 2009520575 A 5/2009
(Continued)

OTHER PUBLICATIONS

International Search Report and Written Opinion dated Aug. 17, 2020 in corresponding International Patent Application No. PCT/US2020/034686 (9 pages).

*Primary Examiner* — Khadijeh A Vahdat
*Assistant Examiner* — Marina Delaney Templeton

(57) ABSTRACT

A device for dividing a fibrous structure comprising an expandable member positioned near the distal end of a catheter and in fluid communication with the lumen of the catheter so that the expandable member can be biased between an inflated state and a deflated state to tension the fibrous structure, and electrosurgical elements situated on or proximate to an outer surface of the expandable member and configured to deliver electrical and thermal energy to the tensioned fibrous structure in a manner that results in division of the tensioned fibrous structure. A method for dividing a fibrous structure comprising positioning proximate the fibrous structure an expandable member having electrosurgical elements, expanding the expandable member outwards to tension the fibrous structure across the electrosurgical elements, and activating the electrosurgical elements to deliver energy to the tensioned fibrous structure to divide the tensioned fibrous structure.

34 Claims, 21 Drawing Sheets

(51) Int. Cl.
  *A61B 18/12* (2006.01)
  *A61B 90/00* (2016.01)
(52) U.S. Cl.
  CPC ............ *A61B 2018/00077* (2013.01); *A61B 2018/00083* (2013.01); *A61B 2018/0022* (2013.01); *A61B 2018/00601* (2013.01); *A61B 2018/0072* (2013.01); *A61B 2018/00755* (2013.01); *A61B 2018/1246* (2013.01); *A61B 2090/376* (2016.02); *A61B 2090/378* (2016.02)
(58) Field of Classification Search
  CPC .......... A61B 2018/00244; A61B 2018/00577; A61B 2018/126; A61B 2018/1497; A61B 2018/00273; A61B 2018/1206; A61B 2018/00083; A61B 2018/00232; A61B 2018/00214; A61B 18/1492; A61B 18/148; A61B 18/14; A61B 90/02; A61B 90/37; A61B 2090/064; A61B 17/32075; A61B 5/6853; A61B 2017/320048; A61B 2017/3486; A61N 1/36017
  See application file for complete search history.

(56) References Cited

U.S. PATENT DOCUMENTS

| | | |
|---|---|---|
| 5,100,425 A | 3/1992 | Fischell et al. |
| 5,196,024 A | 3/1993 | Barath |
| 5,209,799 A | 5/1993 | Vigil |
| 5,273,024 A | 12/1993 | Menon |
| 5,320,634 A * | 6/1994 | Vigil .............. A61B 17/320725 604/103.08 |
| 5,336,234 A | 8/1994 | Vigil et al. |
| 5,344,398 A | 9/1994 | Hara |
| 5,540,681 A | 7/1996 | Strul et al. |
| 5,547,469 A | 8/1996 | Rowland et al. |
| 5,573,533 A | 11/1996 | Strul |
| 5,616,149 A | 4/1997 | Barath |
| 5,628,746 A | 5/1997 | Clayman |
| RE35,523 E | 6/1997 | Berger |
| 5,697,944 A | 12/1997 | Lary |
| 5,700,243 A | 12/1997 | Narciso, Jr. |
| 5,713,913 A | 2/1998 | Lary et al. |
| 5,769,865 A | 6/1998 | Kermode |
| 5,792,158 A | 8/1998 | Lary |
| 5,797,935 A | 8/1998 | Barath |
| 5,904,679 A | 5/1999 | Clayman |
| 5,908,433 A | 6/1999 | Eager |
| 6,024,740 A | 2/2000 | Lesh et al. |
| 6,033,397 A | 3/2000 | Laufer et al. |
| 6,036,689 A | 3/2000 | Tu et al. |
| 6,036,713 A | 3/2000 | Kieturakis |
| 6,041,260 A | 3/2000 | Stern et al. |
| 6,080,102 A | 6/2000 | Konou et al. |
| 6,117,153 A | 9/2000 | Lary et al. |
| 6,165,187 A | 12/2000 | Reger |
| 6,190,355 B1 | 2/2001 | Hastings |
| 6,193,653 B1 | 2/2001 | Evans et al. |
| 6,214,024 B1 | 4/2001 | Houser et al. |
| 6,231,572 B1 | 5/2001 | Hart et al. |
| 6,245,026 B1 | 6/2001 | Campbell et al. |
| 6,258,108 B1 | 7/2001 | Lary |
| 6,306,151 B1 | 10/2001 | Lary |
| 6,319,242 B1 | 11/2001 | Patterson et al. |
| 6,405,732 B1 | 6/2002 | Edwards et al. |
| 6,405,733 B1 | 6/2002 | Fogarty et al. |
| 6,423,058 B1 | 7/2002 | Edwards et al. |
| 6,425,877 B1 | 7/2002 | Edwards |
| 6,440,128 B1 | 8/2002 | Edwards et al. |
| 6,443,924 B1 | 9/2002 | Rowland et al. |
| 6,443,927 B1 | 9/2002 | Cook |
| 6,464,697 B1 | 10/2002 | Edwards et al. |
| 6,488,679 B1 | 12/2002 | Swanson et al. |
| 6,500,186 B2 | 12/2002 | Lafontaine et al. |
| 6,562,062 B2 | 5/2003 | Jenusaitis et al. |
| 6,632,231 B2 | 10/2003 | Radisch, Jr. |
| 6,673,066 B2 | 1/2004 | Werneth |
| 6,746,463 B1 | 6/2004 | Schwartz |
| 6,936,047 B2 | 8/2005 | Nasab et al. |
| 6,942,680 B2 | 9/2005 | Grayzel et al. |
| 6,951,566 B2 | 10/2005 | Lary |
| 6,971,395 B2 | 12/2005 | Edwards et al. |
| 7,008,438 B2 | 3/2006 | O'Brien |
| 7,011,670 B2 | 3/2006 | Radisch, Jr. |
| 7,018,391 B2 | 3/2006 | Spitz et al. |
| 7,029,450 B2 | 4/2006 | Gellman |
| 7,029,483 B2 | 4/2006 | Schwartz |
| 7,070,576 B2 * | 7/2006 | O'Brien .......... A61B 17/320725 604/96.01 |
| 7,153,315 B2 | 12/2006 | Miller |
| 7,172,609 B2 | 2/2007 | Radisch, Jr. |
| 7,186,237 B2 | 3/2007 | Meyer et al. |
| 7,270,673 B2 | 9/2007 | Yee et al. |
| 7,279,002 B2 | 10/2007 | Shaw et al. |
| 7,291,158 B2 | 11/2007 | Crow et al. |
| 7,303,572 B2 | 12/2007 | Melsheimer et al. |
| 7,338,463 B2 | 3/2008 | Vigil |
| 7,344,535 B2 | 3/2008 | Stern et al. |
| 7,396,358 B2 | 7/2008 | Appling et al. |
| 7,413,558 B2 | 8/2008 | Kelley et al. |
| 7,462,179 B2 | 12/2008 | Edwards et al. |
| 7,494,497 B2 | 2/2009 | Weber |
| 7,517,352 B2 | 4/2009 | Evans et al. |
| 7,530,979 B2 | 5/2009 | Ganz et al. |
| 7,611,482 B2 | 11/2009 | Naimark et al. |
| 7,632,288 B2 | 12/2009 | Wu |
| 7,641,633 B2 | 1/2010 | Laufer et al. |
| 7,648,500 B2 | 1/2010 | Edwards et al. |
| 7,658,744 B2 | 2/2010 | Jackson |
| 7,662,163 B2 | 2/2010 | Grayzel et al. |
| 7,691,116 B2 | 4/2010 | Goodin et al. |
| 7,736,375 B2 | 6/2010 | Crow |
| 7,753,907 B2 | 7/2010 | DiMatteo et al. |
| 7,754,047 B2 | 7/2010 | Kelley |
| 7,758,604 B2 | 7/2010 | Wu et al. |
| 7,771,447 B2 | 8/2010 | Kunis |
| 7,780,626 B2 | 8/2010 | Wu et al. |
| 7,799,043 B2 | 9/2010 | O'Brien et al. |
| 7,879,053 B2 | 2/2011 | Trinidad |
| 7,887,557 B2 | 2/2011 | Kelley et al. |
| 7,901,402 B2 | 3/2011 | Jones et al. |
| 7,959,627 B2 | 6/2011 | Utley et al. |
| 7,976,557 B2 | 7/2011 | Kunis |
| 7,985,234 B2 | 7/2011 | Wang et al. |
| 7,993,358 B2 | 8/2011 | O'Brien |
| 8,034,066 B2 | 10/2011 | Goeken et al. |
| 8,038,691 B2 | 10/2011 | Bence et al. |
| 8,043,259 B2 | 10/2011 | Radisch, Jr. et al. |
| 8,043,311 B2 | 10/2011 | Radisch, Jr. et al. |
| 8,048,093 B2 | 11/2011 | Mapes et al. |
| 8,052,701 B1 | 11/2011 | Cox et al. |
| 8,052,703 B2 | 11/2011 | St. Martin et al. |
| 8,066,726 B2 | 11/2011 | Kelley |
| 8,109,951 B2 | 2/2012 | Maschke |
| 8,123,770 B2 | 2/2012 | Olsen et al. |
| 8,142,422 B2 | 3/2012 | Makower et al. |
| 8,202,285 B2 | 6/2012 | Goodin et al. |
| 8,361,096 B2 | 1/2013 | Bence et al. |
| 8,364,237 B2 | 1/2013 | Stone et al. |
| 8,377,055 B2 | 2/2013 | Jackson et al. |
| 8,377,083 B2 | 2/2013 | Mauch et al. |
| 8,401,667 B2 | 3/2013 | Gustus et al. |
| 8,412,318 B2 | 4/2013 | Edwards et al. |
| 8,439,908 B2 | 5/2013 | Utley et al. |
| 8,454,636 B2 | 6/2013 | Konstantino et al. |
| 8,454,637 B2 | 6/2013 | Aggerholm et al. |
| 8,491,615 B2 | 7/2013 | Manderfeld et al. |
| 8,496,653 B2 | 7/2013 | Steinke |
| 8,523,887 B2 | 9/2013 | Grayzel et al. |
| 8,568,416 B2 | 10/2013 | Schmitz et al. |
| 8,641,709 B2 | 2/2014 | Sauvageau et al. |
| 8,679,141 B2 | 3/2014 | Goodin et al. |
| 8,685,049 B2 | 4/2014 | Schur et al. |

(56) References Cited

U.S. PATENT DOCUMENTS

| | | | |
|---|---|---|---|
| 8,690,903 B2 | 4/2014 | Bence et al. | |
| 8,702,736 B2 | 4/2014 | Schur et al. | |
| 8,721,636 B2 | 5/2014 | Vaska et al. | |
| 8,740,846 B2 | 6/2014 | Edwards et al. | |
| 8,740,896 B2 | 6/2014 | Zarins et al. | |
| 8,774,922 B2 | 7/2014 | Zarins et al. | |
| 8,818,514 B2 | 8/2014 | Zarins et al. | |
| 8,855,778 B2 | 10/2014 | Rezai | |
| 8,870,816 B2 | 10/2014 | Chambers et al. | |
| 8,906,049 B2 | 12/2014 | Chambers | |
| 8,920,414 B2 | 12/2014 | Stone et al. | |
| 8,939,970 B2 | 1/2015 | Stone et al. | |
| 8,945,168 B2 | 2/2015 | Davies et al. | |
| 8,951,251 B2 | 2/2015 | Willard | |
| 8,958,871 B2 | 2/2015 | Demarais et al. | |
| 8,986,248 B2 | 3/2015 | Kunis | |
| 9,017,343 B2 | 4/2015 | Westerling et al. | |
| 9,017,353 B2 | 4/2015 | Bence et al. | |
| 9,649,153 B2 | 5/2017 | Mayse et al. | |
| 9,974,607 B2 | 5/2018 | Stone et al. | |
| 10,335,189 B2 | 7/2019 | Aklog et al. | |
| 10,357,272 B2 | 7/2019 | Barnes et al. | |
| 10,413,346 B2 | 9/2019 | Wallace | |
| 10,864,055 B2 | 12/2020 | Barnes et al. | |
| 11,141,186 B2 | 10/2021 | Aklog et al. | |
| 11,259,837 B2 | 3/2022 | Aklog et al. | |
| 2002/0082592 A1 | 6/2002 | Lary | |
| 2003/0144683 A1 | 7/2003 | Sirhan et al. | |
| 2004/0098014 A1 | 5/2004 | Flugelman et al. | |
| 2005/0070888 A1 | 3/2005 | Dimatteo et al. | |
| 2005/0177130 A1 | 8/2005 | Konstantino et al. | |
| 2005/0240148 A1 | 10/2005 | Cheves et al. | |
| 2006/0116700 A1 | 6/2006 | Crow | |
| 2006/0178685 A1 | 8/2006 | Melsheimer | |
| 2006/0184191 A1 | 8/2006 | O'Brien | |
| 2006/0247611 A1* | 11/2006 | Abboud | A61B 18/02 606/23 |
| 2006/0276782 A1 | 12/2006 | Gedebou | |
| 2007/0198047 A1 | 8/2007 | Schon et al. | |
| 2007/0213761 A1 | 9/2007 | Murphy et al. | |
| 2007/0265617 A1* | 11/2007 | Falkenstein | A61B 18/1492 606/48 |
| 2008/0077164 A1 | 3/2008 | Murphy | |
| 2008/0077165 A1 | 3/2008 | Murphy | |
| 2008/0300610 A1 | 12/2008 | Chambers | |
| 2009/0270892 A1 | 10/2009 | Arcenio et al. | |
| 2010/0010521 A1 | 1/2010 | Kurrus | |
| 2010/0125266 A1* | 5/2010 | Deem | A61B 17/320036 606/192 |
| 2010/0168611 A1 | 7/2010 | Hashimshony et al. | |
| 2010/0204560 A1 | 8/2010 | Salahieh et al. | |
| 2010/0241148 A1 | 9/2010 | Schon et al. | |
| 2010/0274271 A1 | 10/2010 | Kelley | |
| 2010/0286594 A1 | 11/2010 | Chambers | |
| 2010/0312264 A1 | 12/2010 | O'Brien et al. | |
| 2011/0119601 A1 | 5/2011 | Knothe et al. | |
| 2011/0160756 A1 | 6/2011 | Aggerholm et al. | |
| 2011/0301625 A1 | 12/2011 | Mauch et al. | |
| 2011/0306996 A1* | 12/2011 | McCormack | A61B 17/320036 606/170 |
| 2012/0022532 A1 | 1/2012 | Garrison | |
| 2012/0022563 A1 | 1/2012 | Leffel | |
| 2012/0191112 A1 | 7/2012 | Zamboni | |
| 2012/0215251 A1 | 8/2012 | Burton et al. | |
| 2012/0316589 A1 | 12/2012 | Schaeffer | |
| 2013/0018396 A1 | 1/2013 | Gunderson et al. | |
| 2013/0023912 A1 | 1/2013 | Brown et al. | |
| 2013/0053851 A1 | 2/2013 | Schmitz et al. | |
| 2013/0060127 A1 | 3/2013 | Burton et al. | |
| 2013/0066257 A1 | 3/2013 | Folan et al. | |
| 2013/0066346 A1 | 3/2013 | Pigott | |
| 2013/0072815 A1 | 3/2013 | Hashimshony et al. | |
| 2013/0085493 A1* | 4/2013 | Bloom | A61B 18/1492 606/41 |
| 2013/0090649 A1* | 4/2013 | Smith | A61B 18/1492 606/41 |
| 2013/0131709 A1 | 5/2013 | Davies et al. | |
| 2013/0131770 A1 | 5/2013 | Rezai | |
| 2013/0144318 A1 | 6/2013 | Carmo | |
| 2013/0165916 A1 | 6/2013 | Mathur et al. | |
| 2013/0165962 A1 | 6/2013 | Porshinsky et al. | |
| 2013/0296647 A1 | 11/2013 | Mayse et al. | |
| 2014/0088624 A1 | 3/2014 | Burton et al. | |
| 2014/0128895 A1 | 5/2014 | Bence et al. | |
| 2014/0155920 A1 | 6/2014 | Schur et al. | |
| 2014/0163593 A1 | 6/2014 | Schur et al. | |
| 2014/0180196 A1 | 6/2014 | Stone et al. | |
| 2014/0277002 A1 | 9/2014 | Grace | |
| 2014/0277059 A1 | 9/2014 | Lam et al. | |
| 2014/0296888 A1 | 10/2014 | Schur et al. | |
| 2014/0303617 A1 | 10/2014 | Shimada | |
| 2016/0157880 A1* | 6/2016 | Aklog | A61B 90/30 606/45 |
| 2016/0331459 A1* | 11/2016 | Townley | A61N 1/0546 |
| 2018/0228538 A1* | 8/2018 | Roeder | A61B 18/1492 |
| 2018/0271552 A1 | 9/2018 | Aklog et al. | |
| 2021/0059759 A1 | 3/2021 | Asirvatham et al. | |
| 2021/0069465 A1 | 3/2021 | Daniels et al. | |
| 2021/0369337 A1 | 12/2021 | Aklog et al. | |
| 2022/0000513 A1 | 1/2022 | Aklog et al. | |
| 2022/0022910 A1 | 1/2022 | Aklog et al. | |

FOREIGN PATENT DOCUMENTS

| | | |
|---|---|---|
| JP | 2013534166 A | 8/2015 |
| JP | 6815998 B2 | 1/2021 |
| WO | 1998033445 A1 | 12/1998 |
| WO | 2007075986 A2 | 7/2007 |
| WO | 2012023006 A1 | 2/2012 |
| WO | 201690175 | 6/2016 |
| WO | 2016090122 A1 | 6/2016 |

* cited by examiner

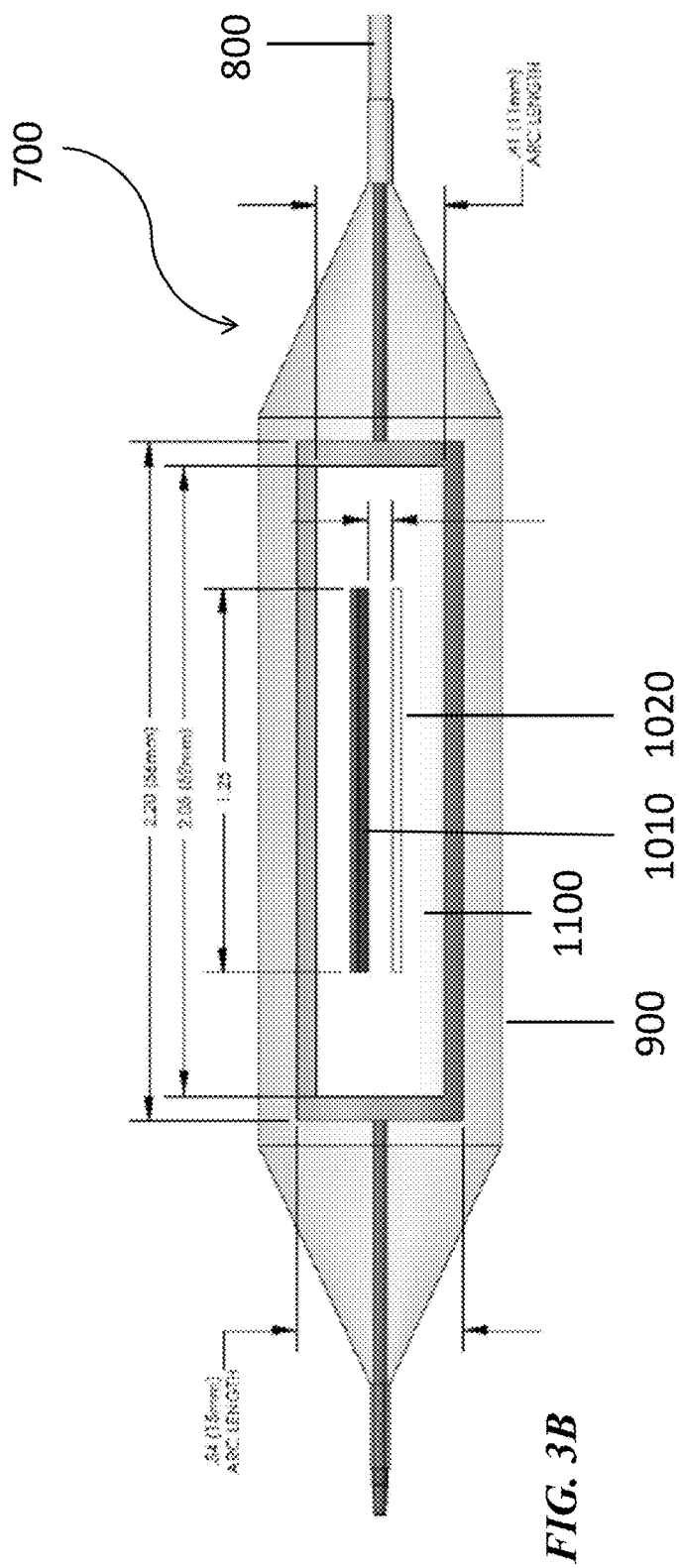
FIG. 3B
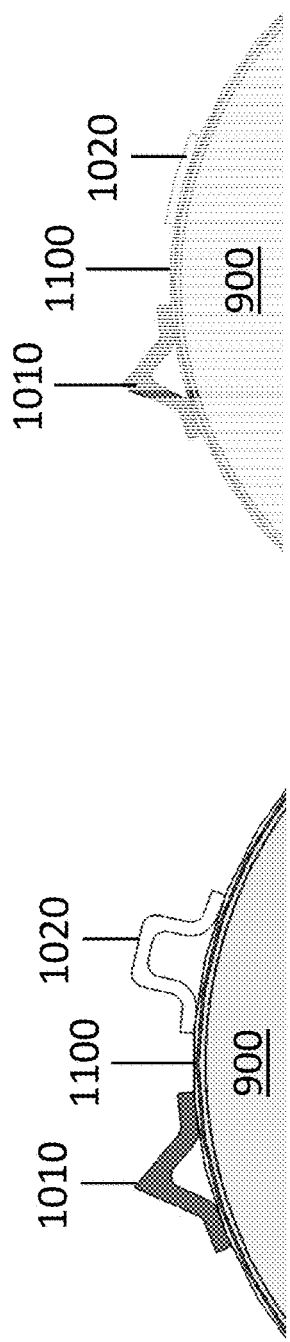
FIG. 3C
FIG. 3D

SYSTEMS AND METHODS FOR MINIMALLY-INVASIVE DIVISION OF FIBROUS STRUCTURES

BACKGROUND

The body contains a variety of anatomic compartments with one or more fibrous walls. In certain pathologic situations, the structures within the compartment can be compressed either by swelling or inflammation of the structures or constriction by the compartment walls. For example, compression of blood vessels or nerves passing through the compartment can lead to poor blood flow or loss of neurologic (sensory or motor) function in the tissues within or beyond the compartment. Examples of such conditions include carpal tunnel syndrome, plantar fasciitis, fascial compartment syndrome and abdominal compartment syndrome. The treatment of these conditions will often involve cutting one or more fibrous walls to release pressure on the compartment's anatomic structures. This usually requires open surgery either with direct or endoscopic vision. Few if any minimally-invasive options exist for these conditions.

Carpal tunnel syndrome (CTS) is the most common cumulative trauma disorder (CTD's) which collectively account for over half of all occupational injuries. It exacts a major economic burden on society including billions in lost wages and productivity. The carpal tunnel is located in the wrist. It's bounded by the carpal bones posteriorly, laterally and medially and by the transverse carpal ligament anteriorly. The flexor tendons and the median nerve pass through the carpal tunnel. Cumulative trauma leads to inflammation within tunnel and manifests itself clinically through its compressive effect on the median nerve resulting in motor and sensory dysfunction in the hand. The diagnosis is usually confirmed with nerve conduction tests. Traditional surgical approaches are effective but invasive and have to be performed in a surgical operating room. An incision is made in the palm or over the wrist. The transverse carpal ligament is surgically exposed and divided with scissors or a scalpel. Endoscopic approaches are less invasive but more technically challenging, have been associated with a higher complication rate and are more expensive. They still require a 1 cm surgical incision and some initial surgical dissection before the endoscope is passed into the carpal tunnel. One device attempts to use a transillumination to guide blind passage of a protected knife. Another device passes a saw-like cutting device into the carpal tunnel blindly or by ultrasound guidance.

It is therefore desirable to have a minimally-invasive approach to treat carpal tunnel syndrome that is less invasive than existing approaches and that results in less trauma and quicker recovery times for the patient.

SUMMARY

In accordance with example embodiments of the present invention, a device for dividing a fibrous structure is provided. The device includes a catheter having a proximal end, a distal end, and lumen extending therebetween, an expandable member positioned towards the distal end of the catheter and in fluid communication with the lumen of the catheter so that the expandable member can be biased between an inflated state and a deflated state to tension the fibrous structure, and electrosurgical elements configured to deliver electrical energy to the fibrous structure tensioned along the expandable member in a manner that results in division of the tensioned fibrous structure.

In accordance with aspects of the present invention, the expandable member is a balloon. The electrosurgical elements can be sesquipolar. At least a portion of the expandable member can have a non-circular or asymmetrical cross-sectional shape. A distal portion of the expandable member can include a shaped profile having a larger diameter than that of a proximal portion of the expandable member, and the shaped profile of the distal portion of the expandable member can be configured to engage anatomy beyond the fibrous structure to minimize migration of the device during division. The expandable member can have an elongated longitudinal profile. The expandable member can be configured to contact the fibrous structure and expand outwards to tension the fibrous structure across the electrosurgical elements.

In accordance with aspects of the present invention, the electrosurgical elements are situated along a longitudinal dimension of the device, and the expandable member can expand radially so as to tension the fibrous structure in a direction substantially transverse to the electrosurgical elements. The electrosurgical leads can include an active lead and a passive lead, and the active lead can concentrate the electrical energy such that division of the fibrous tissue occurs along a portion of the tensioned fibrous tissue in contact with the active lead. The active lead can have a substantially pointed leading edge. At least a portion of the active lead, excluding the pointed leading edge, can be covered by an insulating material such that delivery of the electrical and thermal energy can be concentrated at the pointed leading edge of the active lead. The passive lead can protrude above a surface of the device on which it is mounted so as to contact and further tension the fibrous structure. The electrosurgical elements can be situated on an outer surface of the catheter. The device can further include an insulating member positioned between the electrosurgical elements and the outer surface of the catheter. The insulating member can be rigid or semi-rigid and couples with the catheter above the expandable member. The insulating member can include grooves in which the electrosurgical leads are mounted, and at least an active lead can protrude beyond an upper surface of the insulating member.

In accordance with aspects of the present invention, the electrosurgical elements are situated on an outer surface of the expandable member. The device can further include an insulating member positioned between the electrosurgical elements and the outer surface of the catheter. The insulating member is a flexible film coupled with an outer surface of the expandable member. A longitudinal axis of the expandable member is substantially coaxial with a longitudinal axis of the catheter. The a longitudinal axis of the expandable member is offset from a longitudinal axis of the catheter. The device can further include a sensor for measuring at least one of an internal pressure of the expandable member, an external force applied to the expandable member, impedance in the electrosurgical circuit, and current in the electrosurgical circuit. The device can further include a processor for monitoring the measurements to detect a threshold measurement or change indicative of complete division of the fibrous structure. The device can further include a protective jacket for use during insertion of the device.

In accordance with aspects of the present invention, the device further includes nerve stimulation electrosurgical elements configured to deliver electrical and thermal energy to detect presence of a motor nerve or a sensing nerve proximal to the electrosurgical elements. The nerve stimulation electrosurgical elements can include an input electrode and an output electrode for measuring an electrical response between the input electrode and the output electrode. The nerve stimulation electrosurgical elements can be connected to a measurement circuit to detect a change in energy over the input electrode and the output electrode. The nerve stimulation electrosurgical elements can be connected to a separate generator than the electrosurgical elements. The device can further include a jacket situated around the expandable member and the electrosurgical elements to assists in placement of the distal end of the catheter within a location containing the fibrous structure. The device can further include a dilator with a tapered tip for insertion into an insertion site and for receiving the jacket for positioning the jacket within the location containing the fibrous structure. The device can further include a guidewire for positioning at least one of the dilator and the jacket within the location containing the fibrous structure. The jacket can be one of a flexible material or a rigid material with sufficient structure to maintain a pathway for receiving the distal end of the catheter including the expandable member and the electrosurgical elements of the device. The jacket can be removeable from the distal end of the catheter including the expandable member and the electrosurgical elements at least distally away from the device or proximally toward the device. The jacket can have a tapered to assist in placement within an incision site. The jacket can be removable in a plurality of pieces.

In accordance with example embodiments of the present invention, a method for dividing a fibrous structure is provided. The method includes positioning, proximate the fibrous structure, a device having an expandable member and electrosurgical elements, expanding the expandable member outwards to tension the fibrous structure across the electrosurgical elements, and activating the electrosurgical elements to deliver electrical energy to the tensioned fibrous structure in a manner that results in division of the tensioned fibrous structure.

In accordance with aspects of the present invention, the step of positioning includes orienting the electrosurgical elements to face the fibrous structure. The method can further include orienting the electrosurgical elements in a direction substantially transverse to the fibrous structure. The step of positioning further includes positioning, beyond the fibrous structure, a portion of the expandable member can have a shaped profile with a larger diameter than that of a proximal portion of the expandable member and in the step of expanding, the shaped profile of the distal portion of the expandable member can engage the anatomy beyond the fibrous structure to minimize migration of the device during division. The step of expanding the expandable member can further serves to manipulate a position of an anatomical structure located near the expandable member.

In accordance with aspects of the present invention, step of activating can include delivering the electrical and thermal energy as a short pulse having a duration of about 1 second to about 3 seconds. In accordance with aspects of the present invention, step of activating can include delivering the electrical and thermal energy with about 20 W to about 100 W, preferably 20 W to 30 W. In accordance with aspects of the present invention, step of activating can include delivering the electrical and thermal energy as a short pulse having a duration of about 1 second to about 3 seconds and with about 20 W to about 100 W, preferably 20 W to 60 W. In accordance with aspects of the present invention, step of activating can include monitoring an internal pressure in the expandable member to detect a change in pressure indicative of complete division of the fibrous structure.

In accordance with aspects of the present invention, the step of activating can include monitoring an external force applied to the expandable member to detect a change in force indicative of complete division of the fibrous structure. The step of activating can include monitoring an impedance of the electrosurgical circuit to detect when the impedance reaches a threshold level indicative of complete division of the fibrous structure. The step of activating can include monitoring an impedance of the electrosurgical circuit to detect a time rate of change in the impedance measurements indicative of complete division of the fibrous structure. The step of activating can include monitoring a current in the electrosurgical circuit to detect a reduction in current indicative of complete division of the fibrous structure. The method can further include the step of visualizing, via fluoroscopy or ultrasound, a shape of the expandable member to detect when a deformation in the expandable member, created by force applied to the expandable member by the fibrous structure, disappears, thereby indicating a complete division of the fibrous structure. The step of activating can include delivering the electrical and thermal energy approximately from about 1 W to about 2 W to stimulate any nerves proximal to the electrosurgical elements. The method can further include repositioning the device in response to an observation of twitching in response to the delivery of the electrical and thermal energy to the electrosurgical elements.

In accordance with aspects of the present invention, the method can further include activating nerve stimulation electrosurgical elements to deliver electrical and thermal energy approximately from about 1 W to about 2 W to stimulate any nerves proximal to the nerve stimulation electrosurgical elements. The method can further include measuring an electrical response to the electrical and thermal energy delivered to the nerve stimulation electrosurgical elements. The method can further include repositioning the device in response to a change in the measured electrical response in response to the delivery of the electrical and thermal energy with to the nerve stimulation electrosurgical elements. The electrosurgical elements can be automatically disabled in response to a change in the measured electrical response in response to the delivery of the electrical and thermal energy with to the nerve stimulation electrosurgical elements. The positioning the device proximate the fibrous structure can include creating an incision site, inserting a jacket into the incision site, inserting the distal end of the catheter including the expandable member and the electrosurgical elements into the jacket, and removing the jacket from the incision site. The method can further include inserting a guidewire into the incision site. The method can further include inserting a dilator into the incision site.

In accordance with example embodiments of the present invention, a method for division a fibrous structure is provided. The method includes inflating the expandable member of a cutting device outwardly to tension the fibrous structure, visually confirming a waisting of the expandable member against the fibrous structure, and activating the cutting device for dividing the fibrous structure a manner that results in division of the tensioned fibrous structure.

In accordance with aspects of the present invention, the method can further include visually confirming a normalization of the shape of the expandable member to confirm the division. The visually confirming can include at least one of fluoroscopic, ultrasonic, endoscopic visual confirmation.

DESCRIPTION OF THE DRAWINGS

These and other characteristics of the present invention will be more fully understood by reference to the following detailed description in conjunction with the attached drawings, in which:

FIG. 3B depicts a top view of the device of FIG. 3A for minimally-invasive division of fibrous structures, in accordance with another embodiment of the present disclosure;

FIGS. 3C and 3D depict electrosurgical lead configurations of a device for minimally-invasive division of fibrous structures, in accordance with another embodiment of the present disclosure;

DETAILED DESCRIPTION

The present disclosure is directed to a medical device, and in particular, devices for minimally-invasive division of fibrous structures. The medical device, in some embodiments, may be designed to provide a minimally invasively isolate, cut, incise, divide, etc. tendons, ligaments, facias, etc. in confined spaces during a minimally invasive procedure. In an example embodiment, the present disclosure may, from time to time, refer to the treatment of carpal tunnel syndrome as an exemplary application. The carpal tunnel is an anatomic compartment in the wrist bounded by the carpal bones and the transverse carpal ligament. The clinical symptoms of carpal tunnel syndrome primarily arise from compression of the median nerve as it passes through the tunnel. Surgical division of the transverse carpal ligament relieves the compression of the median nerve and its associated symptoms. Although the present disclosure may refer to examples for use within the carpal tunnel to treat carpal tunnel syndrome, the devices and methods described herein may be used for any combination of procedures involving minimally-invasive division of any sort of fibrous structure within or outside the body.

Figures 1A, 1B, 1C:
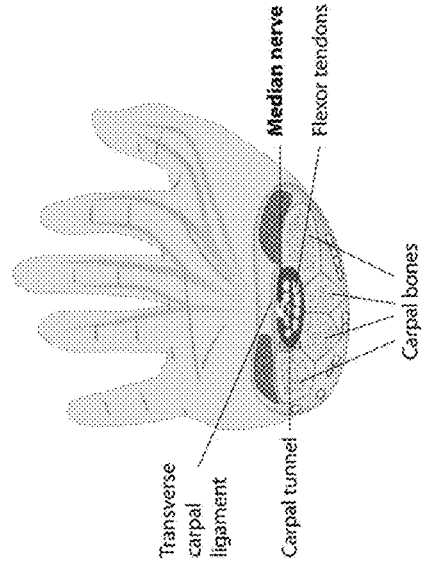
FIGS. 1A, 1B, 1C, 1D, and 1E depict a schematic views of a carpal tunnel of the human body.
Figure 1D:
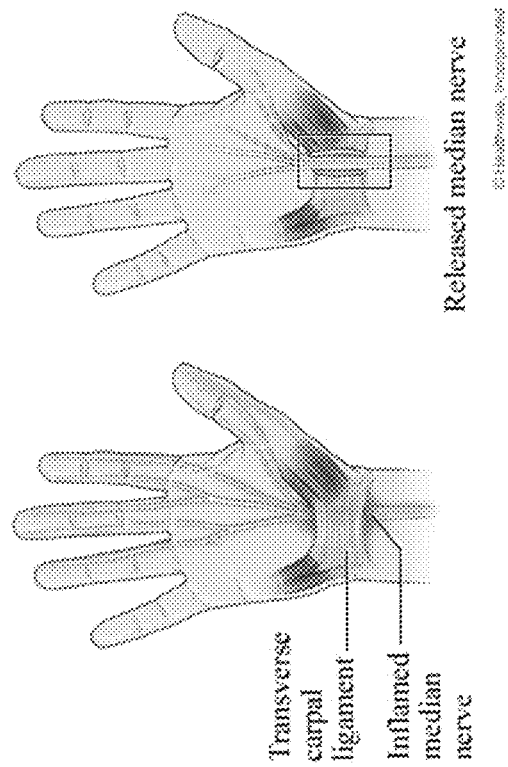
Figure 1E:
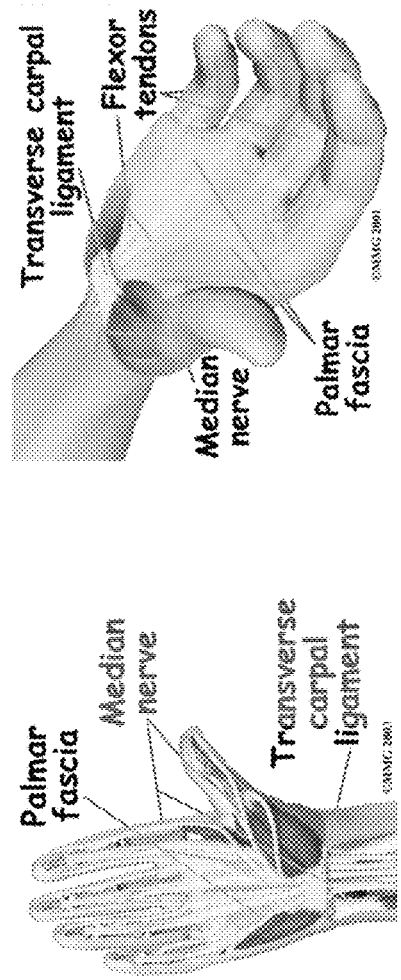
Figure 3A:
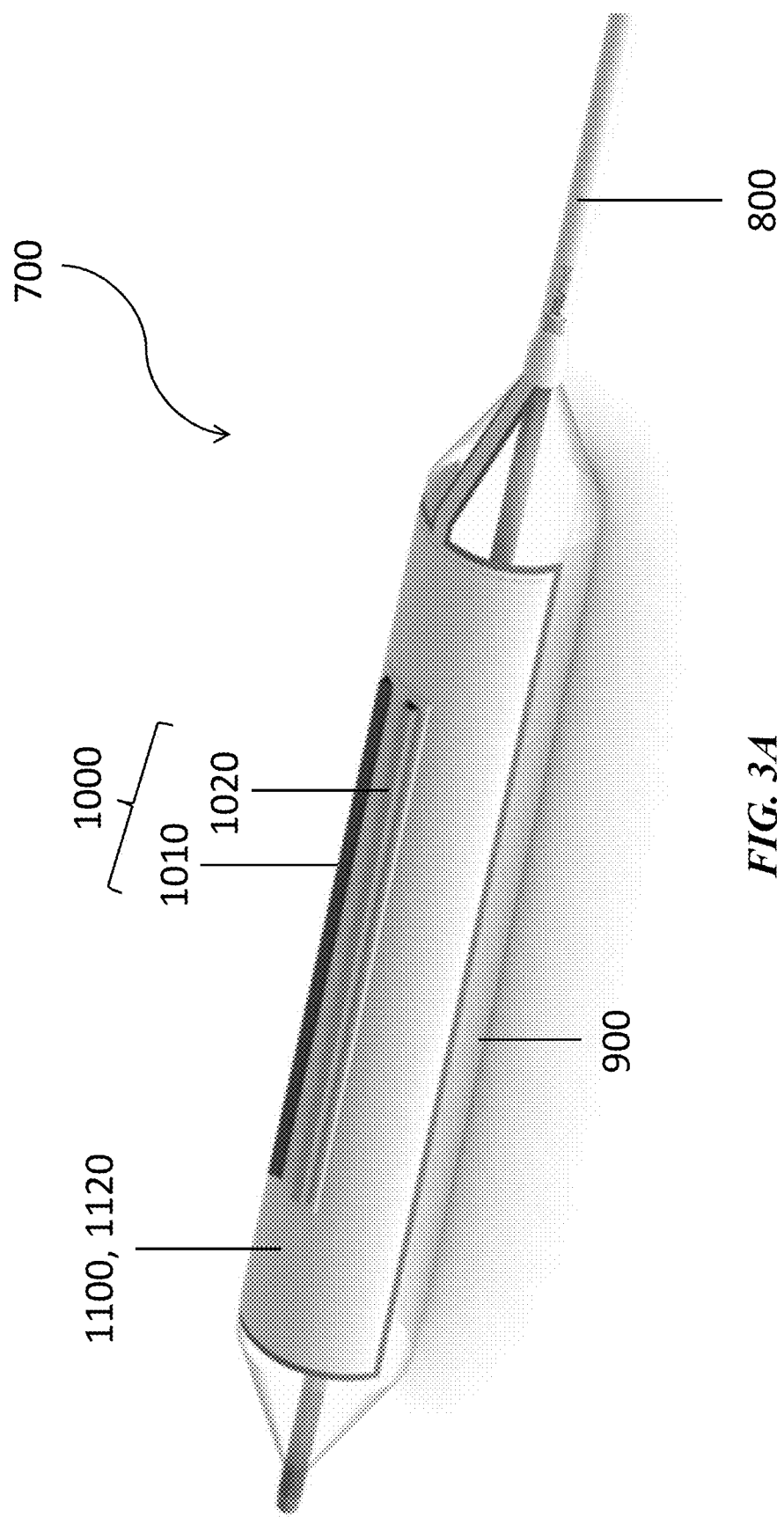
FIG. 3A depicts a device for minimally-invasive division of fibrous structures, in accordance with another embodiment of the present disclosure.
Figure 3E:
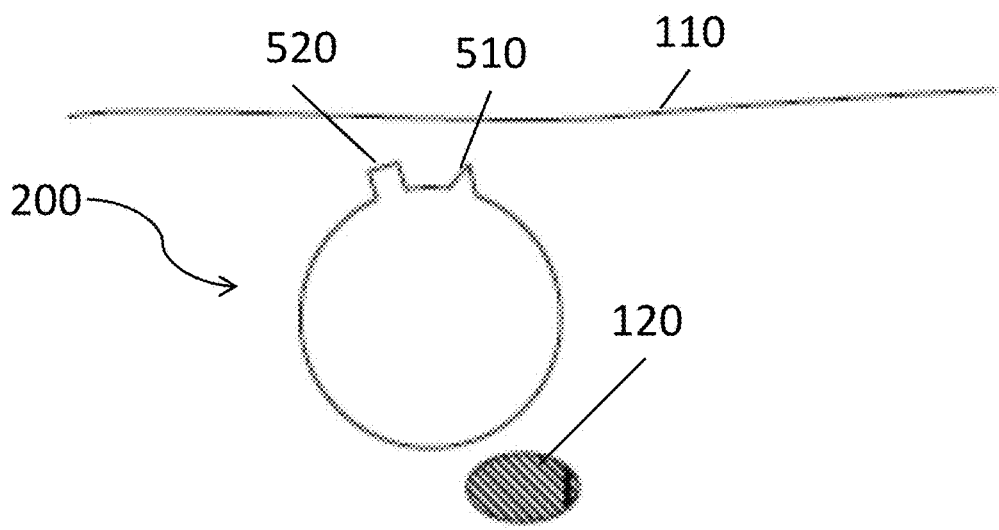
FIGS. 3E, 3F, and 3G depict illustrative cross-sectional end views of the device of FIG. 3B for minimally-invasive division of fibrous structures and nerve sensing, in accordance with an embodiment of the present disclosure.
Figure 3F:
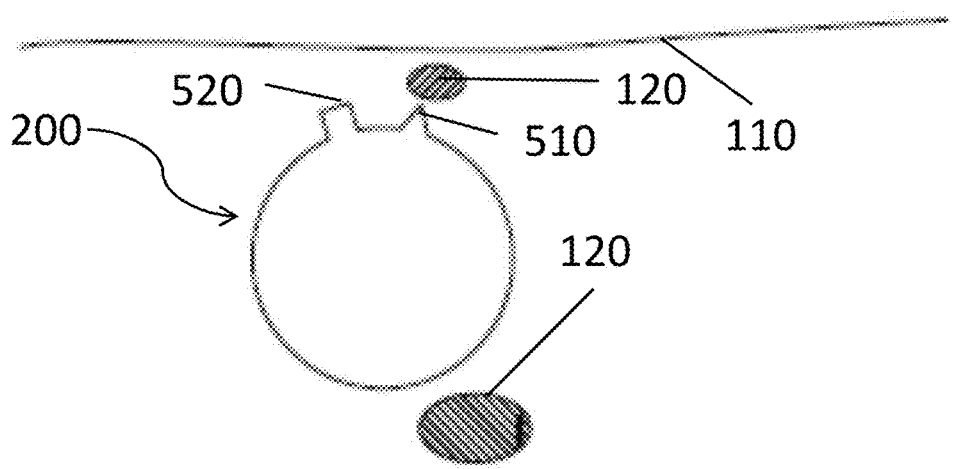
Figure 3G:
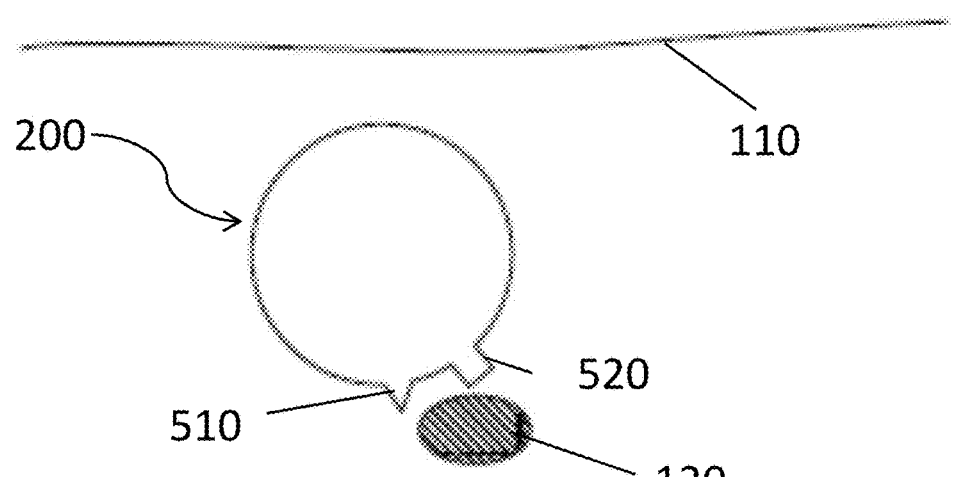
Figure 3H:
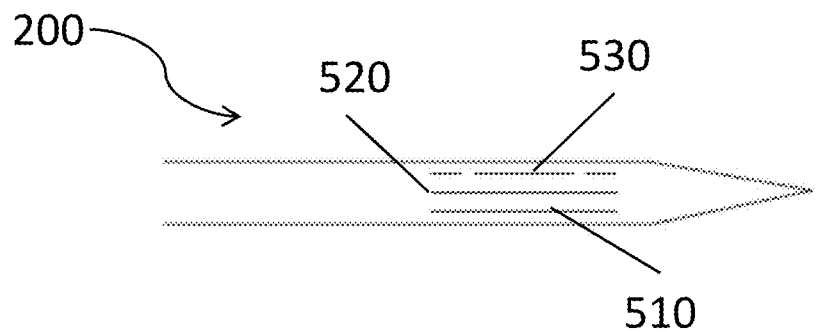
FIG. 3H depicts an illustrative top view of a device for minimally-invasive division of fibrous structures and nerve sensing, in accordance with an embodiment of the present disclosure.
Figure 3I:
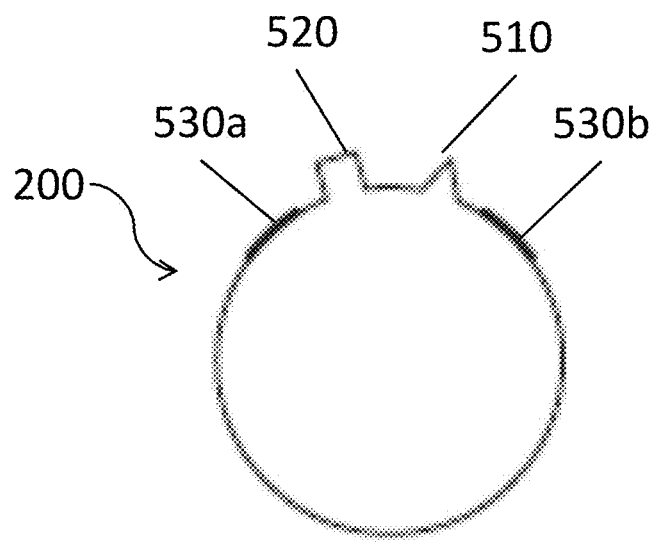
FIG. 3I depicts an illustrative cross-sectional end view of a device for minimally-invasive division of fibrous structures and nerve sensing, in accordance with an embodiment of the present disclosure.
Figure 4A:
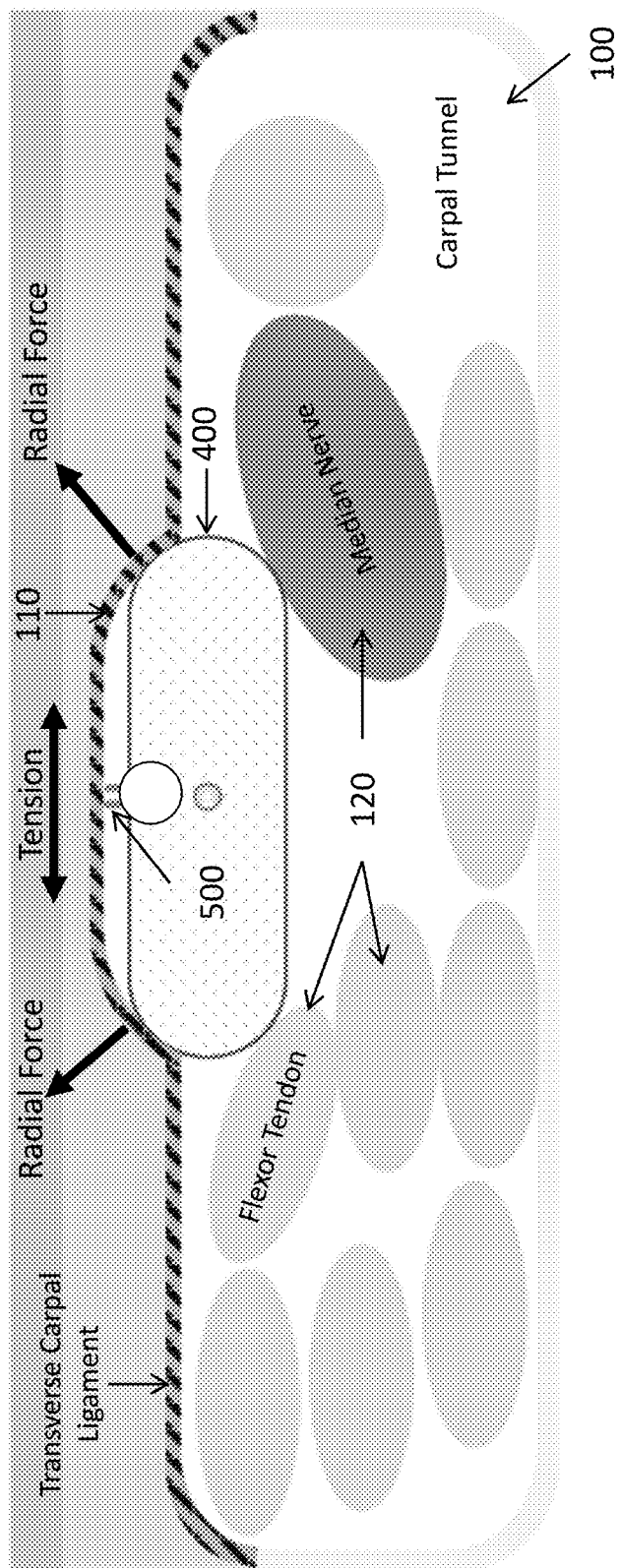
FIG. 4A schematically depicts a device for minimally-invasive division of fibrous structures in an inflated state within a carpal tunnel, in accordance with another embodiment of the present disclosure.
Figure 4B:
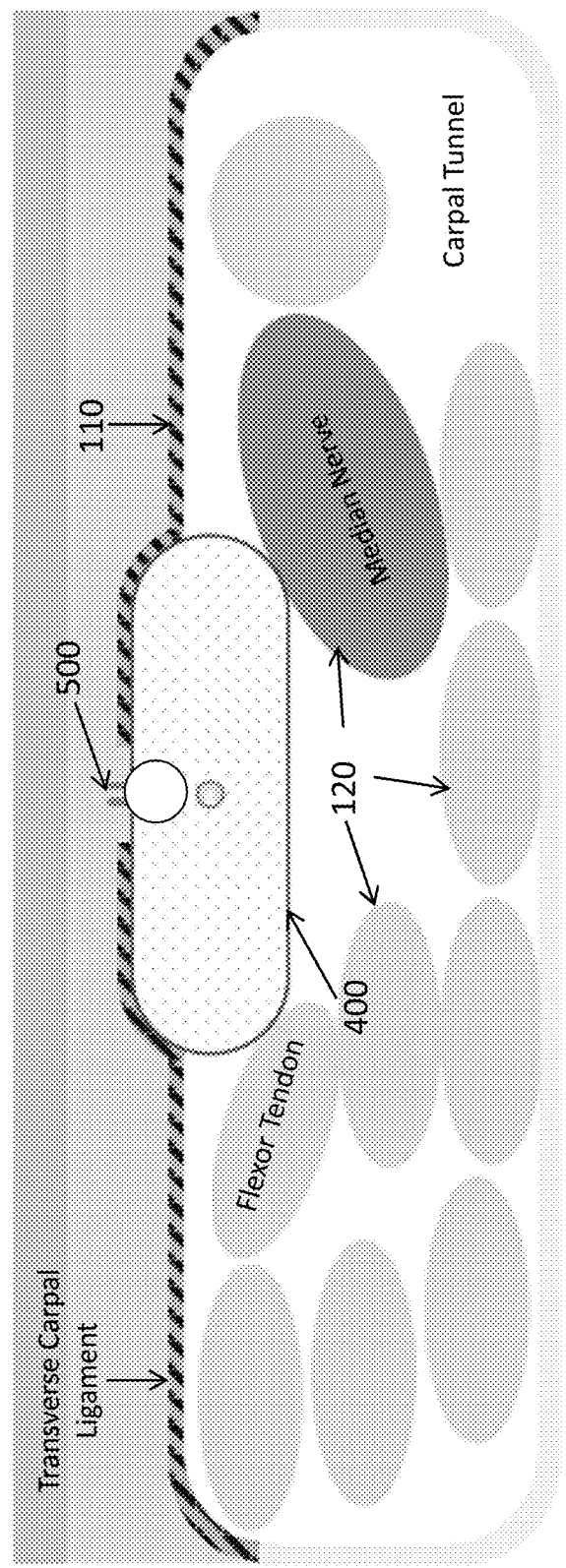
FIG. 4B schematically depicts division of the transverse carpal ligament in the carpal tunnel using the device of FIG. 4A, in accordance with another embodiment of the present disclosure.
Figure 4C:
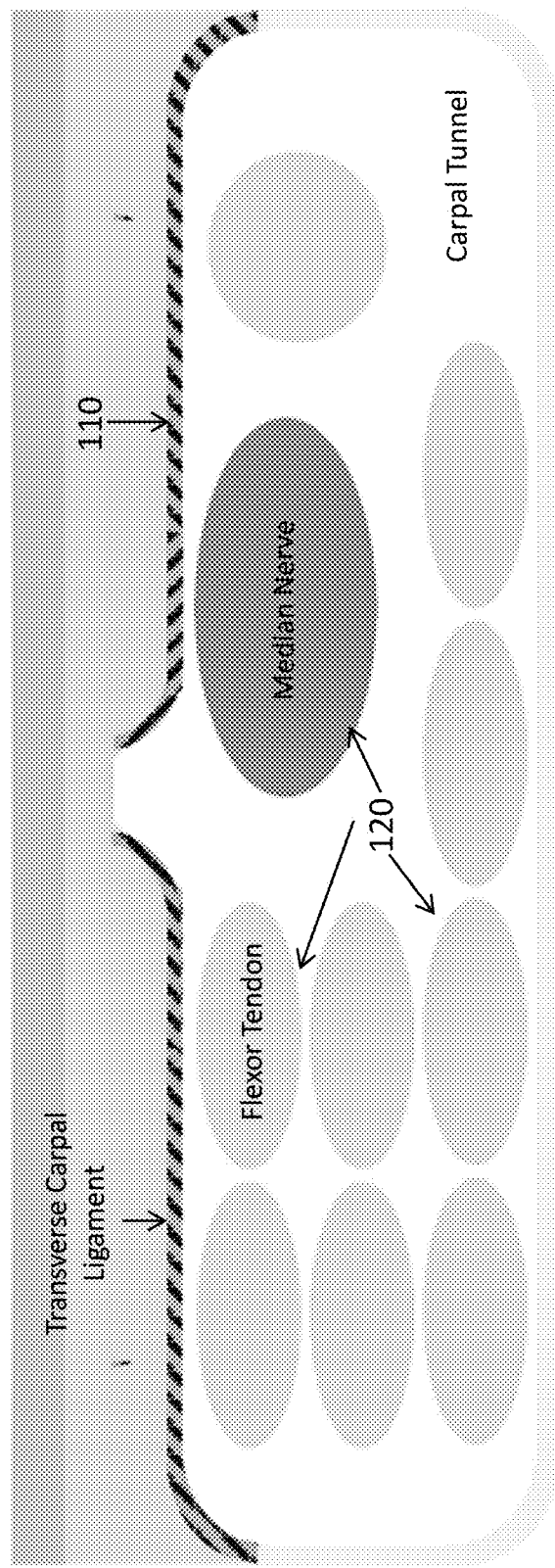
FIG. 4C schematically depicts a carpal tunnel treated with the device of FIG. 4A, in accordance with another embodiment of the present disclosure.

Referring to FIGS. 1A-1E, device 200 as shown in FIGS. 2A-9G, in various embodiments, may be utilized to divide the transverse carpal ligament of the carpal tunnel to relieve pressure on anatomical structures 120 within compartment 100, as shown in FIGS. 4A-4C. The carpal tunnel consists of two rows of carpal (wrist) bones that create the posterior, lateral and medial borders of the tunnel (FIG. 1C). These include, in a clockwise fashion beginning at the 12 o'clock position, the capitate, hamate, pisiform triquetrum, lunate, scaphoid, trapezium and trapezoid bones. The trapezium, trapezoid, capitate and hamate bones comprise the distal carpal row and the distal boundary of the carpal tunnel. The scaphoid, lunate, triquetrum and pisiform comprise the proximal carpal row and the proximal boundary of the carpal tunnel. With regards to the transverse carpal ligament (TCL) that defines the proximal and distal extent of the carpal tunnel, the proximal border is from its attachment to the pisiform extending in the lateral direction to the scaphoid tubercle and the distal border between its attachment from the hook of the hamate extending also in the lateral direction to the tubercle on the trapezium. The carpal tunnel is defined anteriorly by the transverse carpal ligament, which is a double layer membrane of fibrous tissue with attachments medially to the hamate and pisiform bones, and laterally to the trapezium and scaphoid bones. The proximal and distal extent of the carpal tunnel are defined by the vector from the pisiform bone to the scaphoid bone and the hamate bone to the trapezium bones, respectively (FIGS. 1A). The carpal tunnel itself has an hourglass shape both in the anterior-posterior aspect as well as at the medial-lateral aspect, with the narrowest portion (waist) approximately at the junction between the proximal two-thirds of the tunnel and the distal one-third. When repetitive trauma and other pathology cause thickening and inflammation of the transverse carpal ligament, compression of the carpal tunnel structures may occur, including compression of the median nerve and the flexor tendons (FIGS. 1A, 1C, 1D and 1E) which may affect the function of those structures. To relieve compression injury to the median nerve, surgical division of the transverse carpal ligament is often employed (FIG. 1B).

Minimally-Invasive Division Device 200

Referring now to FIGS. 2A-2E, minimally-invasive division device 200 of the present disclosure may generally include a handle 210, catheter 300, a balloon 400 (or other expandable member), one or more electrosurgical elements 500, and an insulating member 600. Although the present invention discusses the use of electrosurgical elements, any combination of elements designed for separation of tissues can be used, for example, electrocautery elements.

As later described in the context of FIGS. 4A-4C, minimally-invasive division device 200 may be inserted into the body and advanced towards an anatomic compartment 100, such as the carpal tunnel, requiring treatment. Once properly positioned within the anatomic compartment, balloon 400 may be expanded to apply a radial force to fibrous wall 110, generating lateral tension along a portion of the fibrous wall 110 of the compartment 100. Electrosurgical elements 500 may be configured to engage the tensioned portion to divide the fibrous wall and thereby decompress the anatomic compartment 100 for therapeutic effect. In some embodiments, the electrosurgical elements 500 can be bipolar radio frequency (RF) elements. To perform electrosurgery using bipolar radio frequency (RF) elements, at least one electrode and one return electrode can be provided in a configuration in which electrical current can travel from a tip of one electrode to the other, with target tissue situated therebetween. As electrical current passes through the target tissue, resistance is provided by the tissue which in turn creates heat that can be used to cut, coagulate, fuse tissue, etc., or a combination thereof to provide the desired therapeutic effect. Any combination of electrosurgical elements 500 can be used, for example, monopolar, bipolar, sesquipolar, etc. without departing from the scope of the present disclosure.

Figure 2A:
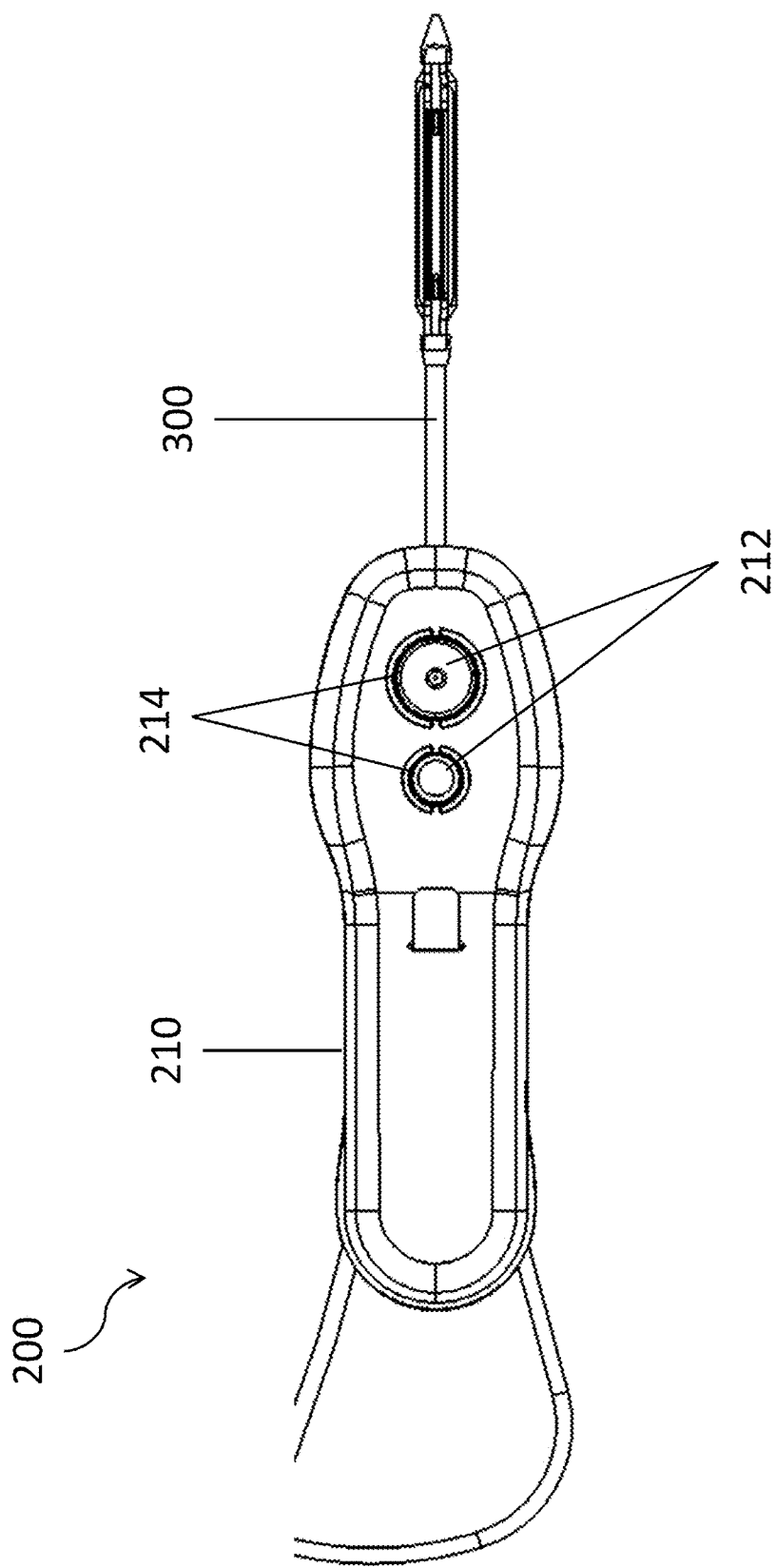
FIG. 2A depicts a handle of a device for minimally-invasive division of fibrous structures, in accordance with an embodiment of the present disclosure.

Referring first to the top view of the representative handle 210 shown in FIG. 2A, a handle 210 may be provided at a proximal end of device 200 and include one or more activation components 212 (e.g., buttons, switches, triggers, touch screens, etc.) for controlling various functionalities of components at a distal end of the device 200. For example, the handle 210 can include a combination of buttons for activating inflation/deflation of balloon 400 and/or activation/deactivation of electrosurgical elements 500 (e.g., application of RF energy). The handle 210, in some embodiments, may include any one or a combination of control features for inflating, deflating, or otherwise controlling expansion and compression of balloon 400 and its internal pressure, as well as features for activating, deactivating, adjusting characteristics of the power delivered by electrosurgical elements 500, such as the power magnitude, frequency, duration, intervals (e.g., pulses), and other relevant characteristics.

In some embodiments, the handle 210 may additionally or alternatively include feedback components 214 for monitoring these characteristics of balloon 400 and of electrosurgical elements 500. For example, the feedback components 214 can be any combination of audio (e.g., speaker), visual (e.g., lighting), or tactile feedback (e.g., vibration generator) components designed to alert the user to a particular state of operation. The handle 210, in some embodiments, may further include feedback features for detecting and alerting a user to the occurrence of key events during the procedure, such as stimulation of the median nerve and complete division of the fibrous wall 110. For example, handle 210 may include feedback components 214 that produce a combination of a visual, audible, or tactile feedback that monitors various sensory outputs (e.g., balloon pressure, forces on balloon, impedance magnitude and time rate of change, power level) to detect indicators of complete division of the fibrous wall 110 (e.g., pressure changes, force changes, threshold levels of impedance and rate of change, current drop, apparent power loss), as later described in more detail.

Control and feedback components 214, in various embodiments, may be situated on handle 210 in convenient arrangement and orientation for easy use in operation. Preferably, these features can be raised or otherwise tactilely recognizable to a user (e.g., in shape, texture, etc.) so that the user may operate features of device 200 without having to look at the handle 210. This may beneficially permit the user to better focus on the procedure itself, resulting in lower risk and better performance. In an example embodiment, the handle 210 can includes indicator lights feedback components 214 on top and a button activation component 212 on the side, allowing a right-handed user to grip the handle 210 in its palm whilst allowing free movement of his/her thumb for working the button without having to twist or reposition the hand, which could potentially cause device 200 to shift away from a desired position and orientation within the body. The indicator lights, in the example embodiment, may provide the user with information concerning device state, using various colors, flashing sequences, flashing speeds, and the like. For example, the indicator lights may indicate things like: 1) pass power on test, 2) activated, 3) minimum balloon pressure achieved, 4) pressure timeout, 5) number of activations performed, amongst other useful information.

Continuing with FIG. 2A, in various embodiments, the handle 210 itself may be configured for facilitating the insertion, positioning, and removal of device 200 into/from the human (or animal) body during a medical procedure. In an embodiment, the handle 210 may include an ergonomic shape, such as a pistol grip shape, a reverse pistol grip shape, or an elongated handle shape similar to that of an electronic toothbrush (shown). These shapes may allow for stable and precise control of the device 200 as it is pushed (e.g., towards the site of treatment), pulled (e.g., retracted from the site of treatment), canted (e.g., to navigate contours within the body), and rotated (e.g., to align electrosurgical elements 500 with the fibrous wall to be divided). Additionally or alternatively, handle 210 may have a substantially flat under surface configured to allow handle 210 to rest flat on an external surface of the patient (e.g., along the forearm), thereby providing stability and eliminating torque during the procedure.

Figure 2B:
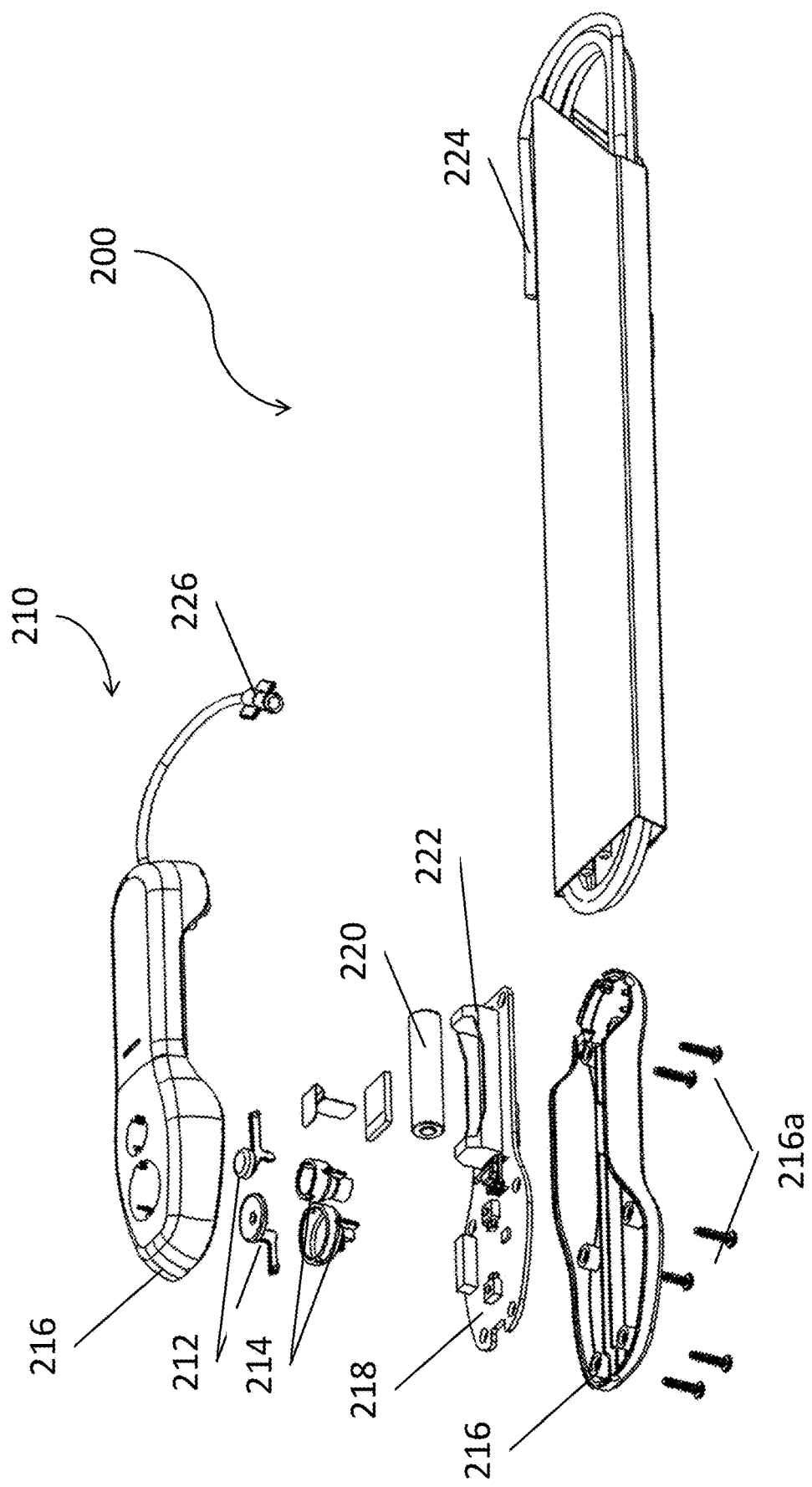
FIG. 2B depicts internal components of the handle of FIG. 2A, in accordance with an embodiment of the present disclosure.

Referring now to FIG. 2B, an exploded view of an example implementation of the handle 210 is depicted. In some embodiments, the handle 210 may include a housing 216, a programmable printed circuit board (PCB) 218, a power source 220 such as battery, the activation components 212, the feedback components 214, and an attachment 222 for receiving an electrosurgery cable 224 from an electrosurgical generator (or other power generation source), and an attachment 226 for receiving inflation tubing. The housing 216 can include any combination of housing materials and construction methods to encase the internal components of the device 200. For example, as depicted in FIG. 2B, the housing 216 can be two-piece construction that is coupled together using a plurality of fasteners 216a. Although any combination of manufacturing methods can be used to create the housing, for example, welding, adhesives, fasteners, three-dimensional printing, molding, etc. The housing 210 can be constructed to form an airtight/water tight seal such that the internal components are free from damage, contamination, etc.

In some embodiments, the PCB 218 can be coupled to the housing 210 and can be designed to couple to the combination of the power source 220, the activation components 212, the feedback components 214 along with any control logic to convey power, signals, etc. between these components. For example, the PCB 218 can include the necessary logic to receive a signal from the activation components 212 to trigger activation of one of the balloon 400 or electrosurgical elements 500 and receive feedback from those components and provide the signals to the feedback components 214 to convey that information to the user. Similarly, the PCB 218 can include the necessary conductive elements and/or wiring to transfer power from the power source 220 to the components on the PCB 218 itself (e.g., 212, 214, etc.) as well as other components of the device 200 (e.g., 400, 500, etc.). The power source 220 can include any combination of replaceable, rechargeable battery sources and wired power sources. In some embodiments, the PCB 218 can be designed with a plug to receive electrical energy via a power cable 224. For example, the PCB 218 can couple to a power cable 224 that is coupled to an electrosurgical generator that provides RF power that can be applied to one or more electrodes 500 of the device 200. In some embodiments, the PCB 218 can provide the logic and control circuits to deliver the power to the electrodes 500 to be applied to a patient. The PCB 218 can also provide logic and control for built-in safety systems such as cutting off the power after a specific period of time so that the RF power being applied to the electrodes 500 does not damage the tissue of a patient.

In some embodiments, the PCB 218 and/or handle 210 can also include one or more sensors 228 to obtain feedback for one or more aspects of the device 200, for example, measuring balloon pressure, detecting orientation of the distal end of the device 200. In some embodiments, the one or more sensors 228 can be integrated within or otherwise coupled to the PCB 218. In one example, the handle 210 can include a pressure sensor or monitor on the PCB 218 that is connected to the inflation tubing 216 to obtain a pressure reading for the balloon 400. The pressure sensor can be provided to monitor and prevent over pressurization of one or more components (e.g., balloon 400) of the device 200. The pressure sensor in this example can be part of a closed system that provided consistent pressure readings, for example, a Y-connection or T-junction can be used to split the inflation tube between the balloon 400 and the pressure sensor such that pressure is consistent across both points. The device 200 can also include any other combination of sensors to provide measurements, alerts, feedback, nerve sensing, etc. to a user. The pressure sensor can be mounted directly on the PCB 218 at any combination of locations, for example, on the bottom surface Referring now to FIGS. 2C and 2D, catheter 300, in various embodiments, may be rigid, semi-rigid or flexible. Catheter 300 may be made of any biocompatible material including plastic or metal. In an embodiment, catheter 300 may be made of a flexible plastic material such as polyurethane, polyethylene or flourothermoplastic, among other suitable plastics. In an embodiment catheter 300 may be sufficiently rigid to facilitate minimally-invasive insertion and to guide device 200 through the body and to the site of treatment, while also being sufficiently flexible enough to accommodate partial flexion of the wrist or other body parts. In an embodiment, a distal end of catheter 300 may have a tapered shape to facilitate passage of device 200 through tissue, thereby minimizing tissue trauma.

It should be recognized that, in some embodiments, catheter 300 may instead be situated within or otherwise supported by a shaft member (not shown) having these characteristics. The shaft member, in some embodiments, may accommodate catheter 300 or serve as catheter 300, providing passage of fluid for balloon 400 inflation and electrical current for activation of electrosurgical elements 500. In an embodiment, the shaft member may preferably have a size of about 10 Fr to about 14 Fr, but may be as large as necessary to provide the desired levels of stiffness discussed above, and to accommodate lumens 340, 350 and any necessary electrical components (e.g., wires) in communication with electrosurgical elements 500. The shaft member, in an embodiment, may be constructed as a multi-lumen extrusion of plastic (e.g., nylon, PEBAX) or stainless steel with insulation. The insulation serves to prevent a short circuit between the active electrode and the passive electrode as well as to prevent transmission of electrical and radio frequency (RF) current to a metal shaft if used. Further the insulation can prevent heat and energy transfer to the balloon 400 that may damage the balloon material resulting in perforation. In an embodiment configured for carpal tunnel syndrome procedures, the shaft member (or catheter 300) may have a length of about 4 inches to about 6 inches, or any other length suitable for positioning the handle in mid-forearm location when the balloon 400 and electrosurgical elements 500 is positioned percutaneously under the transverse carpal ligament.

Figure 2C:
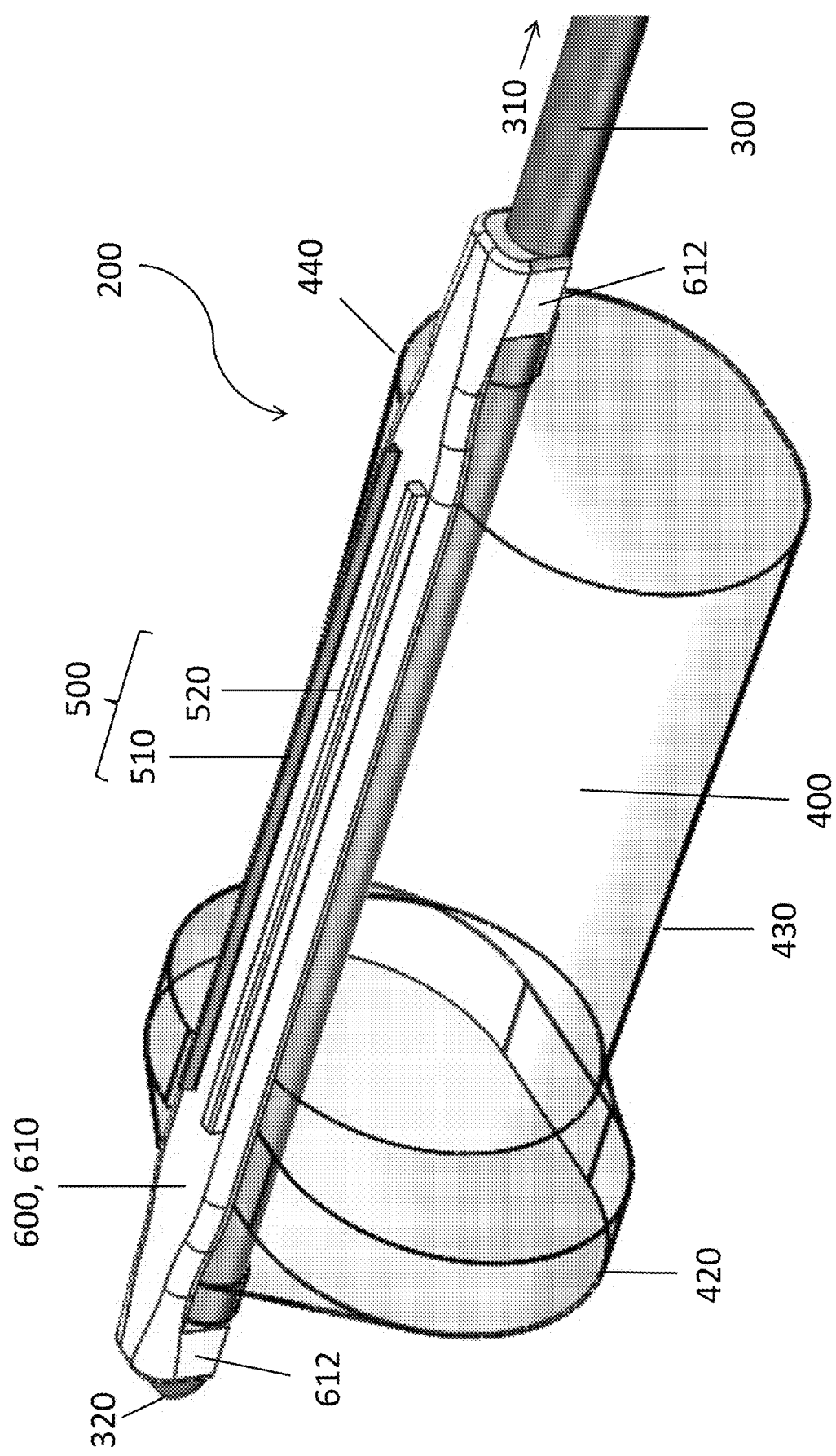
FIG. 2C depicts a device for minimally-invasive division of fibrous structures, in accordance with an embodiment of the present disclosure.
Figure 2D:
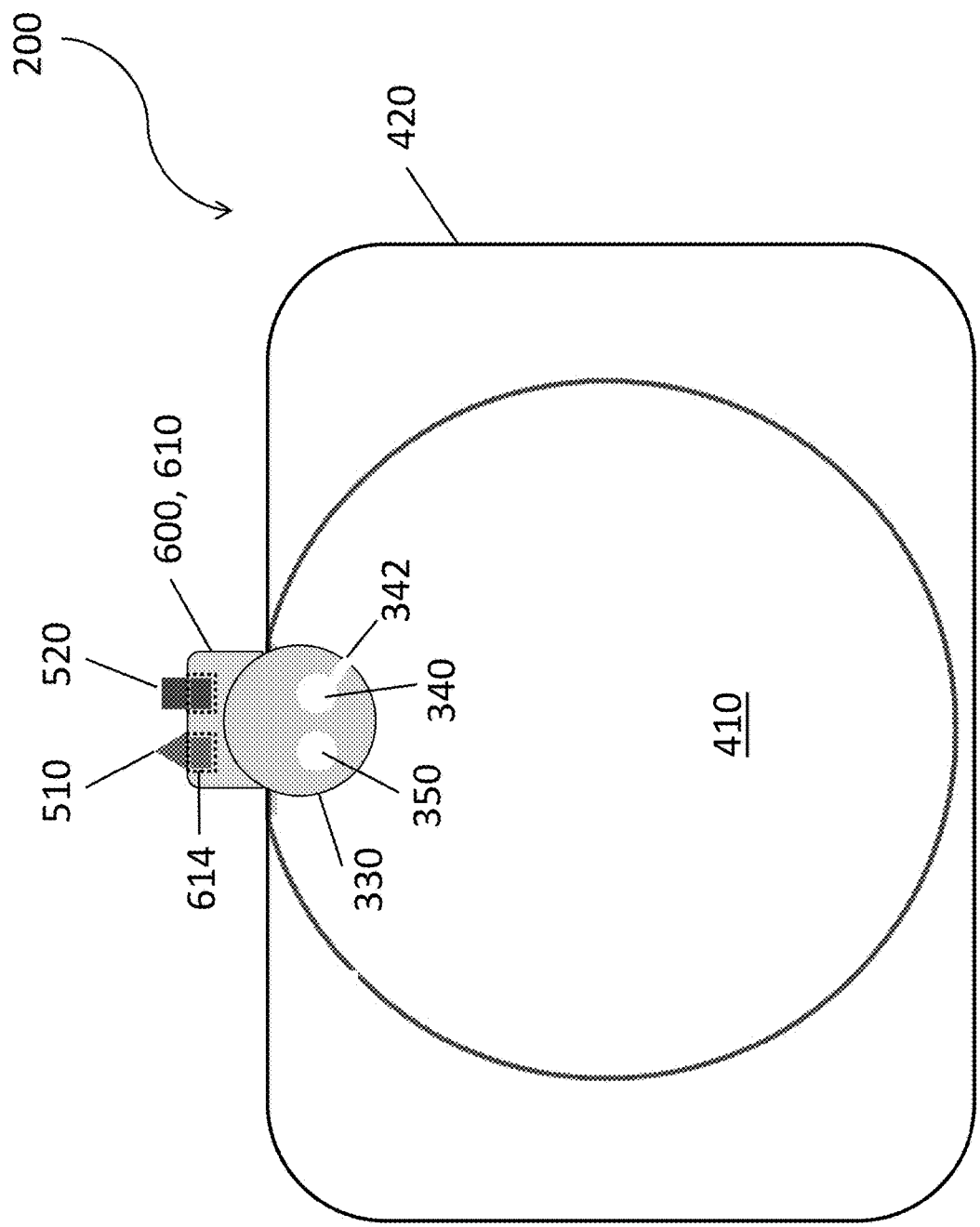
FIG. 2D depicts cross-sectional end views of the device of FIG. 2C for minimally-invasive division of fibrous structures, in accordance with an embodiment of the present disclosure.

Referring to FIG. 2D, in various embodiments, the catheter 300 may include at least one lumen 340 through which fluids may be directed for inflating and deflating balloon 400. The fluid (e.g., gas, liquid, etc.) may be directed between lumen 340 and an interior portion 410 of balloon 400 through one or more openings 342 in lumen 340. For example, in an embodiment, openings 342 may include side holes 342 extending radially from lumen 340 and through an outer surface 330 of catheter 300 so as to provide fluid communication between lumen 340 and an interior portion 410 of balloon 400. In operation, fluid may be introduced into lumen 340 at proximal end 310 and directed towards distal end 320, where it may escape through openings 342 and into interior portion 410 to inflate balloon 400. Similarly, fluid may be withdrawn from balloon 400 along the reverse path to deflate balloon 400.

In some embodiments, the lumen 340 can be coupled to inflation tubing extending from an external source (e.g., a fluid canister). For example, the lumen can be coupled to inflation tubing by the attachment 226 on the housing. The attachment 226 can include any combination of coupling mechanisms, such as for example a luer fitting. In such an implementation, inflation tubing can be coupled to the attachment 226 on the housing which can then provide a continuous flow path into the housing to the lumen 340.

Catheter 300, in various embodiments, may further include at least one lumen 350 for accommodating a guidewire for facilitating positioning of catheter 300 within compartment 100. In some embodiments, a guidewire may be used for initial access and is advanced to the site of treatment under direct, endoscopic, fluoroscopic, or ultrasonic visualization guidance, or through methods known in the art. It should be appreciated that such a guidewire may be stiff enough for these purposes (e.g., stiff enough to be advanced and guided into position within the body, while being flexible enough to accommodate contours and flexion of body parts).

Catheter 300, in various embodiments, may further include at least one lumen 360 (not shown) for accommodating wires or other electrical connectors connecting electrosurgical elements 500 and associated electrical components, for example, those in handle 210. For example, the power and/or signal wires for the electrosurgical elements 510, 520 can be situated through the lumen 360 for activating and deactivating the electrosurgical elements 500. It should be recognized that lumens 340, 350, 360 may be separate lumens or a one or more lumens with shared functionality in any suitable combination.

One of ordinary skill in the art will recognize that these are merely illustrative examples of suitable configurations of catheter 300, and that the present disclosure is not intended to be limited only to these illustrative embodiments.

Still referring to FIGS. 2C and 2D, minimally-invasive division device 200 may include expandable member 400, such as a balloon or similar expandable structure. For simplicity, expandable member 400 may be referred to herein as balloon 400 in the context of describing minimally-invasive division device 200; however, it should be recognized that balloon 400 is not intended to be limited as such.

Balloon 400, in an embodiment, may be non-compliant or semi-compliant in nature, and can be made of a thin layer or a similar flexible plastic material. Balloon 400 may have sufficient structural integrity to exert multiple atmospheres of pressure to assist in the dissection and elevation of the tissue plane of the transverse carpal ligament, in some embodiments, as later described in more detail. Non-compliant embodiments may be made from PET, for example, and provide the high burst pressure resistance and high local temperature resistance. Semi-compliant embodiments may be made from nylon (PA) or nylon elastomer (PEBA), for example, and may have better puncture resistance than PET. Semi-compliant embodiments may be configured to provide about 2 mm to 4 mm additional expansion as pressure increases from full size to expanded size.

Balloon 400 may be coupled to catheter 300 in a manner suitable for receiving and retaining fluid from lumen 340 of catheter 300 within interior portion 410 of balloon 400. In one such embodiment, balloon 400 may be positioned about a portion of outer surface 330 containing opening(s) 342 such that fluid directed through opening(s) 342 enters interior portion 410 of balloon 400. Balloon 400 may be bonded to catheter 300 to retain fluid directed into its interior portion 410 to allow for inflating balloon 400 during the surgical procedure.

Balloon 400, in various embodiments, may be shaped to apply tension to fibrous wall 110. As balloon 400 is inflated, it pushes outward, generating a force in a radial direction on a portion of wall 110, which stretches that portion of wall 110 in a lateral direction. In various embodiments, electrosurgical elements 500 may be longitudinally oriented on balloon 400, meaning that the lateral tension created in wall 110 by balloon 400 acts in a direction substantially transverse to the longitudinally-oriented electrosurgical elements 500 situated on the surface of balloon 400. As configured, lateral tension causes wall 110 to become taut across cutting element 500, thereby making it easier to divide. In particular, as electrosurgical elements weakens a contacted portion of wall 110, tension applied by balloon 400 facilitates division by pulling wall 110 apart along the weakened area. Further, stretching wall 110 taut provides for wall 110 to be contacted by a discrete portion of electrosurgical elements 500 (e.g., the pointed tip of active lead 510, as shown), rather than with a wider portion electrosurgical elements 500 as may be the case if wall 110 were slack and allowed to conform around cutting element 500. Stated otherwise, the tension applied by balloon 400 allows electrosurgical elements to act with high energy density on a small portion of wall 110, thereby providing for a cleaner cut with less tissue damage, which in turn may reduce the recovery period for the patient.

In an embodiment, balloon 400 may come in multiple sizes (e.g., small, medium, large, etc.) configured to accommodate various sized anatomical compartments 100 and to provide requisite tensioning to the fibrous wall 110. For example, in an embodiment used for carpal tunnel procedures, a size small balloon may have about a 12 mm inflated diameter, a size medium balloon may have about a 16 mm inflated diameter, and a size large balloon may have about a 19 mm inflated diameter. Of course, the present disclosure is not intended to be limited to these representative sizes, and one of ordinary skill in the art will recognize suitable diameter balloon 400 for a given application without undue experimentation. Balloon 400, in an embodiment, may be inflated to multiple atmospheres of internal pressure, such as from about 2 atm to about 10 atm, to form a "waist" in balloon 400 (later described) and provide high localized tension in the transverse carpal ligament. An integrated or accessory pressure inflation gauge, in various embodiments, may be used in conjunction with fluoroscopic assessment using radiographic dye in balloon 400 to assess the degree and location of "waisting" in balloon 400.

Balloon 400, in various embodiments, may be further shaped and sized to accommodate the specific anatomy of the compartment 100 within which it will be deployed. This may include, for example, being shaped and sized in a manner suitable for manipulating the position of, or minimizing pressure applied to, anatomical structures 120 situated within compartment 100. This may serve to protect these anatomical structures 120 from damage resulting from contact with electrosurgical elements 500 and/or to dissect tissues within the compartment to create more space for the anatomic structures within the compartment. In an embodiment, balloon 400 may have a substantially elongated cross-section (e.g., ovular) which, when positioned against fibrous wall 110, provides contact between an elongated side of balloon 400 and fibrous wall 110 that prevents anatomical structures 120 from sliding around its lateral ends and towards the site of division, where they could be damaged by electrosurgical elements 500. In another embodiment, balloon 400 may be provided with a substantially circular cross-section with a large enough diameter sufficient to push nearby tendons, nerves or other anatomical structures 120 outward from device 200 when inflated.

Figure 2E:
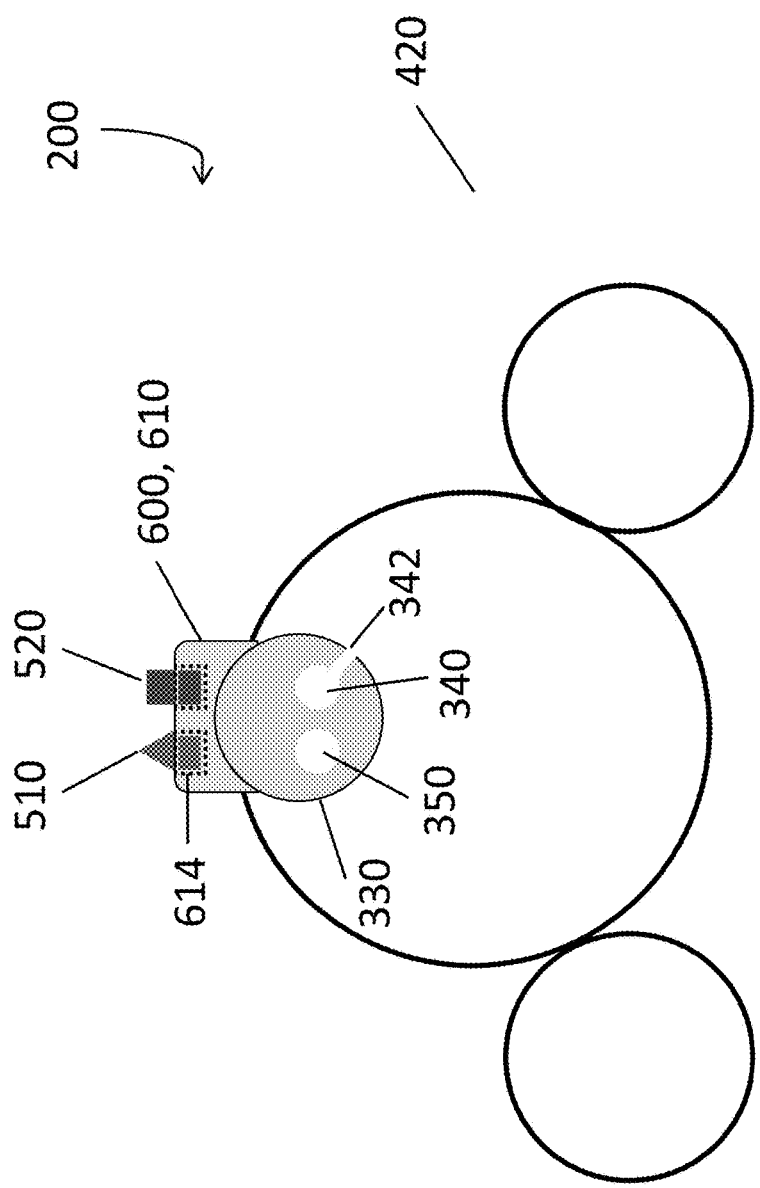
FIG. 2E depicts cross-sectional end views of a device for minimally-invasive division of fibrous structures, in accordance with an embodiment of the present disclosure.

In various embodiments, balloon 400 may be provided with a variety of other cross sections. For example, balloon 400 may have, without limitation, a substantially circular, ovular, rectangular, or triangular cross sectional shape, to help achieve the desired effect on wall 110 and/or anatomical structures 120. In some embodiments, multiple balloons or shaped members may be positioned in relation to one another to help form the overall shape of balloon 400. Referring to FIG. 2E, in one such embodiment, a "pontoon"-like configuration can be created by having a custom shaped balloon 400 or combining a plurality of different sized and shaped balloons to create a desired shape. For example, two smaller balloons can be positioned on opposing sides of a larger central balloon to help form an overall ovular shape. The combination of balloons can be combination of shapes and are not limited to the circular shapes depicted in FIG. 2E. For example, the central balloon can be cylindrical and the smaller balloons on each side can be oval shaped.

Similarly, such shapes as the pontoon shape can be formed from a single balloon instead of a combination of balloons. Various embodiments may include a proximal and distal cone to facilitate percutaneous navigation through and past various anatomical features. Of course, one of ordinary skill in the art will recognize any number of additional configurations for this purpose within the scope of the present disclosure.

Similarly, balloon 400 may be adapted to minimize contact with (and applying resulting pressure on) certain surrounding anatomical structures 120 within compartment 100. For example, the small vertical dimension of the elongated cross-sectional design of FIGS. 4A-4B may serve to minimize pressure exerted on median nerve 122 situated below the site of division, whilst its longer horizontal cross-sectional dimension may still serve to apply tension to fibrous wall 110 and push tendons 124 aside. For example, the balloon 400 can be 18 mm to 20 mm and can create a measurable distance between the median and ulnar nerves from the electrosurgical elements 500 of the device 200. Embodiments of balloon 400 may be provided with suitable longitudinal profiles adapted for similar purposes.

Referring still to FIGS. 2C and 2D, balloon 400, in some embodiments, may include a shaped feature 420 at or near its distal end to help engage anatomy within the anatomical compartment 100 and thereby prevent migration during inflation and/or division, as later explained in more detail. For example, in the embodiment shown, balloon 400 may include a "bulb" 420 or other shape having a larger diameter than proximal and central portions of balloon 400. Additionally or alternatively, pressure applied by the transverse carpal ligament may form a waist in balloon 400 when expanded, that may serve in like manner to help prevent migration of balloon 400 during the division process, as later described in more detail.

Still further, in various embodiments, device 200 may be configured such that the respective longitudinal axes of catheter 300 and balloon 400 are offset from one another as shown (referred to herein as an eccentric configuration). For example, as shown in FIGS. 2C and 2D, catheter 300 extends along an outer portion of balloon 400 rather than through the center. As configured, the inlet and outlet to/from an interior portion of balloon 400 provided by catheter 300 are more aligned with insulator 600. This may allow for the "belly" 430 of balloon 400 to inflate and push downwards from the "spine" 440 of the balloon (i.e., the opposing portions coupled to catheter 300) to elevate the transverse carpal ligament. Of course, as later shown in FIGS. 3A-3D, the respective longitudinal axes of catheter 800 and balloon 900 may be substantially coaxial in various embodiments.

Referring still to FIGS. 2C and 2D, minimally-invasive division device 200 may further include one or more electrosurgical elements 500. In various embodiments of device 200, electrosurgical elements 500 may be positioned on catheter 300, as best shown in FIGS. 2C and 2D. Electrosurgical elements 500, in various embodiments, may be configured to utilize different levels of electrical energy and/or thermal energy to detect nerves and/or divide fibrous wall 110. For example, the electrosurgical elements 500 can utilize RF energy to stimulate nerves and/or divide and separate a fibrous wall 110. RF energy is generally considered safe for cutting tissues in confined spaces where critical structures are present. In an embodiment, electrosurgical elements 500 may include any combination of sesquipolar, unipolar, or bipolar leads configured to communicate electrically with an electrosurgical generator. When separating or dividing the fibrous wall 110 the device 200 can deliver high frequency electrical energy. When the high frequency electrical energy meets the tissue, a high resistance is met which generates heat at the interface between the electrode 500 and the tissue and this heat can cut and separate the tissue.

In operation, when balloon 400 can be inflated and the electrosurgical lead(s) 500 come into contact with fibrous wall 110, the electrosurgical generator may be activated to deliver radiofrequency energy to the electrosurgical lead(s) 500. The level of inflation and shape of the balloon 400 can be designed to specifically position the tissue, surrounding area, and electrosurgical elements 500 for optimal division of a fibrous wall 110. For example, the balloon 400 can be sized and shaped to pull the wall in tension to create a gap between a top surface of the balloon 400 and the fibrous wall 110, as shown in FIGS. 4A-4C, while advancing the electrosurgical elements 500 toward the fibrous wall 110 for separation. The amount of power applied to the electrosurgical generator can vary at different stages of the procedure to yield different desired responses/results. In some embodiments, a smaller amount of power can be applied to the generator to determine whether the electrosurgical lead(s) 500 are in contact with a nerve before applying the full power. For example, during a carpal tunnel procedure, 50 W can be applied to see if a thumb twitches to determine whether a lead is contacting a nerve, if the thumb twitches then the lead(s) are in contact with a nerve and full power should not be applied to avoid damaging the nerve. If there is no twitching then full power can be applied to separate the fibrous wall 110.

As the electrosurgical generator is activated, the radiofrequency energy can be applied at a level to heat and cut the contacted, tensioned portion of the fibrous wall 110. As the RF energy is applied, the fibrous wall 110 is divided under the pressure of balloon 400, thereby relieving the pressure in compartment 100, as described in more detail later in the disclosure. An electrical cable 224 or other electrical conduit may be provided, in some embodiments, to electrically connect an electrosurgical generator to the handle of device 200 to provide the RF energy.

In some embodiments, the device is provided with a bipolar two electrode configuration with at least one of the electrodes acting as an active lead 510 and the other acting as a dispersive or return lead 520 (also referred to herein as passive lead). In some embodiments, the electrosurgical elements 500 can be configured in a configuration that includes the active lead 510 and the return lead 520. In a sesquipolar configuration one of the electrodes 500, for example, the return electrode 520, can be much larger relative to the other electrode, in this example, the active lead 510. In some embodiments, the active lead 510 can be further shaped such that it concentrates the energy being applied. For example, the active lead 510 can be triangular in geometry and coated on the sides in order to concentrate the energy delivery to a very thin sliver of exposed metal at the ridge of the active lead 510. This focused energy delivery can minimize trauma to the tissue during cutting and minimizes thermal spread, as discussed in greater detail herein.

In some embodiments, the active lead 510 delivers the energy to the tissue (e.g., for division of the tissue) while the return lead 520 completes the circuit acting as an electrical ground. Leads 510, 520 may be made from any suitable conductive material, and in an embodiment, can be made from a conductive metal such as stainless steel for durability and conductivity. Stainless steel is low cost and offers a multitude of manufacturing processing options. Leads 510, 520 may be positioned parallel to and adjacent to one another with a gap in between. If the gap is too small, the current may not go through the tissue sufficiently to divide the tissue. If the gap is too large, the current may move too diffusely through the tissue to produce adequate divisions. While not intended to be limited as such, in some embodiments, a gap of about 1 mm to 2 mm or more with heights (above the insulating member 600) ranging from 0 mm to about 1 mm can be used to produce adequate divisions.

When energized, the electrosurgical elements 500 can be in any configurations that can concentrate the RF energy in active lead 510, as opposed to between the two leads in bipolar configurations, thereby allowing active lead 510 to focus cutting energy along a single, well-defined linear path. This configuration can provide for dividing the fibrous wall along a fine line, which may result in less tissue trauma, shorter cutting times, faster recovery times, and more precise division of the fibrous wall 110.

Device 200, in various embodiments, may be configured to allow for short duration pulses of energy to perform the tissue division. In an embodiment, pulses may be delivered on the order of about 1 second to 3 seconds per pulse, either under manual control by the physician (i.e., pulse lasts as long as trigger pull) or via a setting (e.g., controlled by the PCB 218) that automatically delivers pulses at the set duration upon command. This provides a defined and focused delivery of cutting energy to cut the target tissue rather than ablate the tissue with limited thermal injury and spread caused by the energy. Device 200, in an embodiment, may be designed for optimal usage at lower power RF settings, such as those on the order of about 20 W to about 100 W. Prototype testing in a cadaver lab indicated that, for the embodiment tested, a 1-3 second pulse was optimal as shorter durations did not always result in cutting the transverse carpal ligament and longer durations did not provide increased cutting consistency. Similarly, these tests indicated that, for the embodiment tested, about 20 W-100 W was optimal in that it provided the most consistent full division of the transverse carpal ligament. Lower energy levels did not always cut the transverse carpal ligament and higher energy levels did not provide increase cutting consistency.

In some embodiments, the active lead 510 can be energized a single time or repeatedly energized and/or advanced against the target area to perform a division of fibrous wall 110. In implementations where there is not a full division of the fibrous wall 110 after the first energization and advancement process, the pressure of the balloon 400 can be evaluated (e.g., via pressure sensor) and adjusted if necessary for a subsequent energization and advancement process. For example, if the pressure of the a balloon 400 is below a given threshold after the process, then it can re-inflated to a target pressure (e.g., 2 atmospheres) for subsequent division attempts.

In a first example, the initial inflation of the balloon 400 and activation of the active lead 510 can result in a full division of the fibrous wall 110. In this instance no additional steps may be required. In a second example, the initial inflation of the balloon 400 and activation of the active lead 510 can result in a partial cut division of the fibrous wall 110 and the balloon 400 maintains a pressure within an acceptable range (e.g., about 2 atmospheres). In this instance the active lead 510 can be reenergized for the predetermined period of time to further and/or complete the division. In a third example, the initial inflation of the balloon 400 and activation of the active lead 510 can result in a partial division of the fibrous wall 110 and the balloon 400 can fall below a predetermined pressure threshold (e.g., <2 atmospheres).). In this instance the balloon 400 can be re-inflated to the target pressure (e.g., about 2 atmospheres) to provide sufficient tension and advance the active lead 510 toward the target division point. Thereafter, the active lead 510 can be re-energized to further and/or complete the division. The steps in these examples can be repeated any number of times until a desired division of the fibrous wall 110 is achieved.

Active lead 510, in various embodiments, may protrude above the top surface of device 200 (i.e., above insulating member 600 on balloon 400) and can be provided with a profile having a sharp tip, such as a triangular profile, as shown in FIGS. 2C and 2D. Such a profile may serve to concentrate the energy at the tip of the active cutting lead 510, thereby providing highly-concentrated energy density along a fine line at the site of division. This may result in less tissue trauma, shorter cutting times, faster recovery times, and more precise division of the fibrous wall 110. In particular, the device 200 reduces the risk of temperature rises (e.g., heating) by limiting any transient rise in temperature to within 0 mm to about 1 mm of the active cutting lead 510. Further, the sloping surfaces of the triangularly-shaped lead 510 may serve to further spread (i.e., tension) the portion of fibrous wall 110 proximate the leading edge (i.e., tip), thereby further enhancing the ability of device 200 to divide fibrous wall 110.

Additionally or alternatively, in various embodiments, a portion of the surface of the lead 510 extending up sloping surfaces may be covered with an insulating material, allowing further concentration of the energy density to be focused about the leading edge of active lead 510. For example, the insulating material can cover substantially all except a narrow (e.g., <100 microns) sliver along the top edge of the active lead 510 (e.g., the vertex of the triangular shape). By limiting the exposed metal on the active lead 510 to a narrow sliver, the energy can be concentrated and focused to a fine line on the tissue, allowing it to rapidly and precisely cut the target tissue along this line. Additionally, the spread of thermal energy beyond this narrow line can be limited with short bursts of the energy along the narrow line. In another embodiment, the entire active lead 510 may be coated with the insulating material, but with the tip having a thinner coating such that energy is concentrated there.

In some embodiments, as shown in FIG. 2D, the insulating member 600 can be figured configured with a slot for receiving active lead 510 as later described in more detail, and can cover a portion of the sloping surfaces of triangular lead 510 to provide this energy-concentrating functionality. Additionally or alternatively, in another embodiment (not shown), a lower portion of the sloping surfaces may coated with an insulating material for similar purposes. Similarly, the insulating member 600 can also include a slot for receiving the passive lead 520.

Passive lead 520, in various embodiments, may be flush with or protrude above the top surface of device 200. As cutting energy is not concentrated in the passive lead, in some embodiments, the shape of passive lead 520 can be less consequential. For example, in an embodiment, passive lead 520 may be a simple rectangular shape. However, it should be recognized that the extent to which passive lead 520 protrudes from the top surface of device 200 may affect the way the transverse carpal ligament is tensioned during the division process. For example, in embodiments in which passive lead 520 is flush with the top surface or otherwise lower in profile than active lead 510, the less it will affect a localized "tenting" effect on the shape of the tensioned transverse carpal tunnel ligament caused by protrusion of active lead 510. Conversely, in embodiments in which passive lead 520 protrudes further from the top surface of device 200, the more it will affect the localized tenting effect over active lead 510, creating a localized plateau shape in the transverse carpal ligament above leads 510, 520. It should be recognized that the plateau-like shape induced by a protruding passive lead 520 may serve to further tension the transverse carpal ligament in the region of lead 510, thereby further facilitating division of the ligament along the line defined by active lead 510. The plateau-like shape also serves to improve the consistency of contact with the electrode to the TCL thereby improving the current transmission from the active lead to the passive lead improving performance of the cutting method.

Passive lead 520, in various embodiments, may be left uncoated with insulating material or otherwise exposed to maximize its conductivity and to provide localized electric field control. This may facilitate the creation of a strong localized electric field between leads 510, 520, thereby enhancing the cutting power of active lead 510 in which the energy is concentrated for cutting.

A traditional bipolar configuration, on the other hand, typically includes two leads of identical size and shape. Bipolar leads are often used for tissue cutting when the leads may be placed on opposing sides of the tissue to be cut, as the energy is densely concentrated in the tissue zone between bipolar leads. Such a configuration could work when engaging the transverse carpal ligament from one side, as with device 200; however, it should be recognized that the bipolar cut may not be a localized as it would be with a sesquipolar configuration, as the bipolar cut may occur somewhere in the gap between the bipolar leads. A bipolar configuration may in some cases be preferable in anatomic areas with critical structures (nerves, blood vessels) in the vicinity, as it limits the thermal spread of the radiofrequency energy.

Electrosurgical elements 500, in various embodiments, may have a flexible construction to allow them to bend without fracturing or delaminating from catheter 300, insulating material 600, etc. of device 200 (or from balloon 400 of device 700, as later described). In an embodiment, elements 500 may include a scalloped profile to provide adequate bending tolerance in the presence of loads. Other profiles may be utilized for similar effect. Additionally or alternatively, in various embodiments, electrosurgical elements 500 may be coupled with device 200 using a coupling mechanism that allows elements 500 to flex without uncoupling from devices 200. In one such embodiment, as shown, elements 500 may be mechanically attached to grooves 614 in the surface of a catheter 300 and/or a solid insulating member 610 (later described) of device 200. These grooves 614 may help to prevent detachment of elements 500 and allow for movement in the direction of the flex incurred. In another such embodiment, elements 500 may be attached to device 200, and in particular, to a thin-film insulating member 620 (later described) using a highly-compliant adhesive that can elastically deform enough not to detach. Examples include without limitation cyanoacrylate (CA) or acrylic-based ultraviolet light cure (UVC) such as acrylated urethane with UV curing.

In some embodiments, electrosurgical elements 500 may also be configured to remain fixed under the target tissue until the tissue is divided/cut, at which point the device shuts off the energy through the active lead 510. This allows the device 200 to divide and separate tissue without requiring and lateral movement (e.g., back and forth) of the device 200. In other words, the device 200 merely requires vertical or radial movement caused by the inflation of the balloon 400 to divide and separate the tissue. The combination of a burst of energy provided at a narrow edge of the lead 510 and the non-movement of the lead 510 enables a precise zone of injury (e.g., division/cut) to the target tissue.

In some embodiments, the device 200 can be designed to automatically power on/off the device 200 and/or the electrosurgical elements 500 based on feedback from one or more other sensors. For example, if the pressure sensors detected a pressure level that is determined (e.g., by a processor on the PCB 218) to be above or below a predetermined threshold for preferred environment for tissue division, then power to the electrosurgical elements 500 can be cut off. By cutting power to the electrosurgical elements 500 when the parameters are not ideal can provide a safer situation in which a division of the tissue can be achieved. In some embodiments, the user can be alerted of the situation (e.g., via feedback components) to enable the user to adjust the device 200 or a component thereof. Continuing the example, if the electrosurgical elements 500 are powered off in response to the balloon 400 having a pressure under a desired level (e.g., under about 2 atmospheres of pressure) then the user can be alerted that the balloon 400 needs to be inflated to the appropriate pressure. Once the desired pressure is achieved, for example as determined by the pressure sensors, then the power to the electrosurgical elements 500 can be re-activated for use by the user.

Referring still to FIGS. 2C and 2D, minimally-invasive division device 200 may further comprise an insulating member 600 situated between electrosurgical element 500 and catheter 300 (or between electrosurgical element 500 and balloon 400 of device 700, as later described), so as to protect catheter 300 (or balloon 400 of device 700, as later described) from heat-related damage when electrosurgical element 500 is energized. The insulating member 600 can be coupled to the balloon 400 and the electrosurgical elements 500 using any combination of methods. Similarly, the electrosurgical elements 500 can be coupled to the insulating member 600, imbedded within the insulating member 600 or protruding through the insulating member 600. For example, the insulating member 600 can be an insulating electrode spacer designed to provide sufficient spacing between an active electrode 510 and a passive electrode 520 to prevent a short circuit between the electrodes 510, 520.

Insulating member 600, in various embodiments, may be constructed of a flexible polymeric material that has high resistance to electrical tracking across its surface between electrosurgical elements 500 situated thereon. For example, in an embodiment, insulating member 600 may include a polyimide film such as Kapton tape. Of course, insulating member 600 may include or be constructed of any material suitable for providing a thermal barrier between electrosurgical element 500 and catheter 300 (or between electrosurgical element 500 and balloon 400 of device 700, as later described) without departing from the scope of the present disclosure.

Insulating member 600, in the embodiment shown, may be a rigid or semi-rigid member 610. Insulating member 610 may include clips 612 or other suitable coupling mechanisms for coupling with catheter 300 (or the shaft, as previously described) on opposing ends of balloon 400, as shown in FIG. 2C. As configured, insulating member 610 may provide additional stiffness to the corresponding portion of device 200, which may facilitate its navigation to and placement at the site of treatment. The stiffness of the insulating member 610 may be provided to provide sufficient stiffness to minimize bending/flexing assist in the navigation of the distal end of the device 200 during insertion toward a target site within a body. In an embodiment, insulating member 610 may include grooves 614 in its top surface for receiving electrosurgical elements 500, as previously discussed and shown in FIG. 2D. Of course, it should be recognized that electrosurgical elements 500 may be coupled thereto without grooves 614 or a combination of grooves 514 or no grooves. For example, the active lead 510 can be positioned within a groove 514 while the passive lead 520 is not.

In another embodiment (not shown), insulating member 600 may include a thin-film or other thin, flexible insulating material 620 for placement between electrosurgical elements 500 and catheter 300 (or between electrosurgical element 500 and balloon 400 of device 700, as later described). Such an embodiment is later described in more detail in the context of device 700, and may be utilized in embodiments of device 200 as well.

Minimally-Invasive Division Device 700

Referring now to FIGS. 3A-3D, the present disclosure further includes a minimally-invasive division device 700. Embodiments of minimally-invasive division device 700 may generally include a catheter 800, an expandable member 900, one or more electrosurgical elements 1000, and an insulating member 1100. Like minimally-invasive division device 200, device 700 may be inserted into the body and advanced towards an anatomic compartment 100, such as the carpal tunnel, requiring treatment. Once properly positioned within the anatomic compartment, expandable member 900 may be expanded to apply a radial force to fibrous wall 110, generating lateral tension along a portion of the fibrous wall 110 of the compartment 100. Electrosurgical elements 1000 may be configured to engage the tensioned portion to divide the fibrous wall 110 and thereby decompress the anatomic compartment 100 for therapeutic effect.

Various components of device 700 are substantially similar to complementary components of device 200, and suitable characteristics and embodiments thereof are hereby incorporated into this description of device 700. For example, embodiments of catheter 300 have similar size and rigidity considerations for advancing device 700 through the body, and accommodating fluid for inflating balloon 900 and electrical wires for activating electrosurgical elements 1000. Similarly, embodiments of balloon 900 have similar shape, size, and pressure considerations for tensioning and separating fibrous wall 110 from surrounding anatomy, and embodiments of electrosurgical elements 1000 have similar type, shape, and power considerations for cutting fibrous wall 110. For example, the balloon 900 (or balloon 400) can be sized and shaped to displace and separate critical structures, such as the median nerve, recurrent motor branch of the medial nerve and ulnar nerve, from the active lead 510 during the division of the target tissue (e.g., as depicted in FIGS. 4A and 4B).

In an embodiment, a distal end of catheter 800 and/or balloon 900 may have a tapered shape to facilitate passage of device 700 through tissue, thereby minimizing tissue trauma. The tapered shape of the catheter 800 and/or balloon 900 can be sufficiently rigid to assist in the advancement of the device 700 to the target site within a body. Representative dimensions of an embodiment of device 700 are shown in FIG. 3B. In some embodiments, device 700, as shown in FIGS. 3A-3D, the device 700 can be provided without a rigid or semi-rigid insulating member 1100 comparable to insulating member 600 of device 200. Instead, the device 700 can include a thin-film style insulating member 1120 comparable to insulating member 620 mentioned with respect to device 200. Insulating member 1120, in various embodiments, may be configured to couple directly to an outer surface of balloon 900, as opposed to coupling to catheter 800. In particular, insulating member 1120 may include a thin film with high dielectric strength suitable for insulating and protecting balloon 900 from thermal damage. These films 1120 can be provided with adhesive backing for coupling with balloon 900. Representative materials for insulating member 1120 include PI (Kapton), PEEK, and nylon.

Referring now to FIGS. 3C and 3D, representative embodiments of electrosurgical elements 1000 are shown as coupled to insulating member 1120 on balloon 900. With reference to FIG. 3C, active lead 1010 can protrude upwards and can have a pointed, triangular profile, and passive lead 1020 rectangular protrudes upwards and has a rectangular profile. With reference now to FIG. 3D, in an alternative configuration, passive lead 1020 is flat or flush with the surface. These configurations can be provided for energy density-related and tension-related reasons previously discussed in connection with device 200. In some embodiments, the electrosurgical elements 1000 can be radially positioned about a curvature of the balloon 900, as depicted in FIGS. 3C and 3D.

Systems and Methods for Nerve Stimulation and Detection Using Devices 200, 700

Although the embodiments discussed with respect to FIGS. 3E-3I are discussed with respect to device 200 and the leads 510, 520, the same features can be applied to the device 700 with the leads 1010 and 1020. In some embodiments, electrosurgical elements 500 may also be configured to stimulate and/or detect nerves near electrosurgical elements 500, 700 to minimize potential for damaging a nerve near a division site. In particular, electrosurgical elements 500 may be designed for sensing neuroelectrical activity, stimulating neuroelectrical activity, or both, in a nearby nerve, if present. The device 200 can be designed to stimulate and detect any combination of motor nerves and sensing nerves. Motor nerves can be stimulated and detected by the application of low energy to trigger a twitching response to indicate the presence of a motor nerve.

In some embodiments, the active lead 510 of the device 200 can be designed to apply different levels of energy to provide either nerve sensing/stimulation and division of the tissue at different times. For example, the handle 210 can include a button that adjusts the power used and/or provided by the radiofrequency generator to the active lead 510 to enable transition between nerve sensing mode and fiber division mode. The power level can also be adjusted through a manual or automated adjustment at the radiofrequency generator. In some embodiments, an energy level of 1-5 watts can be applied via the active lead 510 to stimulate and detect motor nerves. In another example, the power level can be manually or automatically adjusted at an RF generator and/or using different activation components 212 to activate the different modes (e.g., sensing mode and fiber division mode).

Based on a nerve stimulation and detection process by the device 200, the device 200 can detect the presence of nerves located nearby and then moved and/or adjusted away from the nerve. Referring to FIG. 3E depicts the device 200 positioned under a fibrous wall 110 to be divided. The sensing mode on the device 200 can be triggered to determine whether a nerve is located within range of the active lead 510, for example, by applying lower radiofrequency power (e.g., 1-5 watts) to the active lead 510. If no nerve is located near the active lead 510, as depicted in FIG. 3E (no noticeable twitching after activation of the active lead 510 is observed), then the device 200 can be changed to division mode. In FIG. 3E, there is a nerve 120 present under the device 200 but out of harm's way, so the nerve sensing will be negative and the user can begin division of the fibrous wall 110. During division mode, the larger radiofrequency power level (e.g., greater than 20 watts) can be applied to the active lead 510 to provide sufficient energy to divide the fibrous wall 110. The larger RF power level can be adjusted manually, automatically and/or through execution of a division button.

FIG. 3F depicts the device 200 positioned under a fibrous wall 110 to be divided. The sensing mode on the device 200 can be triggered to determine whether a nerve is located within range of the active lead 510 by applying the lower radiofrequency power to the active lead 510. If a nerve is sensed near the active lead 510, as depicted in FIG. 3F, (noticeable twitching after activation of the active lead 510 is observed) then the device 200 can be repositioned and relocated to be tested for nerves at a new location and/or orientation. In FIG. 3F, there is a nerve 120 present near the active lead 510 such that if the nerve sensing mode is active, then noticeable nerve twitching would occur. In this instance the user would need to reposition and/or relocate the device to avoid causing nerve damage during activation of the division mode.

Referring to FIG. 3G, in some embodiments, the nerve sensing can be used to determine an orientation of the device 200. If a nerve is detected (noticeable twitching after activation of the active lead 510 is observed), then the device 200 can be repositioned and relocated to be tested for nerves again. For example, if it is known that no nerves should be located between the electrodes 500 and the fibrous wall 110, then visible twitching in response to the nerve sensing activation could indicate that the device 200 is rotated in a wrong direction. This can also provide a way to confirm that the nerve 120 is not between the ligament 110 and the electrodes 510 and 520, such that the device can be rotated in the correct orientation for cutting (e.g., the electrodes 510, 520 are facing the ligament 110) and the nerves are not in the way. FIG. 3G depicts the device 200 positioned under a fibrous wall 110 with the electrodes 500 positioned away from the fibrous wall 110 toward a nerve 120, such that if the nerve sensing mode is active, then noticeable nerve twitching would occur. In this instance the user would need to reposition and/or relocate the device to the proper positioning and to avoid causing nerve damage during activation of the division mode.

Referring to FIGS. 3H and 3I, in some embodiments, the device 200 can include an electrode array 530, separate from the active and return electrodes 510, 520, at or near the distal end of the device 200. The electrode array 530 can be configured to send electrical signals to potentially trigger muscle movement and/or determine if there is any signal conduction through the nerve. This method can be used to capture both motor nerves as well as sensory nerves. Typically, a subject would need to be awake and of clear mind to convey that they felt something near a sensory nerve. Using the electrode array 530 connected to a device capable of measuring an electrical response (e.g., electrical conductivity) to the electrical energy and/or thermal energy delivered to the nerve stimulation electrosurgical elements in or other identifiable changes of the applied energy to the electrode array 530 can be monitored for the detection of both motor and sensor nerves. For example, an identifiable change in the signal conductivity over the electrode array 530 can be monitored to determine whether either a motor nerve or a sensory nerve is near the location of the electrodes 510, 530.

In some embodiments, the electrode array 530 can include one or more electrodes positioned substantially parallel to at least one of the active and return electrodes 510, 520, as depicted in FIGS. 3H and 3I. The electrode array 530 can be dedicated nerve sensing electrodes that include an input and an output such that conductive changes to an applied energy applied over the electrode array 530 can be monitored to determine the presence of a nerve. In some embodiments, the electrode array 530 can include a combination of electrodes 530*a*, 530*b* positioned substantially parallel on either side of the active and return electrodes 510, 520, as depicted in FIG. 3I. As shown in FIG. 3I, the electrode array 530 can include two separate electrode lines 530*a*, 530*a* with one acting as an input and one acting as an output for measuring a change in the signal conductivity over the electrodes 530*a*, 530*b*. Although the electrode array 530 can be placed near at least the active electrode 510 to best ensure that there are not any nerves near the active electrode 510, the electrode array 530 and/or electrodes 530*a*, 530*b* can be placed at any combination of locations on the device 200 for nerve stimulation/detection.

Any combination of the electrodes 510, 520, 530 may be utilized to determine whether balloon 400 and electrosurgical elements 500 are positioned and oriented appropriately relative to the tissue to be divided, such as the transverse carpal ligament, and other anatomical structures not to be disturbed, such as the median nerve. In some embodiments, whether electrodes 510, 520, 530 function as a sensing, stimulating or cutting element can be determined by the level and/or type of energy being applied to the electrodes 510, 520, 530. For example, if the electrodes 510, 520, 530 electrically communicate with a signal detector or stimulator they can be used for nerve detection or stimulation. Similarly, lower RF energy being applied to the electrodes 510, 520, 530 can be applied for nerve detection or stimulation, whereas higher levels of RF energy can be applied for division of tissues. In some embodiments, the nerve stimulation electrosurgical elements (e.g., electrodes 530) can be connected to a separate generator than the electrosurgical elements (e.g., electrodes 510, 520) to perform their functions separately. In other embodiments, the electrode array 530, the active electrode 510, and the return electrode 520 can share a common power source but can be configured to receive different levels of energy (e.g., radiofrequency) to yield the desired results. For example, as discussed herein, the nerve detecting power applied to the electrode array 530 can be significantly lower than the cutting power applied to the active electrode 510.

Using any combination of configurations discussed with respect to FIGS. 3A-3I, an operator may utilize feedback from some combination of the electrosurgical elements 510, 520, 530 to determine whether electrosurgical elements may be in the vicinity of a nerve, such as the median nerve in the carpal tunnel prior to cutting. Electrosurgical elements 510, 520, 530 may be designed to detect an electrical signal emanating from a nearby nerve (e.g., the median nerve) at baseline or from activation of motor nerve fibers during normal muscle contraction (e.g., hand grip) or during electrical stimulation of the nerve (e.g., in the forearm), similar to how nerve conduction studies are performed. A positive signal would confirm that the nerve is located close to at least one of electrosurgical elements 510, 520, 530, and that repositioning and/or reorientation is required. Additionally or alternatively, electrosurgical elements 530 may be configured to emit an electrical stimulus signal for stimulating nearby nerves, for example in an analogous manner as commonly utilized nerve stimulators used in anesthesia to assess successful pharmacologic muscle relation. A positive response to stimulation would provide confirmation that the nerve is located close to electrosurgical elements 510, 520, 530, indicating that repositioning and/or reorientation is required. In some embodiments, a positive reading can automatically trigger action to disable the division mode such that, even if a division button is pressed on the handle 120, no division level RF energy can be transmitted to the electrode 510 until the device 200 is relocated and it is confirmed that no nerves are present located near the electrosurgical elements 510, 520, 530.

Methods for Treatment of Carpal Tunnel Syndrome Using Devices 200, 700

Referring now to FIGS. 4A-4C, embodiments of devices 200, 700 may be well-suited for treating various conditions that require division of tissue or fibrous walls 110. For example, the devices 200, 700 may be particularly well-suited treating carpal tunnel syndrome by dividing the transverse carpal ligament. The devices 200, 700 can be provided as a complete system or device or part of a kit to be configured for a procedure (e.g., treating carpal tunnel syndrome). The carpal tunnel is an anatomic compartment in the wrist bounded by the carpal bones and the transverse carpal ligament. The clinical symptoms of carpal tunnel syndrome primarily arise from compression of the median nerve as it passes through the tunnel. Surgical division of the transverse carpal ligament relieves the compression of the median nerve and its associated symptoms.

Embodiments of devices 200, 700 are capable of dividing the transverse carpal ligament percutaneously. In addition, devices 200, 700 may, in operation, dissect and mobilize the median nerve and tendons away from the transverse carpal ligament, thereby enhancing the decompression of the carpal tunnel and potentially preventing late scarring and recurrent symptoms. For ease of explanation, the following methods for treatment of carpal tunnel syndrome will be explained in the context of using device 200, though it should be recognized that similar methods may be employed using device 700 within the scope of the present disclosure.

When provided as part of a kit, the devices 200, 700 can be unpackaged, inspected, and configured for the procedure. For example, using aseptic technique, remove the devices 200, 700 can be from a sterile container, visually inspected for signs of damage (bent shaft, damage to handpiece, etc.), and hooked up to any external devices. The devices 200, 700 can also have other design elements that identify an unused device. For example, devices 200, 700 can have an intact battery tab and the end of the device 200, 700 and be covered with a protective sleeve. Initialization can include plugging the device into an electrosurgical generator removing the battery tab and power on the device 200, 700 (e.g., by pressing and holding a power button for two seconds). If in response to pressing the power button until an indicator light illuminates (e.g., solid blue), the protective sleeve can be removed (e.g., by sliding off the sleeve). If the indicator lights indicates an error in response to pressing the power button (e.g., illuminates solid red) after removing the battery tab the device may not be acceptable for use and can be replaced. The device 200, 700 can include any combination of indicators that the device is properly configured for use. For example, an alarm can sound if the power cable 224 is not properly coupled to the electrosurgical generator.

Initially, a patient can be prepped for application of the device 200, for example, for treatment of carpal tunnel syndrome using the device 200. For a carpal tunnel syndrome procedure the patient can be positioned supine on the operating room table with the operative hand palm facing up on an arm board. The hand may be positioned with slight extension by placing a rolled towel or other support device under the wrist and securing both the forearm and the hand to the operative table. A tourniquet may be used, and if so the arm must be prepared and draped in a sterile manner allowing for placement of the tourniquet and exsanguination of the hand and forearm using an esmarch bandage or the like if desired. In some embodiments, general, regional or local anesthesia can be used.

In operation, device 200, with balloon 400 in a deflated state, may be inserted into the body and advanced into the carpal tunnel. Device 200 may be navigated into a position proximate the transverse carpal ligament, and oriented such that electrosurgical elements 500 are pointed towards the transverse carpal ligament and away from other critical structures, such as the median nerve and surrounding flexor tendons. Embodiments of device 200 may be of suitable dimensions for positioning within the carpal tunnel in proximity to the transverse carpal ligament. Once in a desired position, the device 200 can confirm that the area is free from nerves, for example, as discussed with respect to FIGS. 3E-3I. The positioning and orientation of electrosurgical elements 500, at this stage, may be confirmed by any suitable technique, including ultrasonic or fluoroscopic imaging techniques described herein in greater detail and/or nerve sensing and stimulation techniques. The positioning and orientation of electrosurgical elements 500 can be confirmed to ensure the electrodes 500 remain in a strict anterior position facing the target tissue. The device 200 can be positioned such that the proximal ends of the electrodes are aligned with the proximal edge of the TCL or the electrodes span the full width of the TCL and remain facing the target TCL. Ensure that neither proximal nor distal ends of the electrodes are in contact with the skin or non-target tissue.

Referring now to FIG. 4A, after confirming that electrosurgical elements 500 are properly positioned and oriented relative to the transverse carpal ligament and surrounding anatomical structures such as the median nerve and flexor tendons, balloon 400 may be inflated. Balloon 400 may be configured to expand to dimensions appropriate for use within the carpal tunnel. Embodiments of balloon 400 having an elongated cross-sectional shape, or other suitable shape, may act to dissect the transverse carpal ligament off the carpal tunnel contents during inflation, creating space and enhancing the decompression of the carpal tunnel. In such an embodiment, balloon 400 can be made of a substantially noncompliant material and may be inflated to a specified pressure, designed to achieve this dissecting effect and to provide enough radial force to stretch the transverse carpal ligament across electrosurgical elements 500 for subsequent division. As shown in FIG. 4A, the inflated balloon 400 has dissected and pushed the median nerve and some of the flexor tendons away from one another, and away from electrosurgical elements 500. While creating a gap between the balloon 400, the sides of the electrosurgical elements 500, and the target tissue, the inflated balloon 400 has also applies sufficient tension to the transverse carpal ligament such that it is stretched taut across electrosurgical elements 500.

Embodiments of device 200, including bulb 420, may be anchored to the surrounding anatomy to stabilize and secure device 200 in position during the upcoming division process. In particular, in various embodiments, bulb 420 may be expanded, either before, concurrently with, or after expansion of the main portion of balloon 400, to engage anatomical features beyond the transverse carpal ligament. For example, the bulb 420 can share the same inflation pathway as the balloon 400 (e.g., 342) or it can have its own inflation pathway for separate inflation/control. Such engagement may act to prevent or minimize any tendency of device 200 to migrate, rotate, or otherwise move from a desired position and orientation within the carpal tunnel, thereby minimizing the chances of one or more of: accidentally damaging surrounding anatomical members (e.g., tissue, nerves), only partially dividing the transverse carpal ligament, or performing an imprecise or unclean division thereof It should be recognized that balloon 400 could also be inflated to a target pressure as opposed to target dimensions/target volume, for similar purposes as those described in this paragraph. The balloon 400 may be inflated to within a range of target pressures sufficient to cause balloon 400 to tension the ligament across electrosurgical elements 500 and form waist in the balloon for later indicating (e.g., via visualization or pressure change) when division is complete, as explained in more detail herein. For example, the balloon 400 can be inflated to a target pressure greater than 1 atmosphere. Regardless of the target pressure, the balloon 400 pressure should not exceed a rated burst pressure.

Referring now to FIG. 4B, electrosurgical element 500 may be energized to weaken a contacted portion of the tensioned transverse carpal ligament. This weakening, in combination with the tension applied by balloon 400, can cause the transverse carpal ligament to divide along the portion contacted by electrosurgical element 500, as shown. Device 200, in various embodiments, may be configured to perform multiple activations for a safer and more accurate division. For example, as discussed herein, the device 200 can be activated in pulses and/or repeated activated over short durations to prevent from excessive heating/damage to areas surrounding the target cutting area. The multiple activations can be performed to repeated cut at least a portion of the fibrous wall 110 until a complete division is achieved.

Figure 5A:
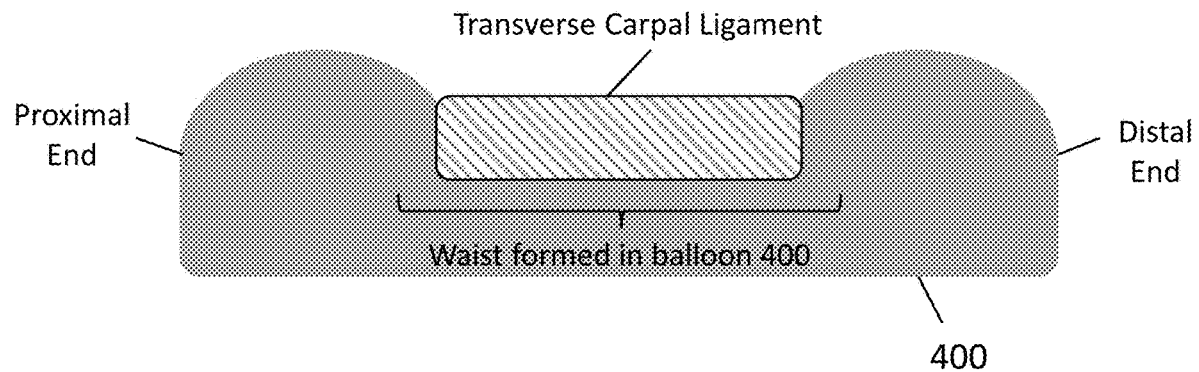
FIG. 5A schematically depicts shape deformation ("waisting") of the expandable member by the transverse carpal ligament, in accordance with another embodiment of the present disclosure.
Figure 5B:
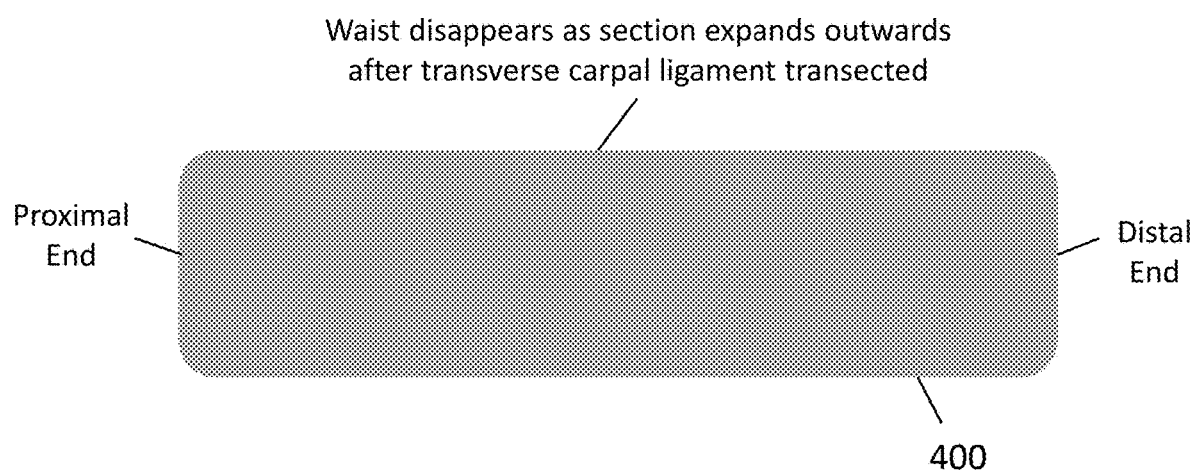
FIG. 5B schematically depicts shape return of the expandable member after division of the transverse carpal ligament, in accordance with another embodiment of the present disclosure.

Complete division of the transverse carpal ligament, in various embodiments, may be confirmed by any suitable technique known in the art. Referring ahead to FIGS. 5A and 5B, in some embodiments, deformations in balloon 400 during the procedure may be leveraged to confirm complete division. In particular, when balloon 400 is expanded to tension the transverse carpal ligament, the ligament exerts a reaction force on balloon 400, thereby squeezing the balloon and creating a "waist" or waisting effect along a length of the balloon 400. For example, creating a waisting effect along a central portion to create an hour glass like shape, as shown in FIG. 5A. This waisting shape of balloon (hour glass) can provide a visual indication/confirmation that a ligament is intact. The visual confirmation can be provided using any combination of methods, for example, through fluoroscopic, endoscopic, ultrasonic etc. visual confirmation. When the transverse carpal ligament is divided, the pressure exerted on the central portion of balloon 400 is released, thereby allowing the central portion of balloon 400 to expand outwards and resume a normal shape (e.g., a cylindrical, hot dog, etc. shape), as shown in FIG. 5B. In one such embodiment, various forms of imaging (e.g., fluoroscopic, ultrasonic, endoscopic, etc.) may allow for visualizing device 200, such that a surgeon may see when the waist in balloon 400 disappears, indicating/confirming complete division. More specifically, the visualization technique allows identification of anatomic variations (e.g., such as a transligamentous RMB) within the inserted space (e.g., carpal tunnel). In operation, once the physician confirms that no nerves or other tissues are within the treatment path, the device 200 can be used safely to divide the transverse the target tissue (e.g., carpal ligament). Should only a portion of the waist expand, while another portion remains deformed, it may indicate a partial division—that is, the portion of the transverse carpal ligament situated along the remaining deformed section has not been successfully divided.

As previously described, in some embodiments, the device 200 can include one or more sensors capturing a combination of measurables metrics. For example, referring back to FIGS. 2B and 2C, one or more pressure sensors in device 200 may be utilized to monitor internal pressure in balloon 400 to prevent activation at undesirable pressures. For example, it may be undesirable to activate electrosurgical elements 500 when balloon is at too low of a pressure for sufficiently tensioning the ligament. Likewise, it may be undesirable to activate electrosurgical elements 500 when balloon is at too high of a pressure because it could cause trauma to surrounding critical structures such as nerves or you could simply tear the ligament apart instead of cutting it. For example, for a desirable separation, the balloon 400 can be pressurized in a range of 0.5 atmosphere upwards to 10 atmospheres.

Additionally or alternatively, in another embodiment, the pressure sensor(s) may be configured to detect a change in pressure within balloon 400 corresponding with an expected reduction in pressure associated with complete division of the transverse carpal ligament. Prior to transection, expanded balloon 400 will have a first internal pressure resulting from the fluid used to expand balloon 400 and the squeezing of the transverse carpal ligament thereon. When the transverse carpal ligament is transected, the volume of balloon 400 increases as the waist disappears, resulting in a corresponding decrease in internal pressure to a second, lower internal pressure from the first, higher pre-transection pressure. Much like a partial transection may result in only a partial disappearance of the waist, a partial transection may result in only a partial reduction in pressure from the first pressure. One of ordinary skill in the art will recognize a magnitude of pressure reduction corresponding with complete transection without undue experimentation. Even still, tests were performed utilizing an embodiment of device 200 to transect bovine tissue to demonstrate an illustrative pressure decrease indicative of complete transection. In the tests, balloon 400 was inflated to a first pressure range of about 25-150 psi prior to transection, and instrument readings revealed that after complete transection, the pressure was reduced to a second pressure range of about 0-140 psi.

In various embodiments, one or more pressure sensors for measuring such pressure changes could be located in handle 210, in a separate device such as an insufflator (used to inflate balloon 400) or manometer in fluid communication with balloon 400, or on balloon 400 itself. In an embodiment, placement of the pressure sensor in handle 210 (e.g., coupled to PCB 218) may allow for housing of the pressure switch and indicator signal (e.g., feedback components 214) that will indicate that a pressure change has occurred.

In another embodiment, complete division of the transverse carpal ligament may be confirmed by measuring a change in force applied to balloon 400. Just as internal pressure decreases when the tensioned transverse carpal ligament is divided, there may be a measurable change in external force applied to balloon 400 upon transection. The transverse carpal ligament applies a local force along a contacted portion of balloon 400—in an embodiment, one or more force sensors may be positioned proximate electrosurgical leads 500 to detect when this local force is reduced. The force applied by the transverse carpal ligament may also press non-contacted portions of balloon 400 against other anatomical structures (e.g., median nerve, tendons), which in turn apply local forces. In an embodiment, one or more force sensors may be positioned on corresponding portions of balloon 400 to detect the forces exerted on balloon 400 by these anatomical structures as a result of force applied by the in-tact transverse carpal ligament. When transected, these forces may be reduced, indicating that transection was successful. In a representative embodiment, balloon 400 may be inflated to about ≥2 atm with an in-tact transverse carpal ligament and, when transected, will drop by about ≥25% or to a pressure of about ≤1.5 atm.

In still another embodiment, complete division of the transverse carpal ligament may be confirmed by measuring a change in electrical feedback from electrosurgical elements 500, for example, as discussed with respect to FIGS. 3E-3I. For example, the PCB 218 can be configured for detecting an open circuit (e.g., between electrodes 500) that occurs for a brief period of time after the ligament is transected. An increase in impedance may occur as a result of water loss in the tissue. This tissue desiccation is often associated with tissue death resulting in cutting of the transverse carpal ligament and an associated rapid, steep spike in impedance when the current is then exposed to the overlying fatty tissue with a much lower water content. For example, during testing impedance during cutting of the TCL ranged from 400-800 ohms with a spike to 1600-2000 ohms once the TCL was divided and the electrical current was exposed to the overlying fatty tissue. In another example, the PCB 218 can be configured to monitor a magnitude of impedance in the electrosurgical circuit to detect when transection occurs. In particular, the circuit may monitor for a threshold level of impedance and/or for a threshold rate of change in impedance associated with transection. In still another example, device 200 may include an integrated circuit configured to monitor a magnitude of power delivered by electrosurgical elements 500 to detect when the power magnitude increase because if increased impedance and terminate the power delivery at a predetermined threshold.

Referring now to FIG. 4C, upon confirming complete transection (or otherwise desired level of transection) of the transverse carpal ligament balloon 400 may be subsequently deflated, and device 200 removed, allowing pressure to escape the carpal tunnel through the transected transverse carpal ligament, thereby relieving carpal tunnel syndrome.

Methods for Positioning Minimally-Invasive Division Devices 200, 700

Various methods for positioning minimally-invasive division devices 200, 700 within anatomical compartment 100 using a fluoroscopic or other imaging technique are now disclosed. As before, for ease of explanation, the following methods for positioning devices 200, 700 will be explained in the context of using device 200, though it should be recognized that similar methods may be employed using device 700 within the scope of the present disclosure.

In some embodiments, the devices 200, 700 can be provided as a complete system or device or part of a kit to be configured for a procedure (e.g., treating carpal tunnel syndrome). In some embodiments, the kit can include a guide wire 1802, a protective jacket 1804, a pressure inflation endoflator with gauge, an iodinated contrast solution, saline, fluoroscopy, an endoscope, an electrosurgical unit, and any other combination of devices that may be used as part of a given procedure (e.g., carpel tunnel procedure).

In a representative procedure, the hand and wrist are positioned with the palm up and the wrist in a semi-extended position, as shown in FIGS. 1A-1E, and secured. The anatomy of the particular patient's wrist and carpal tunnel are determined using physical exam, direct visualization, endoscopy, ultrasound, and/or fluoroscopy techniques. For example, defining the anatomy using a physical exam may involve, at least in part, palpating the radial and ulnar pulses, and localizing the wrist crease, thenar and hypothenar eminences. Visualization methods such as direct visualization, endoscopic visualization, ultrasound, and/or fluoroscopy may be used to define the carpal tunnel using the proximal extent of the pisiform and scaphoid bone as the proximal limit, the distal extent of the hamate bone and the trapezium bone as the distal limit, the medial extent of the hamate and pisiform bones as the medial limit, and the lateral extent of the scaphoid and trapezium bone as the lateral extent. This can help ensure anatomical variance (e.g., confirming the position of a nerve relative to the ligament) before advancing devices 200, 700 to the site of division.

Optionally, to clearly identify and mark the following anatomical landmarks prior to elevating the tourniquet, a finder needle may be inserted into the skin at the level of the wrist crease, approximately 1 cm-2 cm proximal to the thenar eminence, parallel to the long axis of the forearm and may be directed using both palpation and fluoroscopy under the transverse carpal ligament just to the medial side of the scaphoid and trapezium bones. An entry site can be marked, for a 1-2 cm incision at or just proximal to the proximal wrist crease. If the incision is transvers it should extend from the radial edge of the palmaris longus extending toward the radial side of the wrist. If the incision is longitudinal it should be placed along the radial edge of the palmaris longus centered on the wrist crease. Similarly, the exit site can be marked from the center of the entry site mark, for example, by measuring approximately 6 cm directly toward the base of the ring (forth) finger and mark the skin to approximate the exit site. To avoid the superficial palmar arch ensure that the exit site is proximal to a line can be drawn across the hand from the distal border of the fully abducted thumb through the center of the palm and at the same level of the distal edge of the TCL.

Ultrasound guidance may be used concomitantly to ensure the path of the finder needle traverses the carpal tunnel just below the transverse carpal ligament, which is kept anterior to the needle, and that the medial nerve and flexor tendons all remain posterior to the path of the finder needle.

Figure 6A:
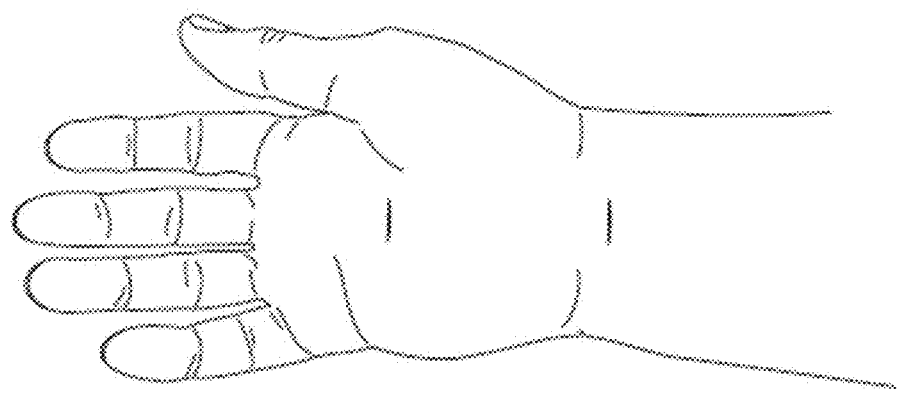
FIGS. 6A, 6B, 6C, 6D, 6E, 6F, 6G, 6H, and 6I are illustrative views of an example process for insertion of a device during a procedure, in accordance with an example of the present disclosure.

The needle may be advanced posterior to the transverse carpal ligament and anterior to the median nerve and flexor tendons, and completely transverse to the carpal tunnel and transverse carpal ligament. Once the distal extent of the ligament has been cleared by ultrasound (i.e., entire ligament is anterior to the needle) and fluoroscopy (i.e., needle travels from the proximal boney landmarks past the distal boney landmarks), it may be directed to exit the skin just distal to the thenar eminence and proximal to the arterial palmar arch, which may be seen with various forms of visualization (e.g., ultrasound or fluoroscopy). In some embodiments, addition to using a needle to gain access and insert a wire, an incision can be created at the wrist and at the palm and dissecting the tissue using an instrument, for example, as shown in FIG. 6A. Thereafter, a guidewire 1802 can be inserted at the palm incision using the instrument and pass it through until it exits out of the wrist incision, as discussed in greater detail herein.

A guide wire 1802 may then be optionally placed through the needle and the needle removed, leaving the guide wire 1802 in place entering the skin at the wrist, traversing the carpal tunnel, posterior to the transverse carpal ligament, anterior to the median nerve and flexor tendons, and exiting the skin in the palm proximal to the palmar arch.

A sizing balloon may optionally be placed over the guide wire 1802 and advanced forward until the tip of the catheter is at the skin level on the palmar surface and/or the electrodes of the catheter are confirmed to completely traverse the transverse carpal ligament, which may be confirmed by ultrasound and fluoroscopy. The sizing balloon can be used to assist in determining the size of the carpel tunnel and further the size of the balloon 400 that should be used for the procedure. The sizing balloon may then be inflated to about 2 atm—10 atm and lateral images may be obtained using fluoroscopy, looking for narrowing or "waisting" of the balloon as it conforms to the carpal tunnel, expanding to fill the larger proximal and distal ends of the hour glass shape and remaining more narrow in the middle due to the smaller diameter of the carpal tunnel in the mid-section as described previously. If "waisting" is achieved then the appropriate size balloon is confirmed. If no "waisting" is achieved then a larger balloon is used following the sizing procedure until "waisting" is achieved and the correct balloon size determined and the sizing balloon removed leaving the guide wire 1802 in place.

Optionally, in an embodiment, the carpal tunnel space may be pre-dilated with a balloon catheter prior to advancing devices 200, 700, while in another embodiment, balloons 400, 900 of devices 200, 700 respectively may be partially inflated during positioning for similar purposes.

Minimally-invasive device 200 may now be inserted and advanced to the surgical site. An appropriate sized balloon 400 may optionally be placed over the guide wire 1802 and advanced forward until the tip of catheter 300 is at the skin level on the palmar surface and/or the electrodes are confirmed to completely traverse the transverse carpal ligament, which may be confirmed by ultrasound and fluoroscopy. It should be recognized that fluoroscopy and/or ultrasound may be used to help guide device 200 to the surgical site without the use of a finder needle or guide wire 1802.

Alternatively, over the guide wire 1802 in a retrograde fashion a 10-26 French(f) protective jacket 1804 or sheath can be place over the guide wire 1802, as discussed in greater detail with respect to FIGS. 6A-6I and 10A-10G. To assist in the insertion of the guide wire 1802 and a protective jacket 1804, small skin incisions may be required to enlarge the skin entrance site for insertion. The entry site and exit site can be created using any combination of incision methods through the skin. The entry site and exit site incisions can be used to advance a guide wire 1802 and then the protective jacket 1804 can be advanced over the guide wire 1802 and across the carpal tunnel. The obturator of the protective jacket 1804 can then removed and, in an antegrade fashion, catheter 300 may be placed over the guide wire 1802 and advanced into the protective jacket 1804. The catheter 300 can be advanced using any combination of methods, for example, using fluoroscopy, ultrasound or direct visualization, balloon 400 and electrodes 500 on the catheter 300 are moved into the appropriate position. With catheter 300 in position and held securely, the protective jacket 1804 can be withdrawn leaving only catheter 300 in place.

In some instances, conditions my cause tendons (e.g., carpel tendon) or other surrounding tissues to become narrower or swollen, making it difficult to insert the catheter 300 of the device 200 under the tendon for a procedure. The systems and methods discussed with respect to FIGS. 6A-6I can assist with safe placement of the device 200 for a procedure. Referring to FIGS. 6A-6I, in some embodiments, the minimally-invasive division device 200 of the present disclosure may be used as part of a system 1800 or kit which can include a combination of the guide wire 1802, the protective jacket 1804, and dilator 1806. Using some combination of the guide wire 1802, the protective jacket 1804, and the dilator 1806 can be used to prep an area for insertion of the distal end of the device 200. Although the embodiments discussed with respect to FIGS. 6A-6I are discussed with respect to device 200, catheter 300, balloon 400, and the leads 510 and 520 the same features can be applied to the device 700, catheter 800, balloon 900, with the leads 1010 and 1020.

In some embodiments, the guide wire 1802 can be used to provide guidance of the protective jacket 1804, and the dilator 1806, and the device 200 into position within an incision site. The incision site can be made through the skin at a previously marked entry site and can be created using precise, gentle dissection, identify the radial edge of the palmaris longus, the proximal edge of the palmar fascia, the ulnar bursa and visualize the underlying median nerve. In some embodiments, under direct or endoscopic visualization, and ensuring the dissection plane remains in the extrabursal space, elevate the palmar fascia working distally until the proximal edge of the transverse carpal ligament is identified. Continue the dissection distally into the carpal tunnel and toward the planned exit site mark. Caution should be taken to ensure that the plane of dissection remains in the extrabursal space releasing the tenosynovium from the posterior surface of the TCL AND that the median nerve and bursal contents are reflected posteriorly. Ensure that the dissection plane and intended path for the guide wire 1802 and subsequently the device 200 remains directly over the median nerve so that upon balloon 400 inflation the median nerve remains posterior to the electorodes 500 at the 6 o'clock position beneath the balloon 400 and maximally protected during cutting.

Figure 6B:
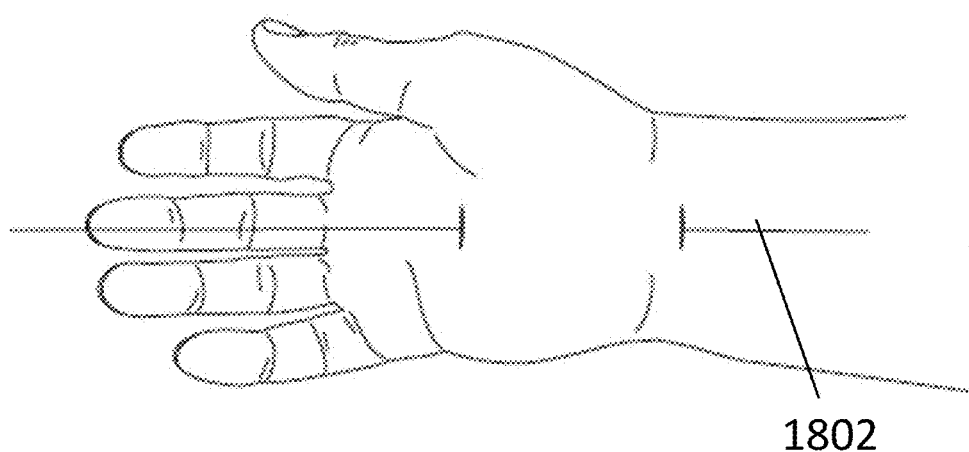

In some embodiments, the guide wire 1802 can be positioned and inserted through a first insertion site through a procedure location and out a second incision or exit site, as depicted in FIGS. 6A and 6B. the guide wire/k-wire can be positioned directly posterior to the TCL, that the median nerve is directly posterior to the guide wire and that tendons and vascular structures remain within the ulnar bursa and free from and posterior to the guide wire 1802 (or k-wire). The guide wire 1802 can optionally be removed at any stage of the insertion of the device 200 into a procedure area. In some embodiments, the guide wire 1802 can remain in place until an under of the procedure and can be used to provide guidance of the protective jacket 1804, and the dilator 1806, and the device 200 for removal out of an incision site.

Figure 6C:
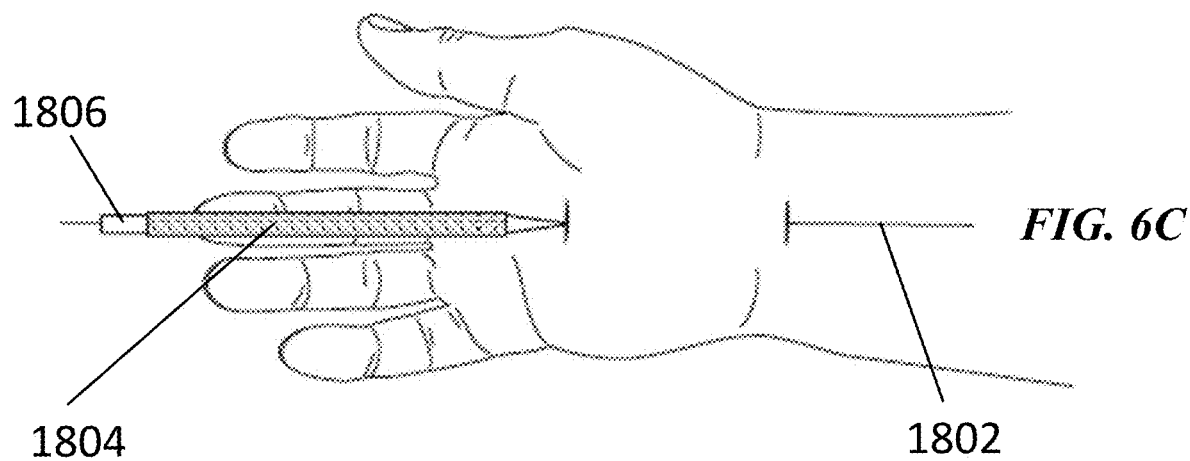
Figure 6D:
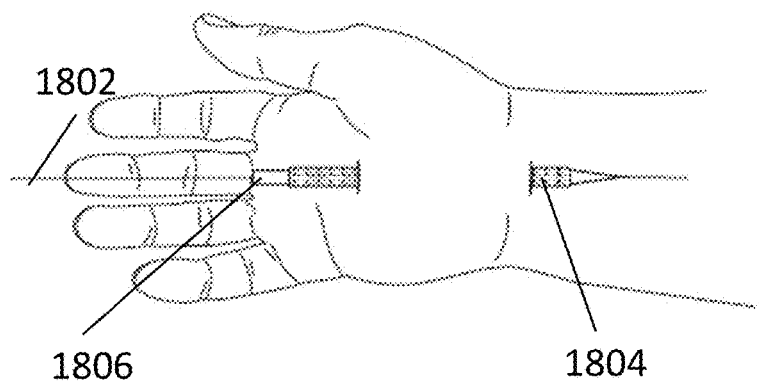
Figure 6E:
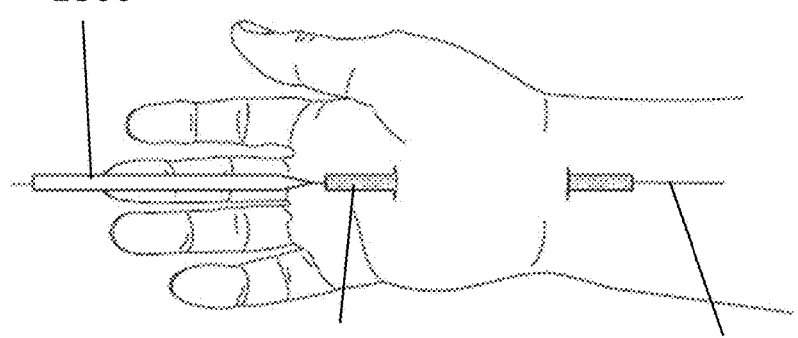
Figure 8A:
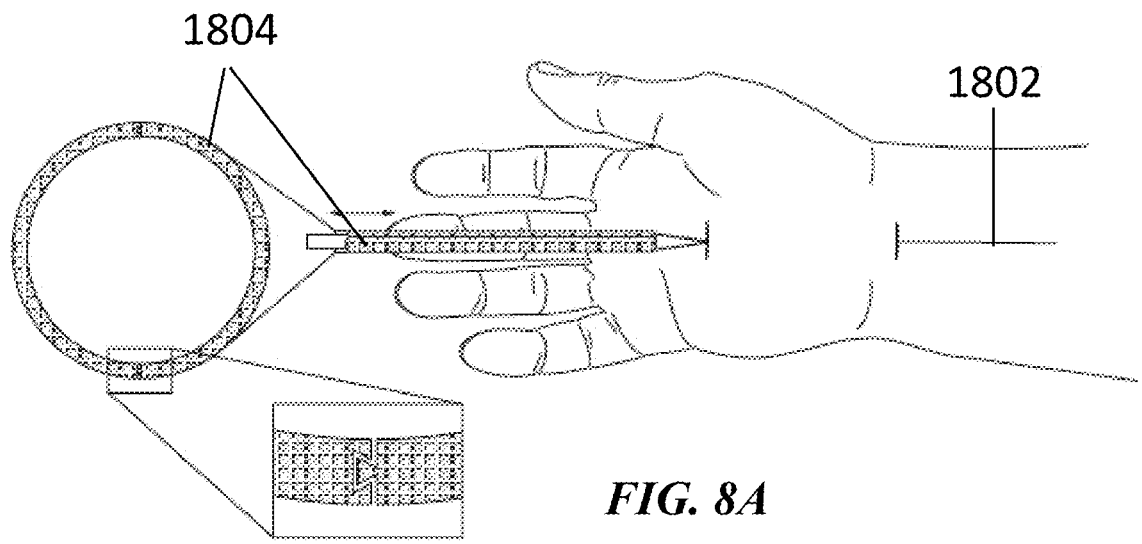
FIGS. 8A, 8B, and 8C are illustrative views of an example process for removing a sheath from a device during a procedure, in accordance with an example of the present disclosure.
Figure 8B:
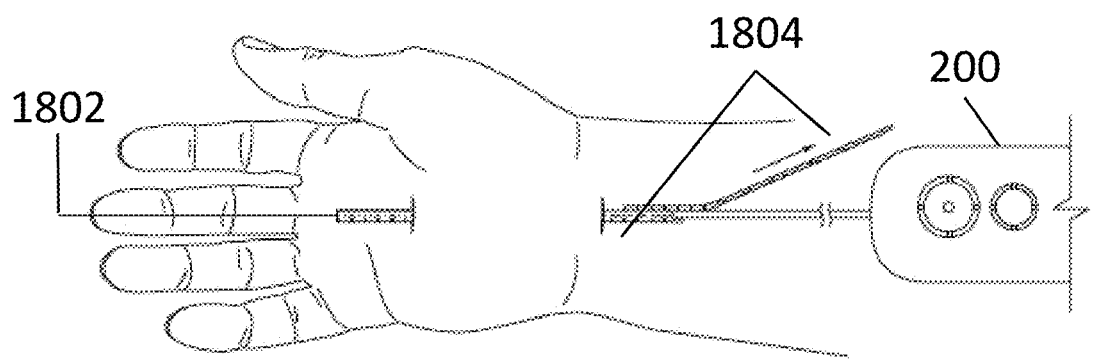
Figure 8C:
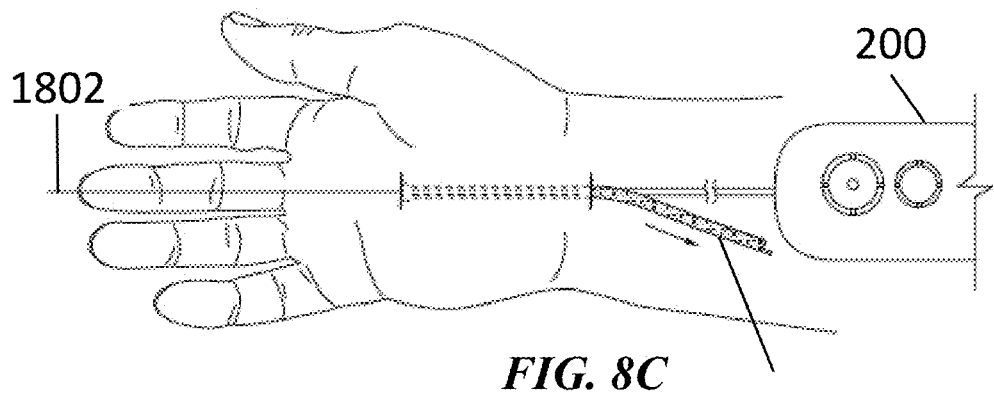

Referring to FIGS. 6C, 6D, 8A, and 8B in some embodiments, the dilator 1806 (or inducer) may be inserted over the guide wire 1802 for dilation of a procedure area (e.g., the palm). For example, the dilator 1806 can be inserted to create an initial elevation of the carpal ligament tissue plane. The dilator 1806 can be designed for insertion in either direction. For example, the dilator 1806 can be inserted in an insertion site near the fingers and out another insertion site near the wrist (as shown in FIGS. 6C-6D) or the dilator 1806 can be inserted in an insertion site near the wrist and out another insertion site near the fingers (as shown in FIG. 8A). Similarly, dilator 1806 can be designed for removal from the procedure area in either direction. For example, the dilator 1806 can be removed from the procedure area through an insertion site near the fingers (as shown in FIG. 6E) or the dilator 1806 can be removed from the procedure area through an insertion site near the wrist (as shown in FIG. 8C). The insertion and removal of the dilator 1806 do not necessarily have to be performed in a same direction.

In some embodiments, at least one end of the dilator 1806 can have a tapered tip. The tapered tip(s) can be used to assist in the insertion and/or removal of the dilator 1806 through an incision site, thereby minimizing tissue trauma, and through a procedure location. In some embodiments, the dilator 1806 can have a smooth surface to assist in the insertion process. In some embodiments, the dilator 1806 may be made of a flexible plastic material such as polyurethane, polyethylene or flourothermoplastic, among other suitable plastics. The dilator 1806 may be made of any biocompatible material including plastic or metal. In some embodiments, the dilator 1806 may be appropriately sized between about 12 Fr and about 16 Fr, but could be as large as about 18 Fr to about 26 Fr.

Referring to FIGS. 6C and 6D, in some embodiments, the dilator 1806 can be inserted along with the protective jacket 1804. In other embodiments, the protective jacket 1804 can be inserted after the dilator 1806 has been placed within the procedure area. Regardless of insertion order, the protective jacket 1804 can be sized and shaped to be inserted over the dilator 1806 while allowing the dilator 1806 to be removed from within the protective jacket 1804 once the protective jacket 1804 is in place. Once the protective jacket 1804 is in place, for example, within the palm as shown in FIGS. 6D and 8B, the dilator 1806 can be removed.

In some embodiments, the use of the jacket 1804, alone or in combination with an dilator 1806, can be used to assist the insertion and placement of the device 700 to a desired location. The protective jacket 1804 can also be sized and shaped to surround and provide a channel for insertion of the distal end of catheter 300 including the balloon 400 and the one or more electrosurgical elements 500 (e.g., a combination of 510, 520, 530) into the procedure area. In some embodiments, the jacket 1804 can be a substantially cylindrical shape with open ends on both ends of the device. The jacket 1804 can be can include any combination of shapes and sized without departing from the scope of the present disclosure. For example, the jacket 1804 can be substantially cylindrical, rectangular, polygonal, etc.

In some embodiments, the protective jacket 1804 can be designed to be sufficiently rigid to maintain its shape and not collapse after the dilator 1806 has been removed. The jacket 1804 may be made of any biocompatible material including plastic or metal. In an embodiment, the jacket 1804 may be made of a flexible plastic material such as polyurethane, polyethylene or flourothermoplastic, among other suitable plastics. In an embodiment jacket 1804 may be sufficiently rigid to facilitate minimally-invasive insertion and to guide device 200 through the body and to the site of treatment, while also being sufficiently flexible enough to accommodate partial flexion of the wrist or other body parts.

In operation, referring to FIGS. 6A-6I, a combination of the guide wire 1802, the protective jacket 1804, and the dilator 1806 can be used to assist in the safe and efficient insertion of the device 200 to a target procedure area below the skin for a carpel tunnel procedure. Initially, as shown in FIG. 6A, two incisions can be made within a palm of a patient. For example, one incision can be made near the wrist and another can be made near a middle of the palm. The incisions should be located on either side of a target site for performing the carpel procedure. In some embodiments, the guide wire 1802 can be inserted into one of the incisions, through the procedure area below the skin (e.g., within the carpel tunnel), and out the opposing incision, as shown in FIG. 6B.

Referring to FIG. 6C, with the guide wire 1802 in place, a combination of the dilator 1806 with the protective jacket 1804 around the dilator 1806 can be provided across the guide wire 1802 and inserted into one of the incisions. For example, as shown in FIG. 6C, the dilator 1806 and the protective jacket 1804 can be inserted within an incision near the middle of the palm. The dilator 1806 and the protective jacket 1804 can be inserted and advanced through the target procedure area out the opposing incision, as shown in FIG. 6D. With the dilator 1806 and the protective jacket 1804 in place, under the skin and extending through both incisions, the dilator 1806 can be removed, leaving the protective jacket 1804 in place, as shown in FIG. 6E.

Figure 6F:
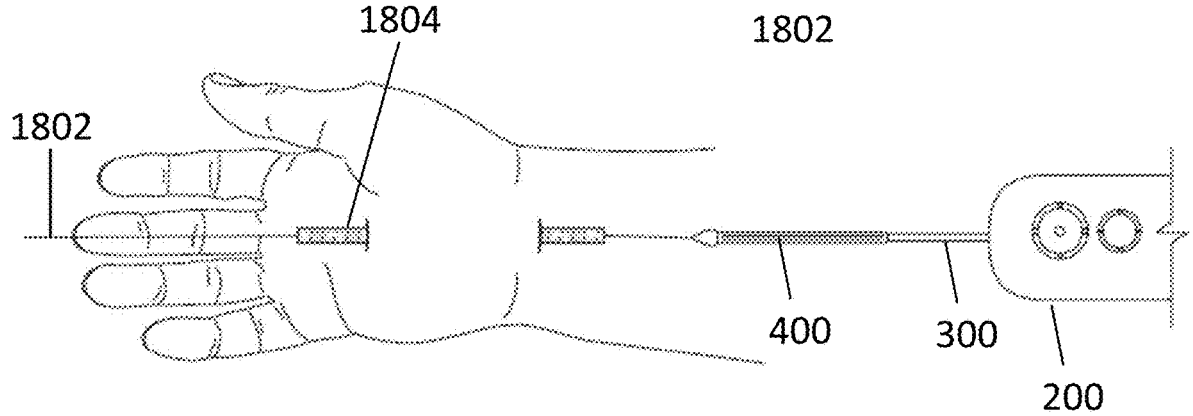
Figure 6G:
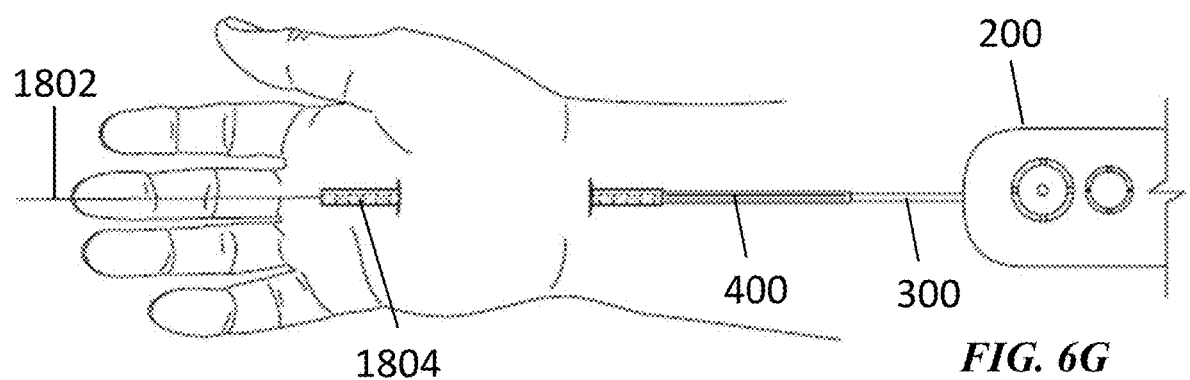
Figure 6H:
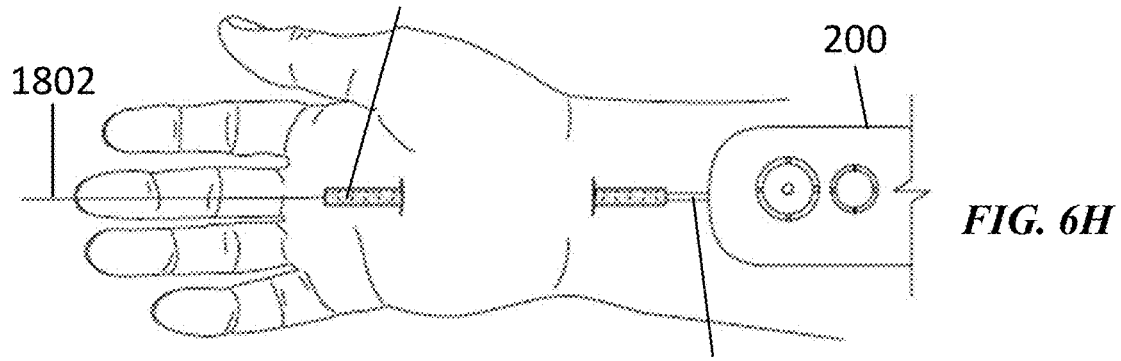
Figure 6I:
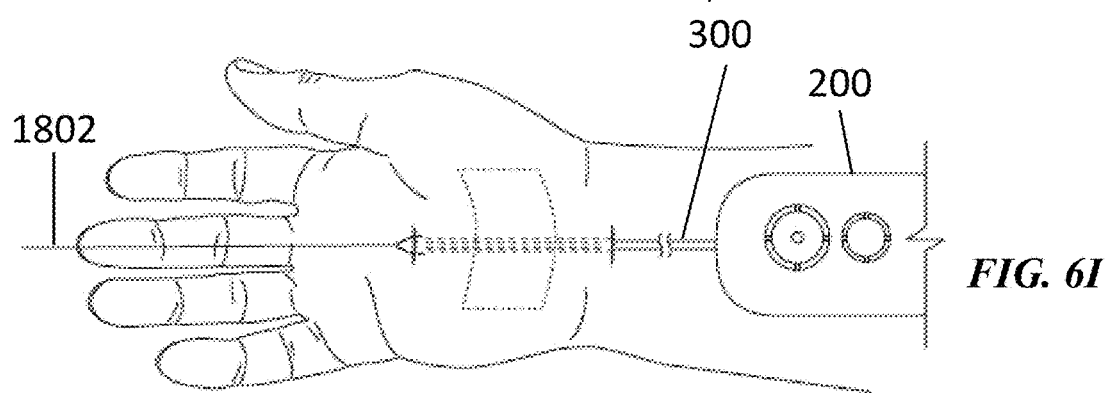

Referring to FIG. 6F, with the protective jacket 1804 in place maintaining a pathway for receiving a distal end of the device 200, the device 200 can be advanced over the guide wire 1802 into the protective jacket 1804, as shown in FIGS. 6F and 6G. The protective jacket 1804 can be designed to maintain its position under the skin as the device 200 is advanced therein. When the distal end of the device 200 is in place within the protective jacket 1804 (as shown in FIG. 6H), the protective jacket 1804 can be removed. For example, the protective jacket 1804 can be withdrawn over the guidewire out one of the incision sites. In some embodiments, the distal end of the device 200 can be used to push the protective jacket 1804 out of the procedure area. For example, at least a portion of the distal end of the device 200 can be larger than the diameter of the channel within the protective jacket 1804, such that when it contacts the protective jacket 1804 it will push the protective jacket 1804. The result of the steps discussed with respect to FIGS. 6A-6H, the distal end of the device 200, including the electrodes 500 and balloon 400, will be positioned under the skin proximal to the transcarpal ligament, as shown in FIG. 6I. With the device 200 in position, visual and/or electronic confirmation can be performed for proper placement prior to performing the procedure. For example, the user can visually confirm using a fluoroscopy and/or use the nerve sensing and detection methods discussed herein for an electrical confirmation. Additionally, the tip of the device 200 can be sized and shaped to extend out of an incision to provide a visual cue of placement to a user.

Figure 7A:
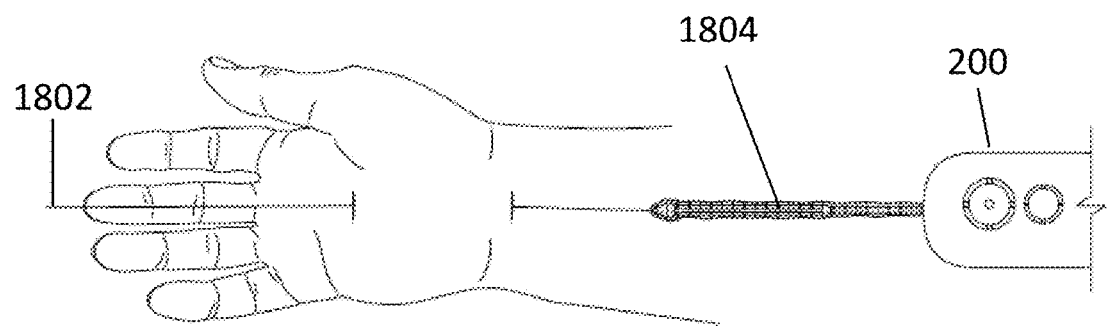
FIGS. 7A, 7B, and 7C are illustrative views of an example process for insertion of a device during a procedure, in accordance with an example of the present disclosure.

Referring to FIG. 7A, in some embodiments, the protective jacket 1804 can be designed to be positioned over the distal end of the device 200 prior to insertion into the procedure area. The protective jacket 1804 can be a flexible material that fits over the distal end of the device 200 and then the combined protective jacket 1804 and device 200 can be inserted over a guide wire 1802 into one of the incisions into the procedure area. The flexible protective jacket 1804 can be sufficiently flexible to allow entry of the distal end of the device 200 such that the device 200 does not get caught on tissue. Once in place, the protective jacket 1804 can be removed through one of the incision sites, for example, using a tether or pulling the protective jacket 1804 itself. In some embodiments, the flexible protective jacket 1804 can be constructed from or coated with any combination of friction reducing materials, such as for example, PTFC materials, having a Teflon coating, having lubrication, etc.

Figure 7B:
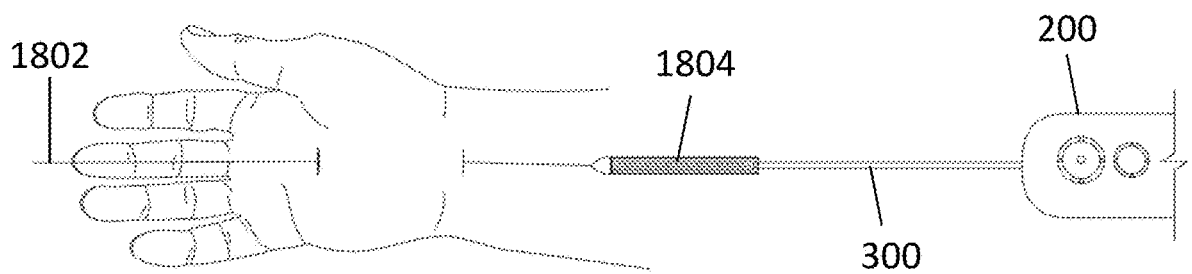

Referring to FIGS. 7A and 7B, in some embodiments, the distal end of the device 200 can include a tapered tip to assist in advancement of the device 200 and the sheath 1804 into the procedure area. The tapered tip can complement a flexible protective jacket 1804 such as shown in FIG. 7A or it can extend out of an end of a more rigid protective jacket 1804 as shown in FIG. 7B.

Figure 7C:
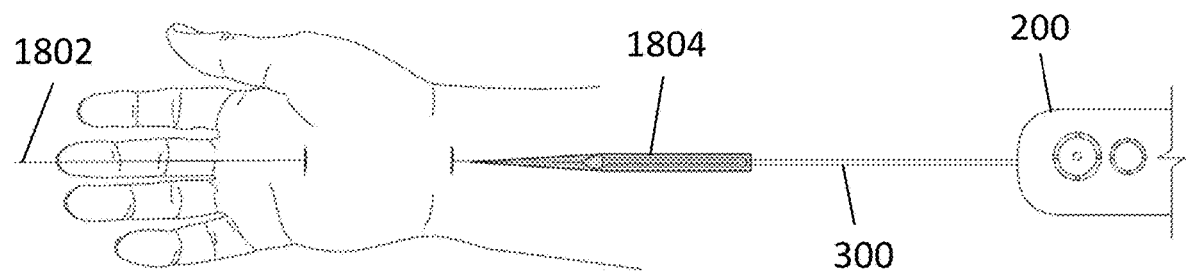

Referring to FIG. 7C, in some embodiments, the protective jacket 1804 can be designed to have a tapered tip positioned over the distal end of the device 200 prior to insertion into the procedure area. The tapered tip of the protective jacket 1804 can act as both a protective jacket and a dilator. In this implementation, the protective jacket 1804 can be designed to be inserted into a procedure area without the assistance of a dilator 1806.

Different designs of the protective jacket 1804 can be designed to be removed from the distal end of the device 200 in either direction out one of the incisions. In some embodiments, the protective jacket 1804 can be removed from the procedure area toward the device 200 and remain on the catheter 300 of the device 200 during the procedure. When using the optional guide wire 1802, the protective jacket 1804 can include a hole on either side to enable shifting over the guide wire 1802. In some embodiments, the jacket 1804 can be designed as a telescopic component of the device 200 and extend from within the device 700 body to extend over the tip the device 200 during insertion.

In some embodiments, the jacket 1804 can be coupled to a tether and/or guidewire for removing the jacket 1804 from the device 200 when the device 200 is in position. In some embodiments, when the jacket 1804 is designed for removal in the proximal direction, an open ended jacket 1804 can be used also assist in facilitating the removal of the jacket 1804 through the body in the way that the device 700 entered the body (e.g., over the catheter).

Referring to FIG. 8A-8C, in some embodiments, the protective jacket 1804 can be designed to be removed from the procedure area in multiple parts. As shown in the cross-sectional front view of FIG. 8A, the protective jacket 1804 can be constructed by two interconnecting parts. The protective jacket 1804 constructed from two interconnecting parts can be designed for insertion over a dilator 1806 and/or the distal end of the device 200. Referring to FIGS. 8B and 8C, in some embodiments, the interlocking parts can be designed to be removed from the procedure area in pieces. For example, one of the two interconnecting parts can be removed, as shown in FIG. 8B, followed by the second part, as shown in FIG. 8C. Similar to other protective jacket 1804 designs discussed herein, the designs of protective jacket 1804 that are removable in parts can be removed in either direction from the procedure area.

Figure 9A:
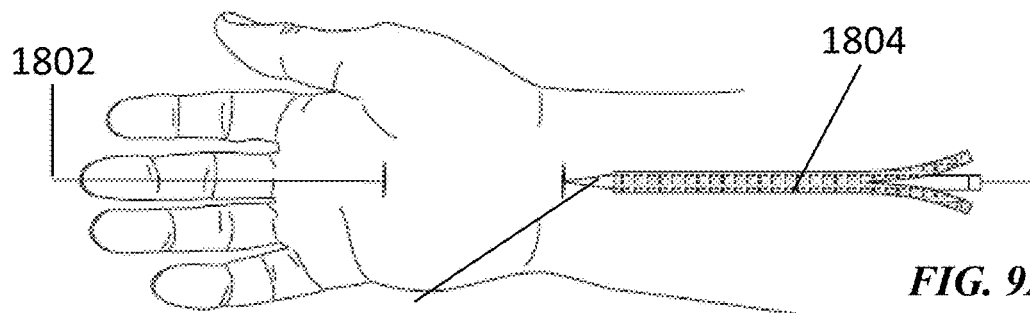
FIGS. 9A, 9B, 9C, 9D, 9E, 9F, and 9G are illustrative views of an example process for insertion of a device during a procedure, in accordance with an example of the present disclosure.

Referring to FIGS. 9A-9G, in some embodiments, the protective jacket 1804 can be pre-scored and/or pre-split such that is the protective jacket 1804 has a weak point that will separate as the two halves as pulled away from one another. In operation, referring to FIGS. 9A-9G, a combination of the guide wire 1802, the protective jacket 1804, and the dilator 1806 can be used to assist in the safe and efficient insertion of the device 200 to a target procedure area below the skin for a carpel tunnel procedure. Initially, as shown in FIG. 9A, two incisions can be made within a palm of a patient as discussed with respect to FIG. 6A. In some embodiments, the guide wire 1802 can be inserted into one of the incisions, through the procedure area below the skin (e.g., within the carpel tunnel), and out the opposing incision.

Figure 9B:
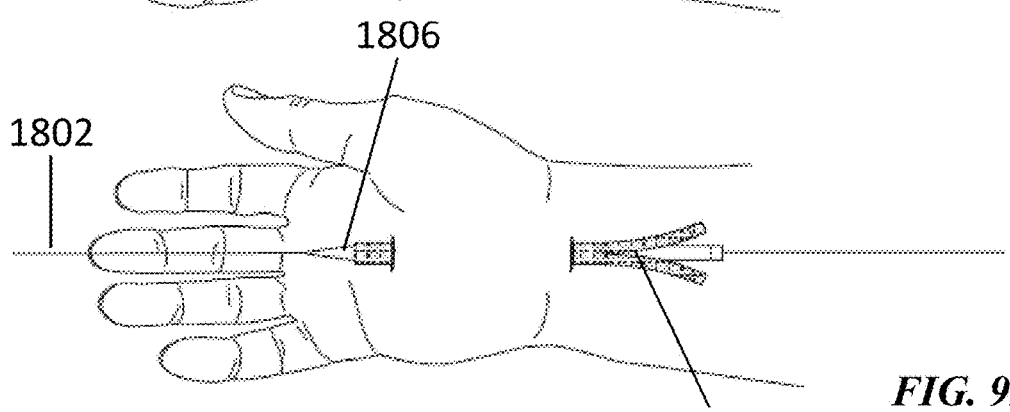
Figure 9C:
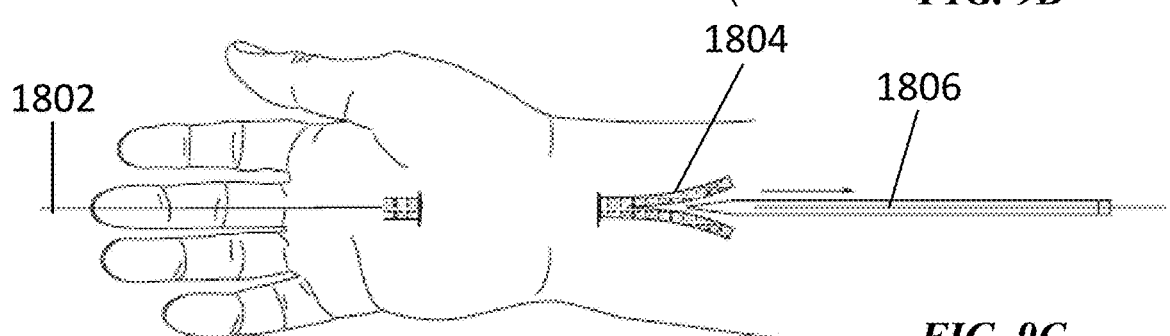
Figure 9D:
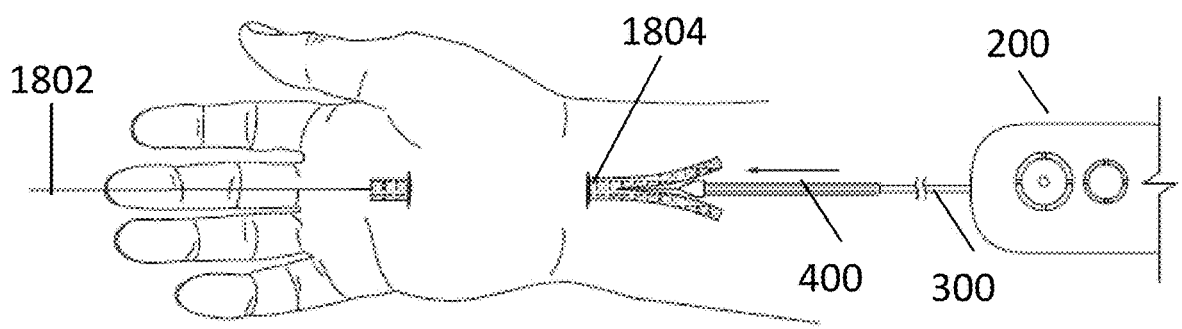
Figure 9E:
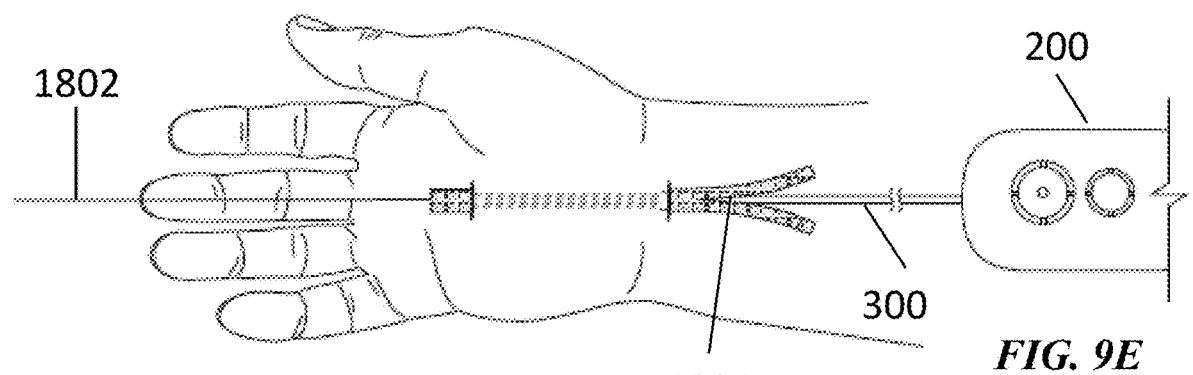

Referring to FIG. 9A, with the guide wire 1802 in place, a combination of the dilator 1806 with the pre-split protective jacket 1804 around the dilator 1806 can be provided across the guide wire 1802 and inserted into one of the incisions. For example, as shown in FIG. 6C, the dilator 1806 and the protective jacket 1804 can be inserted within an incision near the middle of the palm. The dilator 1806 and the protective jacket 1804 can be inserted and advanced through the target procedure area out the opposing incision, as shown in FIG. 9B. With the dilator 1806 and the protective jacket 1804 in place, under the skin and extending through both incisions, the dilator 1806 can be removed, leaving the protective jacket 1804 in place, as shown in FIG. 9C Referring to FIG. 9D, with the protective jacket 1804 in place maintaining a pathway for receiving a distal end of the device 200, the device 200 can be advanced over the guide wire 1802 into the protective jacket 1804, as shown in FIGS. 9D and 9E. The protective jacket 1804 can be designed to maintain its position under the skin as the device 200 is advanced therein. When the distal end of the device 200 is in place within the protective jacket 1804, the protective jacket 1804 can be removed.

Figure 9F:
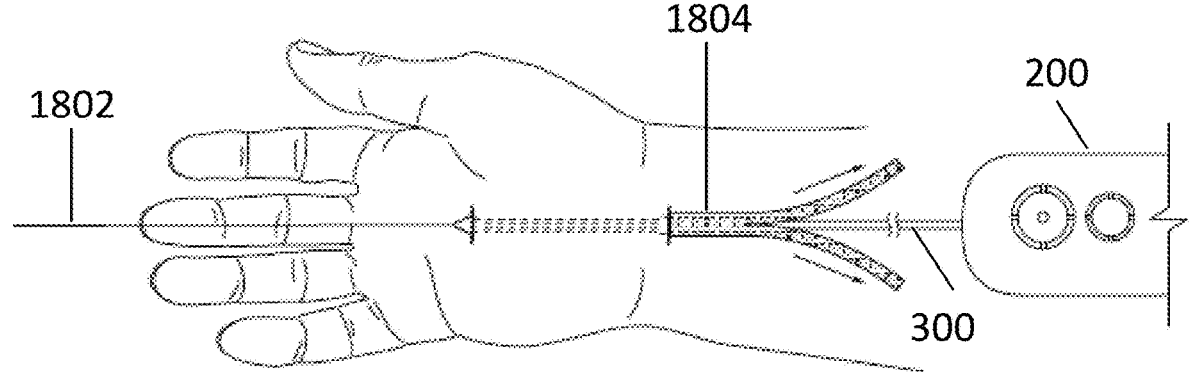
Figure 9G:
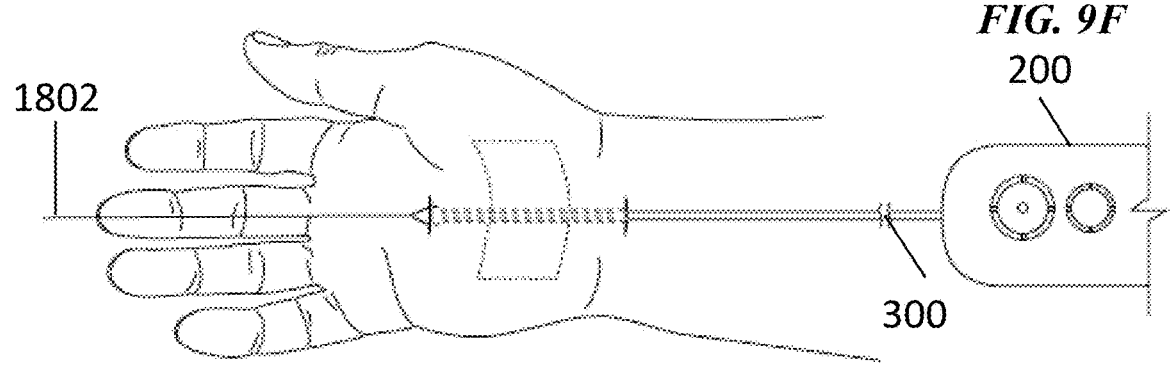

Referring to FIG. 9F, in some embodiments, the protective jacket 1804 can be withdrawn by pulling the opposing ends of the pre-split end of the jacket 1804. As the pre-split ends are pulled away from one another, the jacket 1804 will be split further in half as it is removed. The result of the steps discussed with respect to FIGS. 9A-9F, the distal end of the device 200, including the electrodes 500 and balloon 400, will be positioned under the skin proximal to the transcarpal ligament, as shown in FIG. 9G. With the device 200 in position, visual and/or electronic confirmation can be performed for proper placement prior to performing the procedure. For example, the user can visually confirm using a fluoroscopy and/or use the nerve sensing and detection methods discussed herein for an electrical confirmation. Additionally, the tip of the device 200 can be sized and shaped to extend out of an incision to provide a visual cue of placement to a user.

Regardless of systems and methods for inserting the device 100 to a procedure area, once the final position of device 200 is confirmed it may be attached to the electrical/nerve stimulator cable and the inflation line. In some embodiments, the balloon 400 may be inflated with air or any other suitable fluid to 2 atm—10 atm and using ultrasound guidance as well as fluoroscopy, "waisting" of the balloon ensured and a stable position of the catheter is maintained. Prior to inflation, a user can ensure that the device 200 is in the desired position and that no part of the balloon 400 is extending outside of the entrance or exit incisions. Once versified, the balloon 400 can be prepared for inflation using any combination of methods. For example, an endoflator can be attached to a luer fitting on device 200 and can be used to slowly inflate the balloon 400, allowing the distal end of the balloon 400 to inflate first and stabilize the device 200 position until the proper pressure range (2-10 ATM) has been achieved.

In some embodiments, the device can have an automatic and obligatory 10-minute time limit for balloon inflation. This is a continuously running timer can be initiated once the balloon is inflated to a predetermined threshold (e.g., >2 ATM)and paused when balloon pressure is at another predetermined threshold (e.g., <2 ATM.) If this 10-minute time limit has been reached, the user may decrease balloon pressure to <2 ATM for 10 minutes. After 10 minutes has passed the device may be ready for additional use. If at any point during the 10 minute recovery timer the balloon is inflated to the predetermined threshold (e.g., >2 ATM), the recovery timer will reset. Thereafter, the device 200 can be used to perform the procedure, for example, as discussed with respect to FIGS. 4A-4C.

In various embodiments, an elongated, flat tool similar to a tongue depressor or a ribbon retractor may be inserted and used to manipulate anatomical structures (e.g., nerves) out of the way of electrosurgical elements 500 or to prevent anatomical structures from sliding towards electrosurgical elements 500 along the surface of balloon 400 during inflation. The tool, in some embodiments, may be substantially flat and either rigid or semi-rigid, and may come in various sizes to accommodate different sized patients and patients with varying anatomies. In various embodiments, balloon 400 may be partially inflated with the tool in place, at which point the tool may be removed if it appears there is no longer danger of an anatomical structure such as a nerve now migrating over or proximate to electrosurgical elements 500, while in other embodiments, the tool may be left in place during division.

In various embodiments, the nerve stimulatory circuit may be activated and median nerve stimulation assessed. For example, in a carpal tunnel surgical procedure, it may be desired to position device 200 between the transverse carpal ligament and the median nerve, with any combination of the electrosurgical elements 510, 520, 530 directed towards the transverse carpal ligament. If electrosurgical elements 510, 520, 530 provide feedback indicating that the nerve is in that vicinity, an operator may deduce that: 1) balloon 400 is properly oriented, but improperly positioned under the median nerve, rather than between it and the transverse carpal ligament, or 2) balloon 400 is properly positioned, but improperly oriented with electrosurgical elements 510, 520, 530 facing the median nerve rather than the transverse carpal ligament. If the nerve stimulation test is negative and proper position of the electrode and waisting of balloon 400 are confirmed by ultrasound and fluoroscopy, then the cutting elements 510, 520, 530 can be engaged by activating the switch on handle 210. In some embodiments, the device 200 can indicate when the device 200 is ready for cutting, for example, using an indicator light.

During and after the cut is performed, the pressure may be monitored both manually and via the pressure sensor. In an embodiment, the cut is performed for about 1.5 sec at 20 W-100 W, preferably 20 W-30 W. If the pressure loss is sufficient (e.g., about >25% decrease or to a pressure of about <1.5 atm), then a complete cut of the transverse carpal ligament is indicated. If the pressure drop parameters are not met, then an additional cutting cycle(s) may be performed and pressure drop data observed. The additional cutting cycle(s), in an embodiment, may be at the same power setting and duration (e.g., about 1.5 sec at 20 W-100 W). In some embodiments, the balloon 400 shape can be checked using fluoroscopy after each cut cycle to prevent peripheral tissue damage in the event the TCL has been fully transected without causing a pressure drop of >1.5 ATM. Based on a combination of the pressure monitoring and the fluoroscopy the balloon 400 and electrode position 500 can be monitored and adjusted if necessary. If more than a predetermined cutting cycles have been attempted and the TCL has not successfully been divided, the balloon 400 can be deflated and the device 200 can be removed and re-evaluated for proper positioning of the device prior to further attempts at cutting or alternatively abandon the procedure and proceed with open carpal tunnel release.

Complete division of the transverse carpal ligament may be confirmed additionally or alternatively by conformational change of balloon 400 with loss of waisting in the lateral view and/or anterior-posterior views. In some embodiments, confirmation of the division can also be confirmed through readings from one or more sensors of the device 200. Similarly, in some embodiments, complete division of the target tissue can be confirmed by direct/endoscopic visualization.

Once complete division of the transverse carpal ligament is achieved, balloon 400 may be deflated (e.g., using an endoflator), catheter 300 and the optional guide wire 1802 can removed from the patients hand and wrist, and appropriate sterile dressings and splints are applied. In particular, the device 200 can be gently withdrawn from the carpal tunnel and out from the skin, avoiding traction of the surrounding tissue. Retractors can be used to facilitate this process. Subsequently the guide wire 1802 can be removed from the patient and ensure adequate hemostasis. In some embodiments, the device 200 can be discarded. In some embodiments, the incisions can be cleaned and closed using standard techniques.

Additionally or alternatively, in various embodiments, a sizing tool (not shown) may optionally be used to determine an appropriately-sized device 200, 700 for the target anatomy (e.g., based on the size of the carpal tunnel) prior to performing a medical procedure. In an embodiment, the sizing tool may include a balloon catheter similar in structure to devices 200, 700 and mounted with a flat-film force sensor or a pressure sensor. The sizing tool may be inserted into the carpal tunnel or other target anatomy, and force/pressure measurements taken. The user may assess these measurements, which may be associated with the "waist" created in the balloon by the transverse carpal ligament as previously described, to select a corresponding sized device 200, 700.

Additionally or alternatively, in various embodiments, imaging techniques could be used prior to the procedure to generate a 3-D model of the particular patient's relevant anatomy for use in planning the procedure. Representative imaging techniques include, but are not limited to, radiographs (x-rays), CT scans, MRI studies, and ultrasound. In an embodiment, a 3-D model of the patient's wrist, carpal tunnel and transverse carpal ligament anatomy could be generated, and physicians could analyze the model to assist with pre-procedure planning of the surgical approach, sizing of devices 200, 700, and procedural steps.

Alternatively, it may be easier and/or safer to approach the carpal tunnel using device 200 from the palmar aspect in the opposite direction previously described. This may be the case for some patients based on the anatomic variations from person to person and the ability to accurately image the carpal tunnel, transverse carpal ligament, the median nerve, palmar arch blood vessels and other important anatomic landmarks used to identify the appropriate pathway for device 200 to take in order to accomplish safe and effective division of the transverse carpal ligament.

For use in this direction, balloon 400 and cutting elements 500 of the device 200 may be oriented 180 degrees as compared with the previously described device, and such that the bulbous locking portion 420 of balloon 400 is on the handle-side of device 200.

In some embodiments, ultrasound and fluoroscopy may be used to define the carpal tunnel and identify the anatomic landmarks as before. Ensuring the arterial palmar arch is safely away from the entrance site, a small incision may be made in the palm approximately one centimeter distal to the distal edge of the thenar and hypothenar eminence. Using ultrasound and fluoroscopic guidance, a needle or blunt dissector may be inserted through the incision, guided under the transverse carpal ligament, and toward the wrist. The needle or dissector may be further advanced to tent/exit the skin once it has completely traversed the carpal tunnel at approximately the first or second skin crease of the wrist. Ultrasound may be used to ensure the transverse carpal ligament is the only structure anterior to the needle/dissector and that the median nerve and other structures of the carpal tunnel are posterior. A guide wire 1802 may then be placed through the needle/dissector and the needle/dissector removed. Over the guide wire 1802 or alternatively placed directly using the dissector as a guide, device 200 may be inserted from the palmar aspect of the patient and advanced into the carpal tunnel toward the wrist until the cutting electrodes completely traverse the transverse carpal ligament. Correct position of the device may be confirmed using ultrasound and fluoroscopic imaging using the anatomic landmarks. Also, the nerve stimulation protocol may be used to ensure the medial nerve is safely beneath and posterior to cutting elements 500 and balloon 400 of device 200.

Once this is confirmed the remainder of the cutting procedure follows the same steps as previously described when device 200 is used with an antegrade approach.

The design and function of the device discussed herein provides numerous advantages over conventional devices, systems, and methods. Using the visualization method and the device, surgeons can protect the nerves and other structures from injury by making a careful anatomic assessment before cutting and abandoning the procedure if unsafe anatomic variations are visualized. The coated active lead is designed to provide very precise, focused delivery of a short burst of cutting RF energy only along its narrow sharp edge. This design limits the total zone of injury to a maximum of 1 mm but typically much less. The active lead remains completely stationary during the cutting maneuver, providing for a precise cut, limiting its zone of injury and enhancing the safety of the procedure relative to the conventional devices. The balloon provides much greater anatomic separation between the cutting element and the key anatomic structures than conventional device, enhancing the safety of the procedure. The median and ulnar nerves are displaced far beyond the zone of injury during the procedure, far greater than they are by conventional devices.

While the present disclosure has been described with reference to certain embodiments thereof, it should be understood by those skilled in the art that various changes may be made and equivalents may be substituted without departing from the true spirit and scope of the disclosure. In addition, many modifications may be made to adapt to a particular situation, indication, material and composition of matter, process step or steps, without departing from the spirit and scope of the present disclosure. All such modifications are intended to be within the scope of the claims appended hereto.

What is claimed is:

1. A device for dividing a fibrous structure, the device comprising:
   a catheter having a proximal end, a distal end, a lumen extending therebetween, a distal portion having an opening of the lumen, and a longitudinal axis;
   an expandable member positioned towards the distal end of the catheter and in fluid communication with the lumen of the catheter, the expandable member configured to bias between an inflated state and a deflated state to tension the fibrous structure, in the inflated state the expandable member having a longitudinal axis offset from the longitudinal axis of the catheter with the distal portion of the catheter within the expandable member;
   a plurality of electrosurgical elements configured to deliver electrical energy to the fibrous structure tensioned along the expandable member in a manner that results in division of the tensioned fibrous structure; and
   an insulating member having length, the insulating member directly coupled to an outer surface of the catheter along at least a majority of the length of the insulating member, the insulating member positioned between the expandable member and the plurality of electrosurgical elements, the insulating member having an upper surface with the plurality of electrosurgical elements connected thereto.

2. The device as set forth in claim 1, wherein the expandable member is a balloon.

3. The device as set forth in claim 1, wherein at least a portion of the expandable member has a non-circular or asymmetrical cross-sectional shape.

4. The device as set forth in claim 1, wherein:
   a distal portion of the expandable member includes a shaped profile having a larger diameter than that of a proximal portion of the expandable member; and
   the shaped profile of the distal portion of the expandable member is configured to engage anatomy beyond the fibrous structure to minimize migration of the device during division.

5. The device as set forth in claim 1, wherein the expandable member has an elongated longitudinal profile.

6. The device as set forth in claim 1, wherein the expandable member is configured to contact the fibrous structure and expand outwards to tension the fibrous structure across the plurality of electrosurgical elements.

7. The device as set forth in claim 1, wherein:
   the plurality of electrosurgical elements are situated along a longitudinal dimension of the device; and the expandable member expands radially so as to tension the fibrous structure in a direction substantially transverse to the plurality of electrosurgical elements.

8. The device as set forth in claim 1, wherein:
   the plurality of electrosurgical elements include an active lead and a passive lead; and
   the active lead concentrates the electrical energy such that division of the fibrous tissue occurs along a portion of the tensioned fibrous tissue in contact with the active lead.

9. The device as set forth in claim 8, wherein the active lead has a substantially pointed leading edge.

10. The device as set forth in claim 9, wherein at least a portion of the active lead, excluding the pointed leading edge, is covered by an insulating material such that delivery of the electrical and thermal energy is concentrated at the pointed leading edge of the active lead.

11. The device as set forth in claim 8, wherein the passive lead protrudes above a surface of the device on which it is mounted so as to contact and further tension the fibrous structure.

12. The device as set forth in claim 1, wherein the expandable member having a proximal end coupled to the catheter, and the plurality of electrosurgical elements are situated on the insulating member, the insulating member directly coupled to the outer surface of the catheter more proximally than the expandable member.

13. The device as set forth in claim 1, wherein the insulating member provides an electrically insulative spacer between at least two of the plurality of electrosurgical elements.

14. The device as set forth in claim 1, wherein the insulating member is rigid or semi-rigid.

15. The device as set forth in claim 1, wherein:
the insulating member includes a plurality of grooves in which the plurality of electrosurgical elements are mounted; and
at least an active lead protrudes beyond the upper surface of the insulating member.

16. The device as set forth in claim 1, wherein the plurality of electrosurgical elements are sesquipolar.

17. The device as set forth in claim 1, wherein the insulating member comprises at least one coupling mechanism securing the insulating member to the outer surface of the catheter.

18. The device as set forth in claim 1, wherein the insulating member is a flexible film.

19. The device as set forth in claim 1, wherein a longitudinal axis of the expandable member is offset from a longitudinal axis of the catheter when the expandable member is in the deflated state.

20. The device as set forth in claim 1, further including a handle and a sensor within the handle for measuring at least one of an internal pressure of the expandable member, an external force applied to the expandable member, impedance in an electrosurgical circuit connected to the electrosurgical elements, and current in the plurality of electrosurgical circuit.

21. The device as set forth in claim 20, further including a processor for monitoring the measurements to detect a threshold measurement or change indicative of complete division of the fibrous structure.

22. The device as set forth in claim 1, further including a protective jacket for use during insertion of the device.

23. The device as set forth in claim 1, further comprising a plurality of nerve stimulation electrosurgical elements configured to deliver electrical and thermal energy to detect presence of a motor nerve or a sensing nerve proximal to the plurality of electrosurgical elements.

24. The device as set forth in claim 23, wherein the plurality of nerve stimulation electrosurgical elements include an input electrode and an output electrode for measuring an electrical response between the input electrode and the output electrode.

25. The device as set forth in claim 24, wherein the plurality of nerve stimulation electrosurgical elements are connected to a measurement circuit to detect a change in energy over the input electrode and the output electrode.

26. The device as set forth in claim 23, wherein the plurality of nerve stimulation electrosurgical elements are connected to a separate generator than the plurality of electrosurgical elements.

27. The device as set forth in claim 1, further comprising a jacket situated around the expandable member and the plurality of electrosurgical elements to assists in placement of the distal end of the catheter within a location containing the fibrous structure.

28. The device as set forth in claim 27, further comprising a dilator with a tapered tip for insertion into an insertion site and for receiving the jacket for positioning the jacket within the location containing the fibrous structure.

29. The device as set forth in claim 28, further comprising a guidewire for positioning at least one of the dilator and the jacket within the location containing the fibrous structure.

30. The device as set forth in claim 27, wherein the jacket is one of a flexible material or a rigid material with sufficient structure to maintain a pathway for receiving the distal end of the catheter including the expandable member and the plurality of electrosurgical elements of the device.

31. The device as set forth in claim 27, wherein the jacket is removeable from the distal end of the catheter including the expandable member and the plurality of electrosurgical elements at least distally away from the device or proximally toward the device.

32. The device as set forth in claim 27, wherein the jacket has a tapered to assist in placement within an incision site.

33. The device as set forth in claim 27, wherein the jacket is removable in a plurality of pieces.

34. The device as set forth in claim 1 further including one of a fluoroscopic, ultrasonic, or endoscopic sensor for confirmation of the state of the fibrous structure.

* * * * *